(12) United States Patent
Stanley-Marbell et al.

(10) Patent No.: US 9,462,965 B2
(45) Date of Patent: Oct. 11, 2016

(54) DYNAMIC ADJUSTMENT OF MOBILE DEVICE BASED ON SYSTEM EVENTS

(71) Applicant: Apple Inc., Cupertino, CA (US)

(72) Inventors: Phillip Stanley-Marbell, San Francisco, CA (US); Gaurav Kapoor, Santa Clara, CA (US); Umesh S. Vaishampayan, Santa Clara, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 14/622,631

(22) Filed: Feb. 13, 2015

(65) Prior Publication Data
US 2015/0347204 A1  Dec. 3, 2015

Related U.S. Application Data

(60) Provisional application No. 62/005,940, filed on May 30, 2014.

(51) Int. Cl.
| | |
|---|---|
| *G06F 9/54* | (2006.01) |
| *A61B 5/11* | (2006.01) |
| *G06F 9/48* | (2006.01) |
| *A61B 5/00* | (2006.01) |

(52) U.S. Cl.
CPC ............ *A61B 5/1118* (2013.01); *A61B 5/4866* (2013.01); *A61B 5/7275* (2013.01); *G06F 9/4893* (2013.01); *G06F 9/542* (2013.01)

(58) Field of Classification Search
None
See application file for complete search history.

(56) References Cited

U.S. PATENT DOCUMENTS

| | | | |
|---|---|---|---|
| 6,859,829 B1 | 2/2005 | Parupudi et al. | |
| 6,996,441 B1 | 2/2006 | Tobias | |
| 7,065,575 B1 | 6/2006 | Machiraju et al. | |
| 7,562,234 B2 * | 7/2009 | Conroy | G06F 1/26 713/300 |
| 7,949,888 B2 * | 5/2011 | Cox | G06F 1/3203 323/234 |
| 8,126,993 B2 | 2/2012 | Carraher et al. | |
| 8,305,728 B2 | 11/2012 | Lee et al. | |

(Continued)

FOREIGN PATENT DOCUMENTS

| | | |
|---|---|---|
| EP | 2328324 | 6/2011 |
| EP | 2568384 | 3/2013 |

OTHER PUBLICATIONS

Yan, Tingxin et al., "Fast App Launching for Mobile Devices Using Predictive User Context", MobiSys '12, Jun. 25-29, 2012, ACM 978-1-4503-13-1, Aug. 12, 2006, pp. 1-14.

*Primary Examiner* — Tuan Dao
(74) *Attorney, Agent, or Firm* — Page Ponsford; DLA Piper LLP US

(57) ABSTRACT

In some implementations, a mobile device can be configured to monitor environmental, system and user events associated with the mobile device and/or a peer device. The occurrence of one or more events can trigger adjustments to system settings. The mobile device can be configured to keep frequently invoked applications up to date based on a forecast of predicted invocations by the user. In some implementations, the mobile device can receive push notifications associated with applications that indicate that new content is available for the applications to download. The mobile device can launch the applications associated with the push notifications in the background and download the new content. In some implementations, before running an application or communicating with a peer device, the mobile device can be configured to check energy and data budgets and environmental conditions of the mobile device and/or a peer device to ensure a high quality user experience.

18 Claims, 18 Drawing Sheets

(56) References Cited

U.S. PATENT DOCUMENTS

| | | |
|---|---|---|
| 8,321,057 B2 | 11/2012 | Maly |
| 8,327,349 B2 | 12/2012 | Chu et al. |
| 8,683,037 B2 | 3/2014 | Wyld et al. |
| 2003/0200264 A1 | 10/2003 | Brill |
| 2006/0168014 A1 | 7/2006 | Wang |
| 2007/0067373 A1 | 3/2007 | Higgins et al. |
| 2007/0185933 A1 | 8/2007 | Dao et al. |
| 2008/0114574 A1* | 5/2008 | Chen .................. G06F 19/345 703/2 |
| 2009/0199029 A1 | 8/2009 | Arimilli et al. |
| 2009/0232480 A1* | 9/2009 | Jendbro .............. G11B 27/034 386/224 |
| 2010/0015926 A1 | 1/2010 | Luff |
| 2010/0241888 A1 | 9/2010 | Kaneko et al. |
| 2010/0293049 A1 | 11/2010 | Maher et al. |
| 2010/0332876 A1 | 12/2010 | Fields et al. |
| 2011/0016476 A1 | 1/2011 | Raju |
| 2012/0042002 A1 | 2/2012 | Smith et al. |
| 2012/0135756 A1 | 5/2012 | Rosso et al. |
| 2012/0179502 A1 | 7/2012 | Farooq et al. |
| 2013/0067492 A1 | 3/2013 | Fidler et al. |
| 2013/0204948 A1 | 8/2013 | Zeyliger et al. |
| 2013/0275994 A1 | 10/2013 | Uola et al. |
| 2013/0329562 A1 | 12/2013 | Murakami |
| 2013/0332524 A1 | 12/2013 | Fiala et al. |
| 2014/0067779 A1 | 3/2014 | Ojha |
| 2014/0068207 A1 | 3/2014 | Aslot et al. |
| 2014/0075234 A1 | 3/2014 | Stekkelpak et al. |
| 2014/0082383 A1 | 3/2014 | de Cesare et al. |
| 2014/0117921 A1 | 5/2014 | Suomela |
| 2014/0156834 A1 | 6/2014 | Wyld et al. |

\* cited by examiner

DYNAMIC ADJUSTMENT OF MOBILE DEVICE BASED ON SYSTEM EVENTS

CROSS-REFERENCE TO RELATED APPLICATIONS

This application claims priority to U.S. Provisional Patent Application No. 62/005,940, filed May 30, 2014, entitled "DYNAMIC ADJUSTMENT OF MOBILE DEVICE BASED ON SYSTEM EVENTS," the content of which is incorporated herein by reference in its entirety.

TECHNICAL FIELD

The disclosure generally relates to managing system resources based on system events.

BACKGROUND

Mobile computing devices are typically battery operated. Some mobile computing devices can wirelessly access network resources over cellular data and/or Wi-Fi network connections. These mobile devices are often constrained by battery capacity and/or limits on cellular data usage.

Some mobile computing devices allow a user to run applications that access data from network resources. The user typically invokes an application and then must wait for the application to retrieve data from the network resources so that the application can present current updated content.

SUMMARY

In some implementations, a mobile device can be configured to monitor environmental, system and user events. The mobile device can be configured to detect the occurrence of one or more events that can trigger adjustments to system settings.

In some implementations, the mobile device can be configured with predefined and/or dynamically defined attributes. The attributes can be used by the system to track system events. The attribute events can be stored and later used to predict future occurrences of the attribute events. The stored attribute events can be used by the system to make decisions regarding processing performed by the mobile device. The attributes can be associated with budgets that allow for budgeting resources to support future events or activities on the system.

In some implementations, various applications, functions and processes running on the mobile device can submit attribute events. The applications, functions and processes can later request forecasts based on the submitted events. The applications, functions and processes can perform budgeting based on the budgets associated with the attributes and the costs associated with reported events. The applications, functions, and processes can be associated with the operating system of the mobile device or third party applications, for example.

In some implementations, the mobile device can be configured to keep frequently invoked applications up to date. The mobile device can keep track of when applications are invoked by the user. Based on the invocation information, the mobile device can forecast when during the day the applications are invoked. The mobile device can then preemptively launch the applications and download updates so that the user can invoke the applications and view current updated content without having to wait for the application to download updated content.

In some implementations, the mobile device can receive push notifications associated with applications that indicate that new content is available for the applications to download. The mobile device can launch the applications associated with the push notifications in the background and download the new content. After the content is downloaded, the mobile device can present a graphical interface indicating to the user that the push notification was received. The user can then invoke the applications and view the updated content.

In some implementations, the mobile device can be configured to perform out of process downloads and/or uploads of content for applications on the mobile device. For example, a dedicated process can be configured on the mobile device for downloading and/or uploading content for applications on the mobile device. The applications can be suspended or terminated while the upload/download is being performed. The applications can be invoked when the upload/download is complete.

In some implementations, before running an application or accessing a network interface, the mobile device can be configured to check battery power and cellular data usage budgets to ensure that enough power and data is available for user invoked operations. Before launching an application in the background, the mobile device can check usage statistics to determine whether the application is likely to be invoked by a user in the near future.

In some implementations, attribute event data can be shared between mobile devices owned by the same user. The mobile device can receive event data from a peer device and make decisions regarding interactions or operations involving the peer device based on the received event data. The event data can be shared as forecasts, statistics, and/or raw (e.g., unprocessed) event data. The mobile device can determine whether to communicate with the peer device based on the received event data, for example.

Particular implementations provide at least the following advantages: Battery power can be conserved by dynamically adjusting components of the mobile device in response to detected events. The user experience can be improved by anticipating when the user will invoke applications and downloading content so that the user will view updated content upon invoking an application.

Details of one or more implementations are set forth in the accompanying drawings and the description below. Other features, aspects, and potential advantages will be apparent from the description and drawings, and from the claims.

DESCRIPTION OF DRAWINGS

Like reference symbols in the various drawings indicate like elements.

DETAILED DESCRIPTION

Overview

Described herein is a system architecture for enabling adaptation of a mobile device based on various system events to facilitate tradeoffs between battery lifetime, power requirements, thermal management and performance. The system provides the underlying event gathering architecture and a set of heuristic processes that learn from the system events to maximize battery life without noticeable degradation in the user experience. The system monitors system-defined and client-defined attributes and can use the system-defined and client-defined attributes to predict or forecast the occurrence of future events. This system can anticipate the system's future behavior as well as the user's expectation of device performance based on dynamically gathered statistics and/or explicitly specified user intent. The system can determine which hardware and software control parameters to set and to what values to set the parameters in order to improve the user experience for the anticipated system behavior. The system leverages system monitoring and hardware control to achieve an overall improvement in the user experience while extending system and network resources available to the mobile device. Thus, the system can maximize system and network resources while minimizing the impact to the user experience.

Data Collection—User Centric Statistics

Figure 1:
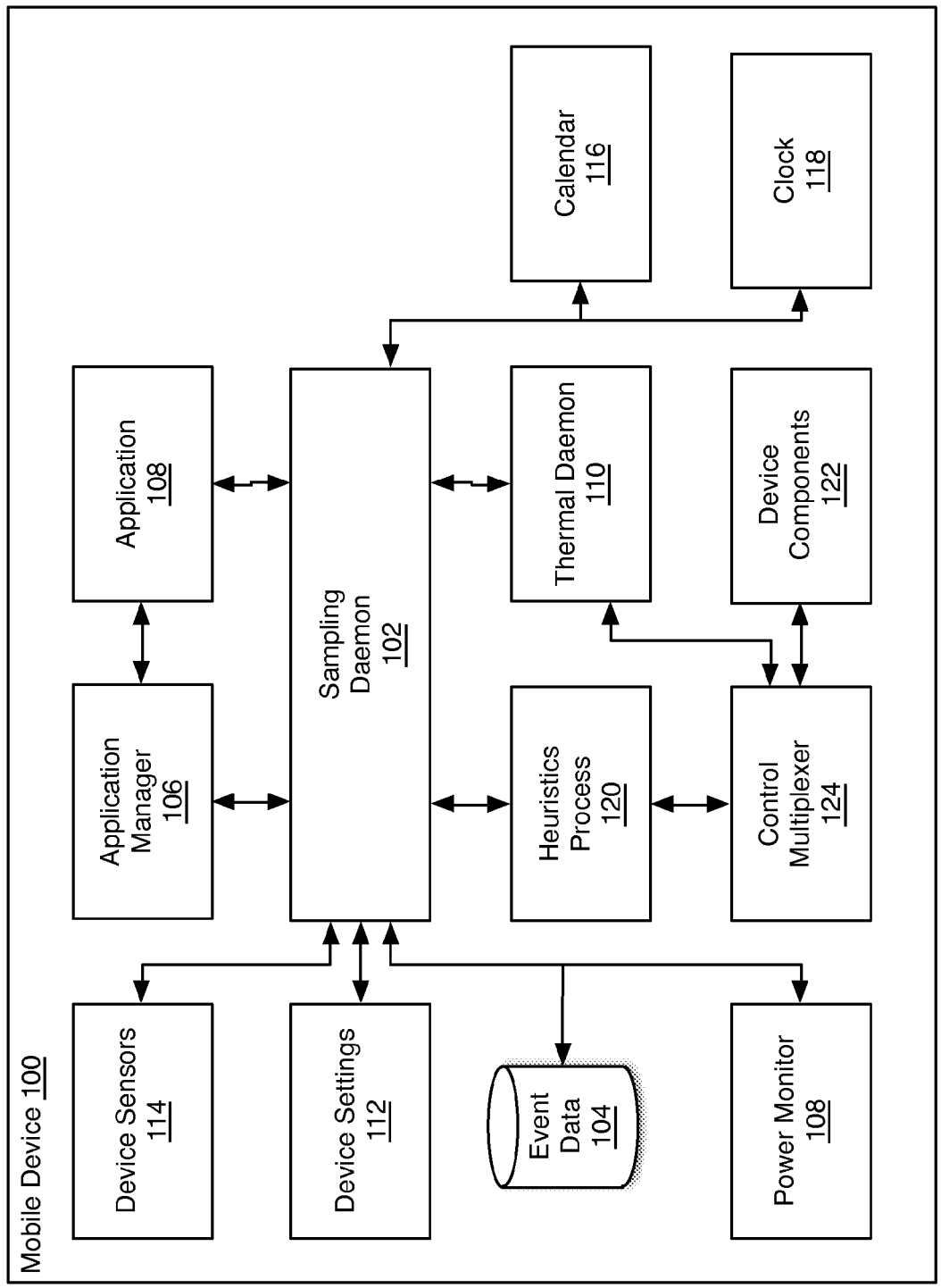
FIG. 1 illustrates a mobile device configured to perform dynamic adjustment of the mobile device.

FIG. 1 illustrates an example mobile device 100 configured to perform dynamic adjustment of the mobile device 100. In some implementations, mobile device 100 can include a sampling daemon 102 that collects events related to device conditions, network conditions, system services (e.g., daemons) and user behavior. For example, sampling daemon 102 can collect statistics related to applications, sensors, and user input received by mobile device 100 and store the statistics in event data store 104. The statistics can be reported to sampling daemon 102 by various clients (e.g., applications, utilities, functions, third-party applications, etc.) running on mobile device 100 using predefined or client-defined attributes reported as events.

Data Collection—Events & Attributes

In some implementations, mobile device 100 can be configured with a framework for collecting system and/or application events. For example, mobile device 100 can be configured with application programming interfaces (API) that allow various applications, utilities and other components of mobile device 100 to submit events to sampling daemon 102 for later statistical analysis.

In some implementations, each event recorded by sampling daemon 102 in event data store 104 can include an attribute name (e.g., "bundleId"), an attribute value (e.g., "contacts"), anonymized beacon information, anonymized location information, date information (e.g., GMT date of event), time information (e.g., localized 24 hour time of event), network quality information, processor utilization metrics, disk input/output metrics, identification of the current user and/or type of event (e.g., start, stop, occurred). For example, the attribute name can identify the type of attribute associated with the event. The attribute name can be used to identify a particular metric being tracked by sampling daemon 102, for example. The attribute value can be a value (e.g., string, integer, floating point) associated with the attribute. The anonymized beacon information can indicate which wireless beacons (e.g., Bluetooth, Bluetooth Low Energy, Wi-Fi, etc.) are in range of the mobile device without tying or associating the beacon information to the user or the device. Similarly, the anonymized location information can identify the location of the mobile device without tying or associating the location information to the user or the device. For example, location information can be derived from satellite data (e.g., global positioning satellite system), cellular data, Wi-Fi data, Bluetooth data using various transceivers configured on mobile device 100. Network quality information can indicate the quality of the mobile device's network (e.g., Wi-Fi, cellular, satellite, etc.) connection as detected by mobile device 100 when the event occurred.

In some implementations, the event data for each event can indicate that the event occurred, started or stopped. For example, time accounting (e.g., duration accounting) can be performed on pairs of events for the same attribute that indicate a start event and a stop event for the attribute. For example, sampling daemon 102 can receive a start event for attribute "bundleId" having a value "contacts". Later, sampling daemon 102 can receive a stop event for attribute "bundleId" having a value "contacts". Sampling daemon 102 can compare the time of the start event to the time of the stop event to determine how long (e.g., time duration) the "contacts" application was active. In some implementations, events that are not subject to time accounting can be recorded as point events (e.g., a single occurrence). For example, an event associated with the "batteryLevel" system attribute that specifies the instantaneous battery level at the time of the event can simply be recorded as an occurrence of the event.

Table 1, below, is provides an example of attribute event entries recorded by sampling daemon 102 in event data store 104. The first entry records a "bundleId" event that indicates that the "contacts" application has been invoked by user "Fred." This "bundleId" event is a start event indicating that Fred has begun using the contacts application. The second entry is a "batteryLevel" event entry that indicates that the battery level of mobile device 100 is at 46%; this event is an occurrence type event (e.g., single point event). The third entry is a "personName" event that associated with the value "George." The "personName" event is used to record the fact that user Fred has accessed the contact information for contact "George" in the contacts application; this is an occurrence type event. The fourth entry records a "bundleId" event that indicates that the "contacts" application has been closed or hidden by user "Fred." This bundleId event is a stop event indicating that Fred has stopped using the contacts application. By recording start and stop events for the "bundleId" attribute, sampling daemon 102 can determine that user Fred has used the contacts application for 8 minutes on May 12, 2014 based on the timestamps corresponding to the start and stop events. This attribute event information can be used, for example, to forecast user activity related to applications on mobile device 100 and with respect to the contacts application in particular.

TABLE 1

| Attr. Name | Value | Beacons | Location | Date | Time | Network Quality | User ID | State |
|---|---|---|---|---|---|---|---|---|
| bundleId | "contacts" | B1, B2 . . . | Location1 | 2014 May 12 | 1421 | 8 | Fred | start |
| batteryLevel | 46 | B1, B2 . . . | Location2 | 2014 May 12 | 1424 | 8 | Fred | occur |
| personName | "George" | B1, B2 . . . | Location2 | 2014 May 12 | 1426 | 8 | Fred | occur |
| bundleId | "contacts" | B1, B2 . . . | Location1 | 2014 May 12 | 1429 | 8 | Fred | stop |

Predefined Attributes

In some implementations, event data can be submitted to sampling daemon 102 using well-known or predefined attributes. The well-known or predefined attributes can be generic system attributes that can be used by various applications, utilities, functions or other components of mobile device 100 to submit event data to sampling daemon 102. While the attribute definition (e.g., attribute name, data type of associated value, etc.) is predefined, the values assigned to the predefined attribute can vary from event to event. For example, mobile device 100 can be configured with predefined attributes "bundleId" for identifying applications and "personName" for identifying people of interest. The values assigned to "bundleId" can vary based on which application is active on mobile device 100. The values assigned to "personName" can vary based on user input. For example, if a user selects an email message from "George," then the "personName" attribute value can be set to "George." If a user selects a contacts entry associated with "Bob," then the "personName" attribute value can be set to "Bob." When an application, utility, function or other component of mobile device 100 submits an event to sampling daemon 102 using the predefined attributes, the application, utility, function or other component can specify the value to be associated with the predefined attribute for that event. Examples of predefined or well-known system events are described in the following paragraphs.

In some implementations, mobile device 100 can be configured with a predefined attribute (e.g., "system.bundleId") that specifies a name or identifier for an application (e.g., application bundle) installed on mobile device 100. When an application is launched, the application manager 106 (e.g., responsible for launching applications) can use an API of the sampling daemon 102 to submit the identifier or name of the application (e.g., "contacts" for the contacts application) as the value for the "system.bundleId" system attribute. The sampling daemon 102 can record the occurrence of the launching of the "contacts" application as an event in event data store 104, for example, along with other event data, as described above. Alternatively, the application can use the API of the sampling daemon 102 to indicate start and stop events corresponding to when the application "contacts" is invoked and when the application is hidden or closed, respectively. For example, the "bundleId" attribute can be used to record application launch events on mobile device 100. The "bundleId" attribute can be used to record application termination events on mobile device 100. By specifying start and stop events associated with the "bundleId" attribute, rather than just the occurrence of an event, the sampling daemon 102 can determine how long the "contacts" application was used by the user of mobile device 100.

In some implementations, mobile device 100 can be configured with a predefined attribute (e.g., "system.personName") that specifies a name or identifier of a user of mobile device 100 or a person of interest to the user of mobile device 100. For example, upon logging into, waking or otherwise accessing mobile device 100, an event associated with the "personName" attribute can be generated and submitted to sampling daemon 102 that identifies the current user of mobile device 100. When the user accesses data associated with another person, a "personName" attribute event can be generated and submitted to sampling daemon 102 that identifies the other person as a person of interest to the user.

In some implementations, mobile device 100 can be configured with a predefined attribute (e.g., "system.anonymizedLocation") that indicates a location of the mobile device 100. For example, mobile device 100 can generate and submit an event to sampling daemon 102 associated with the "anonymizedLocation" attribute that specifies the location of the mobile device 100 at the time when the event is generated. The location data can be anonymized so that the location cannot be later tied or associated to a particular user or device. The "anonymizedLocation" attribute event can be generated and stored, for example, whenever the user is using a location-based service of mobile device 100.

In some implementations, mobile device 100 can be configured with a predefined attribute (e.g., "system.airplaneMode") that indicates that the airplane mode of mobile device 100 is on or off. For example, when a user turns airplane mode on or off, mobile device 100 can generate and submit an event to sampling daemon 102 that indicates the airplane mode state at the time of the event. For example, the value of the "airplaneMode" attribute can be set to true (e.g., one) when airplaneMode is turned on and set to false (e.g., zero) when the airplane mode is off. Sampling daemon 102 can, in turn, store the "airplaneMode" event, including "airplaneMode" attribute value in event data store 104.

In some implementations, mobile device 100 can be configured with a predefined attribute (e.g., "system.cable- Plugin") that indicates that the power cable of mobile device 100 is plugged in or is not plugged in. For example, when mobile device 100 detects that the power cable has been unplugged, mobile device 100 can generate an event that indicates that the "cablePlugin" attribute value is false (e.g., zero). When mobile device 100 detects that the power cable has been plugged into mobile device 100, mobile device 100 can generate an event that indicates that the "cablePlugin" attribute is true (e.g., one). Mobile device 100 can submit the "cablePlugin" event to sampling daemon 102 for storage in event data store 104.

In some implementations, mobile device 100 can be configured with a predefined attribute (e.g., "system.screenLock") that indicates whether the display screen of mobile device 100 is locked or unlocked. For example, mobile device 100 can detect when the display screen of mobile device 100 has been locked (e.g., by the system or by a user) or unlocked (e.g., by the user). Upon detecting the locking or unlocking of the display screen, mobile device 100 can generate an event that includes the "screenLock" attribute and set the "screenLock" attribute value for the event to true (e.g., locked, integer one) or false (e.g., unlocked, integer zero) to indicate whether the display screen of mobile device 100 was locked or unlocked. Mobile device 100 can submit the "screenLock" event to sampling daemon 102 for storage in event data store 104.

In some implementations, mobile device 100 can be configured with a predefined attribute (e.g., "system.sleepWake") that indicates whether mobile device 100 is in sleep mode. For example, mobile device 100 can detect when mobile device 100 enters sleep mode. Mobile device 100 can detect when mobile device 100 exits sleep mode (e.g., wakes). Upon detecting entering or exiting sleep mode, mobile device can generate an event that includes the "sleepWake" attribute and sets the attribute value to true or false (e.g., integer one or zero, respectively) to indicate the sleep mode state of the mobile device 100 at the time of the "sleepWake" event. Mobile device 100 can submit the "sleepWake" event to sampling daemon 102 for storage in the event data store 104.

In some implementations, mobile device 100 can be configured with a predefined attribute (e.g., "system.backlight") that indicates whether the display of mobile device 100 is lit. The "backlight" attribute can be assigned a value that indicates the intensity or level of the backlight. For example, a user of mobile device 100 can adjust the intensity of the lighting (backlight) of the display of mobile device 100. The user can increase the intensity of the backlight when the ambient lighting is bright. The user can decrease the intensity of the backlight when the ambient lighting is dark. Upon detecting a change in backlight setting, mobile device 100 can generate an event that includes the "backlight" attribute and sets the attribute value to the adjusted backlight setting (e.g., intensity level). Mobile device 100 can submit the "backlight" change event to sampling daemon 102 for storage in the event data store 104.

In some implementations, mobile device 100 can be configured with a predefined attribute (e.g., "system.ALS") that indicates the ambient light intensity value as detected by the ambient light sensor of mobile device 100. The "ALS" attribute can be assigned a value that indicates the intensity or level of the ambient light surrounding mobile device 100. For example, the ambient light sensor of mobile device 100 can detect a change in the intensity of ambient light. Mobile device 100 can determine that the change in intensity exceeds some threshold value. Upon detecting a change in ambient light that exceeds the threshold value, mobile device 100 can generate an event that includes the "ALS" attribute and sets the attribute value to the detected ambient light intensity value. Mobile device 100 can submit the "ALS" change event to sampling daemon 102 for storage in the event data store 104.

In some implementations, mobile device 100 can be configured with a predefined attribute (e.g., "system.proximity") that indicates the when the proximity sensor of mobile device 100 detects that the display of mobile device 100 is near an object (e.g., the user's face, on a table, etc.). The "proximity" attribute can be assigned a value that indicates whether the display of the mobile device is proximate to an object (e.g., true, false, 0, 1). For example, the proximity sensor of mobile device 100 can detect a change in proximity. Upon detecting a change in proximity, mobile device 100 can generate an event that includes the "proximity" attribute and sets the attribute value to true (e.g., one) when the mobile device 100 is proximate to an object and false (e.g., zero) when the mobile device 100 is not proximate to an object. Mobile device 100 can submit the "proximity" change event to sampling daemon 102 for storage in the event data store 104.

In some implementations, mobile device 100 can be configured with a predefined attribute (e.g., "system.motionState") that indicates the type of motion detected by mobile device 100. The "motionState" attribute can be assigned a value that indicates whether the mobile device is stationary, moving, running, driving, walking, etc. For example, the motion sensor (e.g., accelerometer) of mobile device 100 can detect movement of the mobile device 100. The mobile device 100 can classify the detected movement based on patterns of motion detected in the detected movement. The patterns of motion can be classified into user activities, such as when the user is stationary, moving, running, driving, walking, etc. Upon detecting a change in movement, mobile device 100 can generate an event that includes the "motionState" attribute and sets the attribute value to the type of movement (e.g., stationary, running, walking, driving, etc.) detected. Mobile device 100 can submit the "motionState" event to sampling daemon 102 for storage in the event data store 104.

In some implementations, mobile device 100 can be configured with a predefined attribute (e.g., "system.networkQuality") that indicates the quality of the network connection detected by mobile device 100. The "networkQuality" attribute can be assigned a value that indicates the network throughput value over an n-second (e.g., 1 millisecond, 2 seconds, etc.) period of time. For example, mobile device 100 can connect to a data network (e.g., cellular data, satellite data, Wi-Fi, Internet, etc.). The mobile device 100 can monitor the data throughput of the network connection over a period of time (e.g., 5 seconds). The mobile device can calculate the amount of data transmitted per second (e.g., bits/second, bytes/second, etc.). Upon detecting a change in throughput or upon creating a new network connection, mobile device 100 can generate an event that includes the "networkQuality" attribute and sets the attribute value to the calculated throughput value. Mobile device 100 can submit the "networkQuality" event to sampling daemon 102 for storage in the event data store 104.

In some implementations, mobile device 100 can be configured with a predefined attribute (e.g., "system.batteryLevel") that indicates an instantaneous charge level of the internal battery of mobile device 100. The "batteryLevel" attribute can be assigned a value that indicates the charge level (e.g., percentage) of the battery. For example, mobile device 100 can periodically (e.g., every 5 seconds, every minute, every 15 minutes, etc.) determine the charge level of the battery and generate a "batteryLevel" event to record the charge level of the battery. Mobile device 100 can monitor the battery charge level and determine when the charge level changes by a threshold amount and generate a "batteryLevel" event to record the charge level of the battery. Mobile device 100 can submit the "batteryLevel" event to sampling daemon 102 for storage in the event data store 104.

In some implementations, mobile device 100 can be configured with a predefined attribute (e.g., "system.thermalLevel") that indicates the thermal level of mobile device 100. For example, the thermal level of mobile device 100 can be the current operating temperature of the mobile device (e.g., degrees Celsius). The thermal level of the mobile device 100 can be a level (e.g., high, medium, low, normal, abnormal, etc.) that represents a range of temperature values. For example, mobile device 100 can be configured with a utility or function for monitoring the thermal state of the mobile device 100. Upon detecting a change in temperature or change in thermal level, the thermal utility of mobile device 100 can generate an event that includes the "thermalLevel" attribute and sets the attribute value to the operating temperature or current thermal level. Mobile device 100 can submit the "thermalLevel" event to sampling daemon 102 for storage in the event data store 104.

In some implementations, mobile device 100 can be configured with a predefined attribute (e.g., "system.energy") that indicates the energy usage of mobile device 100 over an n-second (e.g., 2 millisecond, 3 second, etc.) period of time. For example, when a user invokes a function (e.g., invocation of an application, illumination of the display, transmission of data, etc.) of mobile device 100, mobile device 100 can monitor the energy usage over a period of time that the function is executing to estimate how much energy each activity or function uses. The mobile device 100 can then generate an event that includes the "energy" attribute and sets the attribute value to the calculated average energy usage. Mobile device 100 can submit the "energy" event to sampling daemon 102 for storage in the event data store 104.

In some implementations, mobile device 100 can be configured with a predefined attribute (e.g., "system.networkBytes") that indicates the network data usage of mobile device 100 over a n-second (e.g., 2 millisecond, 3 second, etc.) period of time. For example, when a user invokes a function or initiates an operation that requires transmission of data over a network connection of mobile device 100, mobile device 100 can monitor the network data usage over a period of time to estimate how much network data each activity or function uses or transmits. The mobile device 100 can then generate an event that includes the "networkBytes" attribute and sets the attribute value to the calculated average network data usage. Mobile device 100 can submit the "networkBytes" event to sampling daemon 102 for storage in the event data store 104.

Other predefined attributes can include a "system.chargingStatus" attribute having a true/false (e.g., one/zero) attribute value indicating whether the mobile device 100 is charging its battery, a "system.batteryCapacity" attribute having an attribute value that indicates the current battery charge (e.g., in mAh, proportional to batteryLevel), and a "system.devicePresence" attribute having a device identifier (e.g., string) attribute value that tracks the appearances of peer devices. For example, the "devicePresence" attribute can be used to forecast the appearance of peer devices when scheduling peer-to-peer data sharing.

Custom Attributes

In some implementations, client-specific attributes can be dynamically defined by clients of sampling daemon 102. For example, instead of using the attributes predefined (e.g., in sampling daemon 102 or the operating system) and configured on mobile device 100, clients (e.g., third party applications) can dynamically define their own event attributes. For example, an email application can dynamically (e.g., at runtime) create a "mailbox" attribute. The email application ("mailapp") can use an API of sampling daemon 102 to define the attribute name (e.g., "mailapp.mailbox") and the attribute value type (e.g., string, integer, float). Once the client has created (registered) the new custom attribute, the client can use the attribute to generate events to be stored in event data store 104. For example, the mailapp can use the "mailbox" attribute to report which mailbox in the email application that the user is accessing. If the user is accessing a "work" mailbox, then the mailapp can create an event using the "mailapp.mailbox" attribute and set the value of the attribute to "work" to record the user's accessing the "work" mailbox. The sampling daemon 102 and the client can then use the stored mailbox event information to predict when the user is likely to access the "work" mailbox in the future, for example.

In some implementations, when a client application is removed (e.g., deleted, uninstalled) from mobile device 100, attributes created by the client application can be deleted from mobile device 100. Moreover, when the client application is removed, event data associated with the client application can be deleted. For example, if mailapp is deleted from mobile device 100, the attribute "mailapp.mailbox" can be deleted from mobile device 100 along with all of the event data associated with the mailapp.

Example Event Generating Clients

In some implementations, sampling daemon 102 can receive application events (e.g., "system.bundleId" events) from application manager process 106. For example, application manager 106 can be a process that starts, stops and monitors applications (e.g., application 108) on mobile device 100. In some implementations, application manager 106 can report start and stop times (e.g., "bundleId" start and stop events) for applications running on mobile device 100 to sampling daemon 102. For example, when a user invokes or launches an application, application manager 106 can notify sampling daemon 102 of the application invocation by submitting a "bundleId" start event for the invoked application that specifies the name or identifier of the application. In some implementations, application manager 106 can indicate to sampling daemon 102 that the application launch was initiated in response to a push notification, user invocation or a predicted or forecasted user application invocation. When an application terminates, application manager 106 can notify sampling daemon 102 that the application is no longer running by submitting a "bundleId" stop event for the application that specifies the name or identifier of the application.

In some implementations, sampling daemon 102 can use the application start and end events (e.g., "bundleId" attribute events) to generate a history of usage times per application. For example, the history of usage times per application can include for each execution of an application an amount of time that has passed since the last execution of the application and execution duration. Sampling daemon 102 can maintain a separate history of user-invoked application launches and/or system launched (e.g., automatically launched) applications. Thus, sampling daemon 102 can maintain usage statistics for all applications that are executed on mobile device 100.

In some implementations, sampling daemon 102 can receive power events from power monitor process 108. For example, power monitor 108 can monitor battery capacity, discharge, usage, and charging characteristics for mobile device 100. Power monitor 108 can determine when the mobile device 100 is plugged into external power sources and when the mobile device 100 is on battery power. Power monitor 108 can notify sampling daemon 102 when the mobile device 100 is plugged into external power. For example, power monitor 108 can send a "cablePlugin" event with a "cablePlugin" attribute value of one (e.g., true) to sampling daemon 102 when power monitor detects that mobile device 100 is plugged into an external power source. The event can include the battery charge at the time when the external power source is connected. Power monitor 108 can send "energy" attribute events to sampling daemon 102 to report battery usage.

In some implementations, power monitor 108 can notify sampling daemon 102 when the mobile device 100 is disconnected from external power. For example, power monitor 108 can send a "cablePlugin" event with a "cablePlugin" attribute value of zero (e.g., false) to sampling daemon 102 when power monitor detects that mobile device 100 is disconnected from an external power source. The message can include the battery charge at the time when the external power source is disconnected. Thus, sampling daemon 102 can maintain statistics describing the charging distribution (e.g., charge over time) of the batteries of the mobile device 100. The charging distribution statistics can include an amount of time since the last charge (e.g., time since plugged into external power) and the change in battery charge attributable to the charging (e.g., start level of charge, end level of charge).

In some implementations, power monitor 108 can notify sampling daemon 102 of changes in battery charge throughout the day. For example, power monitor 108 can be notified when applications start and stop and, in response to the notifications, determine the amount of battery power discharged during the period and the amount of charge remaining in the battery and transmit this information to sampling daemon 102. For example, power monitor 108 can send a "system.energy" event to sampling daemon 102 to indicate the amount of energy consumed over the period of time during which the application was active.

In some implementations, sampling daemon 102 can receive device temperature statistics from thermal daemon 110. For example, thermal daemon 110 can monitor the operating temperature conditions of the mobile device 100 using one or more temperature sensors. Thermal daemon 110 can be configured to periodically report temperature changes to sampling daemon 102. For example, thermal daemon 110 can determine the operating temperature of mobile device 100 every five seconds and report the temperature or thermal level of mobile device 100 to sampling daemon 102. For example, thermal daemon 110 can send a "system.thermalLevel" event to sampling daemon 102 to report the current operating temperature or thermal level of mobile device 100. Sampling daemon 102 can store the reported temperatures in event data store 104.

In some implementations, sampling daemon 102 can receive device settings statistics from device settings process 112. For example, device settings process 112 can be a function or process of the operating system of mobile device 100. Device settings process 112 can, for example, receive user input to adjust various device settings, such as turning on/off airplane mode, turning on/off Wi-Fi, turning on/off roaming, etc. Device settings process 112 can report changes to device settings to sampling daemon 102. Each device setting can have a corresponding predefined event attribute. For example, device settings process 112 can send a "system.airplaneMode" event to sampling daemon 102 when the user turns on or off airplane mode on the mobile device 100. Sampling daemon 102 can generate and store statistics for the device settings based on the received events and attribute values. For example, for each time a setting is enabled (or disabled), sampling daemon 102 can store data that indicates the amount of time that has passed since the setting was previously enabled and the amount of time (e.g., duration) that the setting was enabled.

Similarly, in some implementations, sampling daemon 102 can receive notifications from other mobile device 100 components (e.g., device sensors 114) when other events occur. For example, sampling daemon 102 can receive notifications when the mobile device's screen is turned on or off (e.g., "system.backlight" event), when the mobile device 100 is held next to the user's face (e.g., "system.proximity" event), when a cell tower handoff is detected, when the baseband processor is in a search mode (e.g., "system.btlescan" event), when the mobile device 100 has detected that the user is walking, running and/or driving (e.g., "system.motionState" event). In each case, the sampling daemon 102 can receive a notification at the start and end of the event. In each case, the sampling daemon 102 can generate and store statistics indicating the amount of time that has passed since the event was last detected and the duration of the event. The sampling daemon 102 can receive other event notifications and generate other statistics as described further below with respect to specific use cases and scenarios.

Application Events

In some implementations, sampling daemon 102 can receive event information from applications on mobile device 100. For example, applications on mobile device 100 can generate events that include predefined or dynamically defined attributes to sampling daemon 102 to track various application-specific events. For example, sampling daemon 102 can receive calendar events (e.g., including a "calendar.appointment," "calendar.meeting," or "calendar.reminder" attribute etc.) from calendar application 116. The calendar events can include a "calendar.appointment," "calendar.meeting," or "calendar.reminder" attribute that has values that specify locations, times, or other data associated with various calendar events or functions. Sampling daemon 102 can store the attribute name, attribute duration and/or time when the attribute is scheduled to occur, for example. In some implementations, sampling daemon 102 can receive clock events (e.g., including a "clock.alarm" attribute) from clock application 118. For example, sampling daemon 102 can store the attribute name (e.g., "clock.alarm") and a value indicating a time when the alarm is scheduled to occur. Sampling daemon 102 can receive event information from other applications (e.g., media application, passbook application, etc.) as described further below.

Application Statistics

In some implementations, sampling daemon 102 can collect application statistics across application launch events. For example, sampling daemon 102 can collect statistics (e.g., events, "bundleId" attribute values) for each application across many invocations of the application. For example, each application can be identified with a hash of its executable's filesystem path and the executable's content's hash so that different versions of the same application can be handled as distinct applications. The application hash value can be submitted to sampling daemon 102 in a "bundleId" event as a value for the "bundleId" attribute, for example.

In some implementations, sampling daemon 102 can maintain a counter that tracks background task completion assertion events for each application. For example, each time an application is run as a background task (e.g., not visible in the foreground and/or currently in use by the user) the application or application manager 106 can notify sampling daemon 102 when the application is terminated or is suspended and the sampling daemon 102 can increment the counter. Sampling daemon 102 can maintain a counter that tracks the cumulative number of seconds across application launches that the application has run in the background. For example, sampling daemon 102 can analyze "bundleId" start and stop events to determine when applications are started and stopped and use the timestamps of start and stop events to determine how long the application has run. In some implementations, sampling daemon 102 can maintain separate counters that count the number of data connections, track the amount of network data traffic (e.g., in bytes), track the duration and size of filesystem operations and/or track the number of threads associated with each application. Sampling daemon 102 can maintain a count of the cumulative amount of time an application remains active across application launches, for example. These are just a few examples of the types of application statistics that can be generated by sampling daemon 102 based on events and attribute data received by sampling daemon 102 and stored in event data store 104. Other statistics can be generated or collected, as described further below.

Heuristics

In some implementations, mobile device 100 can be configured with heuristic processes that can adjust settings of device components based on events detected by sampling daemon 102. For example, heuristic processes 120 can include one or more processes that are configured (e.g., programmed) to adjust various system settings (e.g., CPU power, baseband processor power, display lighting, etc.) in response to one or more trigger events and/or based on the statistics collected or generated by sampling daemon 102.

In some implementations, heuristic process 120 can register with sampling daemon 102 to be invoked or activated when a predefined set of criteria is met (e.g., the occurrence of some trigger event). Trigger events might include the invocation of a media player application (e.g., "bundleId" event) or detecting that the user has started walking, running, driving, etc. (e.g., "motionState" event). The trigger event can be generalized to invoke a heuristic process 120 when some property, data, statistic, event, attribute, attribute value etc. is detected in event data 104 or by sampling daemon 102. For example, a heuristic process 120 can be invoked when sampling daemon 102 receives an application start notification (e.g., "bundleId" start event that specifies a specific application) or a temperature (e.g., "thermalLevel" event) above a certain threshold value. A heuristic process 120 can be invoked when sampling daemon 102 receives an event associated with a specified attribute or attribute value. A heuristic process 120 can register to be invoked when a single event occurs or statistic is observed. A heuristic process 120 can register to be invoked when a combination of events, data, attributes, attribute values and/or statistics are observed or detected. Heuristic process 120 can be triggered or invoked in response to specific user input (e.g., "airplaneMode" event, "sleepWake" event, etc.). When sampling process 102 detects the events for which a heuristic process 120 registered, sampling process 102 can invoke the heuristic process 120.

In some implementations, when a heuristic process 120 is invoked, the heuristic process 120 can communicate with sampling daemon 102 to retrieve event data from event data store 104. The heuristic process 120 can process the event data and/or other data that the heuristic process 120 collects on its own to determine how to adjust system settings to improve the performance of mobile device 100, improve the user's experience while using mobile device 100 and/or avert future problems with mobile device 100.

In some implementations, heuristic process 120 can make settings recommendations that can cause a change in the settings of various device components 122 of mobile device 100. For example, device components can include CPU, GPU, baseband processor, display, GPS, Bluetooth, Wi-Fi, vibration motor and other components.

In some implementations, heuristic process 120 can make settings recommendations to control multiplexer 124. For example, control multiplexer 124 can be a process that arbitrates between component settings provided by heuristic processes 120 and other processes and/or functions of mobile device 100 that influence or change the settings of the components of mobile device 100. For example, thermal daemon 110 can be a heuristics process that is configured to make adjustments to CPU power, display brightness, baseband processor power and other component settings based on detecting that the mobile device 100 is in the middle of a thermal event (e.g., above a threshold temperature). However, heuristic process 120 can be configured to make adjustments to CPU power, display brightness, baseband processor power and other component settings as well. Thus, in some implementations, heuristic process 120 and thermal daemon 110 can make settings adjustment recommendations to control multiplexer 124 and control multiplexer 124 can determine which settings adjustments to make. For example, control multiplexer 124 can prioritize processes and perform adjustments based on the priority of the recommending process. Thus, if thermal daemon 110 is a higher priority process than heuristic process 120, control multiplexer 124 can adjust the settings of the CPU, display, baseband processor, etc. according to the recommendations of thermal daemon 110 instead of heuristic process 120.

In some implementations, a mobile device 100 can be configured with multiple heuristic processes 120. The heuristic processes 120 can be configured or reconfigured over the air. For example, the parameters (e.g., triggers, threshold values, criteria, and output) of each heuristic process 120 can be set or adjusted over the network (e.g., cellular data connection, Wi-Fi connection, etc.). In some implementations, new heuristic processes 120 can be added to mobile device 100. For example, over time new correlations between trigger events, statistical data and device settings can be determined by system developers. As these new correlations are identified, new heuristic processes 120 can be developed to adjust system settings to account for the newly determined relationships. In some implementations, new heuristic processes 120 can be added to mobile device 100 over the network. For example, the new heuristic processes 120 can be downloaded or installed on mobile device 100 over the air (e.g., cellular data connection, Wi-Fi connection, etc.).

Example Heuristic Processes

In some implementations, a heuristic process 120 can be configured to adjust system settings of the mobile device 100 to prevent the mobile device 100 from getting too hot when in the user's pocket. For example, this hot-in-pocket heuristic process can be configured to register with sampling daemon 102 to be invoked when the mobile device's display is off (e.g., "system.backlight" event has an attribute value of zero/false) and when the mobile device 100 is not playing any entertainment media (e.g., music, movies, video, etc.). When invoked, the hot-in-pocket heuristic can make recommendations to reduce CPU power and GPU power to reduce the operating temperature of mobile device 100, for example.

In some implementations, heuristic process 120 can be configured to adjust location accuracy when the mobile device's display is not being used (e.g., "system.backlight" event has an attribute value of zero/false). For example, if the mobile device's display is not being used (e.g., the display is turned off, as indicated by the "backlight" attribute event described above), the mobile device 100 cannot display map information or directions to the user. Thus, the user is not likely using the location services of the mobile device 100 and the location services (e.g., GPS location, Wi-Fi location, cellular location, etc.) can be adjusted to use less power. The location accuracy heuristic process can register with sampling daemon 102 to be invoked when the mobile device's display is off. When invoked, the heuristic process can adjust the power levels of the GPS processor, Wi-Fi transmitter, cellular transmitter, baseband processor or terminate processes used to determine a location of the mobile device 100 in order to conserve the energy resources of mobile device 100.

In some implementations, a heuristic process 120 can be configured to adjust the settings of the mobile device's ambient light sensor in response to the user's behavior. For example, this user-adaptive ambient light sensor (ALS) heuristic process can be invoked by sampling daemon 102 when sampling daemon 102 receives data (e.g., an "ALS" attribute event) indicating that the ambient light sensor has detected a change in the ambient light surrounding mobile device 100, that the ambient light sensor system has adjusted the brightness of the display and/or that the user has provided input to adjust the brightness of the display.

When invoked, the user-adaptive ALS heuristic can request additional information from sampling daemon 102 with respect to ALS display adjustments and user initiated display adjustments to determine if there is a pattern of user input that indicates that when the ALS adjusts the display brightness up or down and the user adjusts the display brightness in the opposite direction (e.g., a "system.ALS" event followed by a "system.backlight" event). For example, the user may ride the bus or the train to work. The bus lights may be turned on and off during the ride. The ambient light sensor can detect the change in ambient light and increase the display brightness when the lights come on. Since the lights only come on temporarily, the user may decrease the display brightness when the lights turn off again. This pattern of user input can be tracked (e.g., through "backlight" attribute events) and correlated to time of day, calendar or alarm event entry, or travel pattern by the heuristic process to determine under what circumstances or context the user adjusts the display brightness in response to an ALS display adjustment. Once the user-adaptive ALS heuristic process determines the pattern of input and context, the heuristic process can adjust the settings of the ALS to be more or less aggressive. For example, the ALS can be adjusted to check the level of ambient light more or less frequently during the determined time of day, calendar or alarm entry, or travel pattern and adjust the display brightness accordingly.

The above heuristic processes are a few examples of heuristic processes and how they might be implemented in the system described herein. Other heuristic processes can be implemented and added to the system as they are developed over time. For example, additional heuristic processes can be configured or programmed to adjust CPU, GPU, baseband processors or other components of the mobile device in response to detecting events or patterns of events related to temperature measurements, user input, clock events (e.g., alarms), calendar events and/or other events occurring and detected on the mobile device.

Example Heuristic Registration and Invocation Processes

Figure 2:
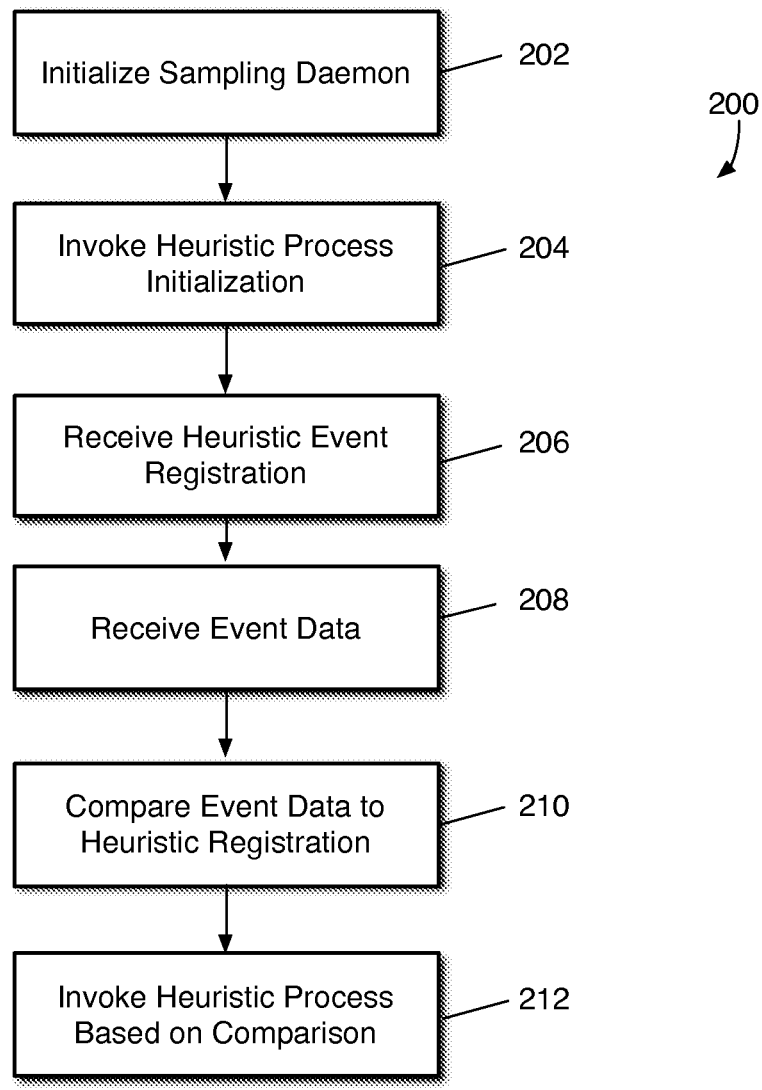
FIG. 2 illustrates an example process for invoking heuristic processes.

FIG. 2 illustrates an example process 200 for invoking heuristic processes. At step 202, the sampling daemon 102 can be initialized. For example, sampling daemon 102 can be initialized during startup of the mobile device 100.

At step 204, the sampling daemon 102 can invoke the heuristic processes configured on the mobile device 100 during initialization of the sampling daemon 102. For example, sampling daemon 102 can cause each heuristic process 120 to execute on mobile device 100 and run through their initialization subroutines.

At step 206, the sampling daemon 102 can receive event registration messages from each heuristic process 120. For example, during the initialization subroutines of the heuristic processes 120, the heuristic processes 120 can send information to sampling daemon 102 indicating which attribute events should trigger an invocation of heuristic process 120. Sampling daemon 102 can store the registration information in a database, such as event data store 104, for example. The registration information can include an identification of the heuristic process (e.g., executable name, file system path, etc.) and event criteria (identification of attributes, attribute values, threshold, ranges, etc.) so that sampling daemon 102 can call the heuristic process 120 when the specified event is detected.

At step 208, the sampling daemon 102 can receive attribute event data. For example, sampling daemon 102 can receive attribute event data from various system components, including the application manager 106, sensors 114, calendar 116 and clock 118, as described above.

At step 210, the sampling daemon 102 can compare the received attribute event data to the heuristic registration data. For example, as attribute event data is reported to sampling daemon 102, sampling daemon 102 can compare the event data (e.g., attribute values), or the statistics generated from the event data, to the registration information received from the heuristic processes 120.

At step 212, the sampling daemon 102 can invoke a heuristic process based on the comparison performed at step 210. For example, if the event data (e.g., attribute data) and/or statistics, meet the criteria specified in the heuristic registration data for a heuristic process 120, then the sampling daemon 102 can invoke the heuristic process 120. For example, if the event data and/or statistics data cross some threshold value specified for an event by the heuristic process during registration, then the heuristic process can be invoked by sampling daemon 102. Alternatively, the mere occurrence of a particular attribute event can cause invocation the heuristic process 120.

Figure 3:
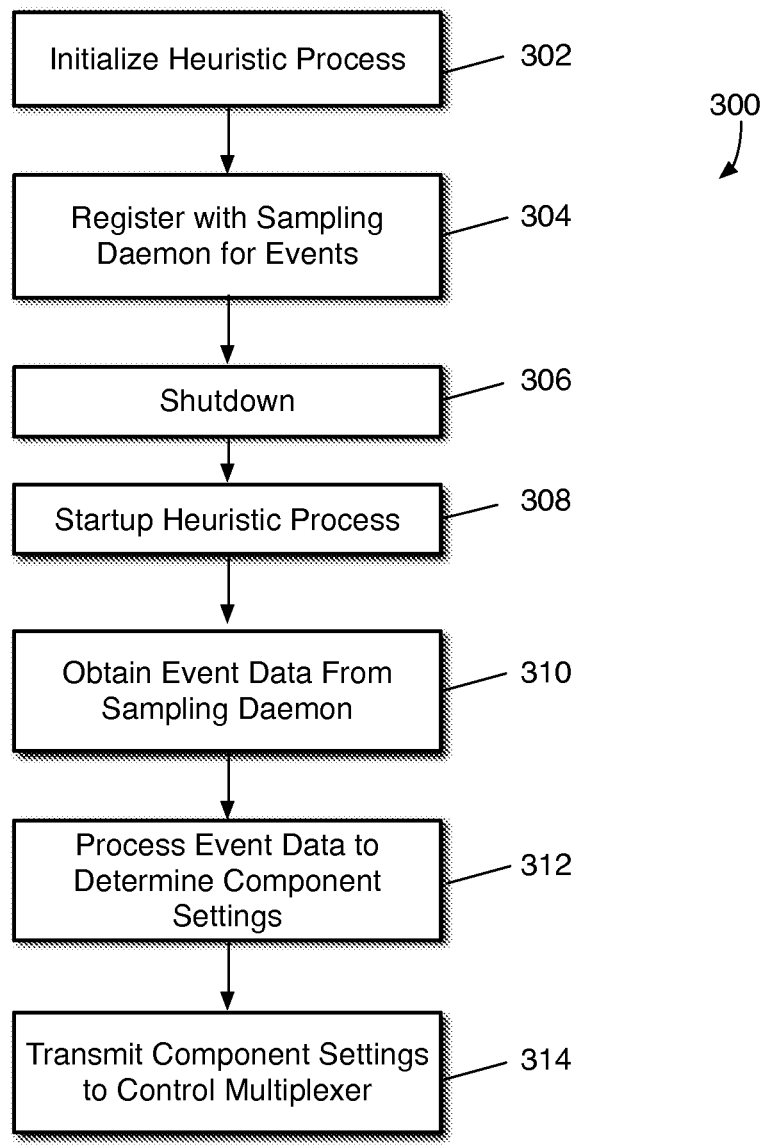
FIG. 3 illustrates a process for adjusting the settings of a mobile device using a heuristic process.

FIG. 3 illustrates a process 300 for adjusting the settings of a mobile device 100 using a heuristic process 120. At step 302, the heuristic process 120 is initialized. For example, the heuristic process 120 can be invoked by sampling daemon 102 so that the heuristic process 120 can run through its initialization subroutines. For example, the invocation can be parameterized to indicate that the heuristic process 120 should run through its initialization subroutines during this invocation.

At step 304, the heuristic process 120 can register with sampling daemon 102 for system events. For example, during initialization, the heuristic process 120 can send a message to sampling daemon 102 that includes an identification of events, thresholds, attributes, attribute values or other criteria for invoking the heuristic process 120. When the event occurs and/or the criteria are met, sampling daemon 102 can invoke the heuristic process 120.

At step 306, the heuristic process 120 can shut down or terminate. For example, the heuristic process 120 is not needed by the system until the registration criteria are met for the heuristic process 120. Thus, to conserve device resources (e.g., battery power, processing power, etc.), the heuristic process 120 is terminated, shutdown or suspended until it is needed (e.g., triggered by sampling daemon 102).

At step 308, the heuristic process 120 can be restarted. For example, sampling daemon 102 can invoke the heuristic process 120 when sampling daemon 102 determines that the criteria specified by the heuristic process 120 in the registration message have been met.

At step 310, the heuristic process 120 can obtain event data from sampling daemon 102. For example, once restarted, the heuristic process 120 can query sampling daemon 102 for additional attribute event data. The heuristic process 120 can be configured to interact with other system resources, processes, sensors, etc. to collect data, as needed.

At step 312, the heuristic process 120 can process event data to determine component settings. For example, the heuristic process 120 can use the event data and/or statistics from the sampling daemon 102 and/or the data collected from other components of the system to determine how to adjust the settings of various components of the mobile device 100. For example, if heuristic process 120 determines that mobile device 100 is too hot, heuristic process 120 can determine which power settings of mobile device 100 will reduce the operating temperature of mobile device 100.

At step 314, the heuristic process 120 can transmit the determined component settings to the control multiplexer 124. For example, the control multiplexer 124 can arbitrate device settings recommendations received from the heuristic process 120 and other system components (e.g., thermal daemon 110). The control multiplexer 124 can then adjust various components (e.g., CPU, GPU, baseband processor, display, etc.) of the mobile device 100 according to the received settings recommendations.

Forecasting Events

In some implementations, attribute event data stored in event data store 104 (e.g., historical data) can be used by sampling daemon 102 to predict the occurrence of future events. For example, "bundleId" attribute events can be analyzed to predict when a user will invoke applications (e.g., any application or a specific application). The "mailapp.mailbox" event that specifies a particular email folder (e.g., "mailbox" attribute value set to "work" folder) can be analyzed to predict when a user will use a particular email folder of the "mailapp" application.

Event History Window Specification

In some implementations, an event forecast can be generated based on an event history window specification. For example, the window specification can be generated by a client to specify a time period of interest, or recurring time period of interest, upon which the client wishes to base an event forecast. The window specification can include four components: a start time, an end time, a recurrence width, and a recurrence frequency. The start time can indicate the date and/or time in history when the window should start. The end time can indicate the date and/or time in history when the window should end. The recurrence width can indicate a block of time (e.g., four hours starting at the start time) that is of interest to a client. The recurrence frequency can indicate how frequently the block of time should be repeated starting at the start time (e.g., every 8 hours, every two days, every week, every two weeks, etc.).

In some implementations, only the events that occur within the specified block of time (e.g., time period of interest) will be analyzed when generating an event forecast. For example, if the current date is May 13, 2014, a window specification can specify a start date of May 11, 2014 at 12:00 pm, an end date of May 12 at 12 pm, a recurrence width of 1 hour, and a recurrence frequency of 4 hours. This window specification will cause the sampling daemon 102 to analyze event data within each 1 hour block (e.g., time period of interest) that occurs every 4 hours starting on May 11, 2014 at 12:00 pm and ending on May 12, 2014 at 12:00 pm (e.g., block 1: May 11, 2014 at 12:00-1:00 pm; block 2: May 11, 2014 at 4:00-5:00 pm; block 3: May 11, 2014 at 8:00-9:00 pm, etc.). In some implementations, when no recurrence width is specified, the entire time period from the start time to the end time will be analyzed to forecast events.

In some implementations, sampling daemon 102 can automatically generate an event history window specification. For example, sampling daemon 102 can identify patterns in the event history data stored in event data store 104. If a client requests a forecast for "bundleId" events but does not provide a window specification, sampling daemon 102 can, for example, identify a pattern for the "bundleId" attribute/event that indicates that applications are typically invoked by the user at 8:00-9:00 am, 11:30 am-1:30 pm, and 7:00-11:00 pm. Sampling daemon 102 can automatically generate a window specification that includes those time periods and excludes other times of day so that a requested forecast will focus on time periods that are relevant to the requested attribute. Similarly, sampling daemon 102 can automatically generate an event history window specification for a particular (e.g., specified) attribute value. For example, if the client requests a forecast for "bundleId" events having an attribute value of "mailapp," then sampling daemon 102 can analyze the event history data to identify patterns of occurrences related to the "mailapp" value. If the "mailapp" "bundleId" attribute value is recorded in the event history data every day at 10:00 am, 12:00 pm and 5:00 pm, then sampling daemon 102 can generate a window specification that specifies time periods of interest around those times of day.

Temporal Forecasts

In some implementations, a temporal forecast can be generated for an attribute or attribute value. The temporal forecast can indicate, for example, at what time of day an event associated with the attribute or attribute value is likely to occur. For example, a client of sampling daemon 102 can request a temporal forecast for the "bundleId" attribute (e.g., application launches) over the last week (e.g., last 7 days). To generate the forecast, a 24-hour day can be divided into 96 15-minute timeslots. For a particular timeslot (e.g., 1:00-1:15 pm) on each of the last seven days, the sampling daemon 102 can determine if a "bundleId" event occurred and generate a score for the timeslot. If the "bundleId" event occurred during the particular timeslot in 2 of the 7 days, then the likelihood (e.g., score) that the "bundleId" event will occur during the particular timeslot (e.g., 1:00-1:15 pm) is 0.29 (e.g., 2 divided by 7). If the "bundleId" event occurred during a different timeslot (e.g., 12:15-12:30 pm) on 4 of the 7 days, then the likelihood (e.g., score) that the "bundleId" event will occur during that timeslot is 0.57 (e.g., 4 divided by 7).

Similarly, a client can request a temporal forecast for a particular attribute value. For example, instead of requesting a temporal forecast for the "bundleId" attribute (e.g., "bundleId" event), the client can request a temporal forecast for "bundleId" events where the "bundleId" attribute value is "mailapp". Thus, the client can receive an indication of what time (e.g., 15-minute time-slot) of day the user will likely invoke the "mailapp" application.

In some implementations, the temporal forecast can be generated based on an event history window specification. For example, if the client provides a window specification that specifies a 4-hour time period of interest, the temporal forecast will only generate likelihood scores for the 15-minute timeslots that are in the 4-hour time period of interest. For example, if the time period of interest corresponds to 12:00-4:00 pm for each of the last 3 days, then 16 timeslots will be generated during the 4 hour period of interest and a score will be generated for each of the 16 15 minute timeslots. Scores will not be generated for timeslots outside the specified 4 hour time period of interest.

Peer Forecasts

In some implementations, sampling daemon 102 can generate peer forecasts for attributes. For example, a peer forecast can indicate the relative likelihoods of values for an attribute occurring during a time period of interest relative to all values (e.g., occurrences) of the same attribute. For example, a client of sampling daemon 102 can request a peer forecast of the "bundleId" attribute over a time period of interest (e.g., 11:00 am-1:00 pm) as specified by a window specification submitted with the request. If, during the time period of interest, "bundleId" events having attribute values "mailapp," "contacts," "calendar," "webbrowser," "mailapp," "webbrowser," "mailapp" occur, then the relative likelihood (i.e., score) of "mailapp" occurring is 0.43 (e.g., 3/7), the relative likelihood of "webbrowser" occurring is 0.29 (e.g., 2/7) and the relative likelihoods for "contacts" or "calendar" occurring is 0.14 (e.g., 1/7).

In some implementations, a client of sampling daemon 102 can request a peer forecast for an attribute. For example, if a client requests a peer forecast for an attribute without specifying a value for the attribute, then sampling daemon 102 will generate a peer forecast and return the various probability scores for all values of the attribute within the time period of interest. Using the example peer forecast above, sampling daemon 102 will return a list of attribute values and scores to the requesting client, for example: "mailapp":0.43; "webbrowser":0.29; "contacts":0.14; "calendar":0.14.

In some implementations, a client of sampling daemon 102 can request a peer forecast for an attribute value. For example, the client can request a peer forecast for the "bundleId" attribute having a value of "mailapp." Sampling daemon 102 can generate a peer forecast for the "bundleId" attribute according to the window specification provided by the client, as described above. For example, the sampling daemon 102 can calculate the relative likelihood (i.e., score) of "mailapp" occurring is 0.43 (e.g., 3/7), the relative likelihood of "webbrowser" occurring is 0.29 (e.g., 2/7) and the relative likelihoods for "contacts" or "calendar" occurring is 0.14 (e.g., 1/7). Sampling daemon 102 can return a score for the requested "mailapp" value (e.g., 0.43) to the client. If the requested value is not represented in the time period of interest as specified by the window specification, then a value of zero will be returned to the client.

Panorama Forecasts

In some implementations, a panorama forecast can be generated to predict the occurrence of an attribute event. For example, the temporal and peer forecasts described above use the relative frequency of occurrence of events for a single attribute or attribute value to predict future occurrences of that attribute. This "frequency" forecast type (e.g., frequency of occurrence) uses only the data associated with the attribute or attribute value specified in the forecast request. In contrast, a "panorama" forecast can use other data (e.g., location data, beacon data, network quality, etc.) in the event data received for the attribute or attribute value specified in the forecast request. In some implementations, a panorama forecast can use data from events associated with other attributes or attribute values. For example, when a client requests a temporal forecast or a peer forecast for a specified attribute or attribute value and also specifies that the forecast type (i.e., forecast flavor) is panorama, sampling daemon 102 will analyze event data for the specified attribute or attribute value and event data for other attributes and attribute value to identify correlations between the specified event and other events received by sampling daemon 102. For example, a frequency forecast for attribute "bundleId" having a value "mailapp" might assign a score of 0.4 to the 9:00 am 15-minute timeslot. However, a panorama forecast might determine that there is a strong correlation between the "mailapp" attribute value and the user's work location. For example, a panorama forecast might determine that if the user is at a location associated with work, the mailapp is invoked 90% of the time in the 9:00 am 15-minute timeslot. Thus, sampling daemon 102 can assign a higher score (e.g., 0.9) to the "mailapp" forecast score for the 9:00 am 15-minute timeslot.

Similarly, sampling daemon 102 might find a strong correlation between the "mailapp" "bundleId" attribute value and an occurrence of an event associated with the "motionState" attribute value "stationary." For example, sampling daemon 102 can determine that the correlation between use of the mailapp application and mobile device 100 being stationary is 95%. Sampling daemon 102 can determine that the correlation between use of the mailapp and mobile device 100 being in motion is 5%. Thus, sampling daemon 102 can adjust the forecast score (e.g., 0.95 or 0.05) for the "mailapp" attribute value for a particular timeslot based on whether mobile device is moving or stationary.

Scoreboarding—Frequency vs. Panorama

In some implementations, sampling daemon 102 can keep track of which forecast type is a better predictor of events. For example, when sampling daemon 102 receives an attribute event, sampling daemon 102 can generate frequency and panorama forecasts for the attribute or attribute value associated with the received event and determine which forecast type would have been a better predictor of the received attribute event. Stated differently, sampling daemon 102 can determine whether the frequency forecast type or the panorama forecast type would have been a better predictor of the received attribute event if the forecasts were generated immediately before the attribute event was received.

In some implementations, sampling daemon 102 can maintain a scoreboard for each forecast type (e.g., default, panorama). For example, each time that sampling daemon 102 determines that the frequency forecast type would have been a better predictor for a received event, sampling daemon 102 can increment the score (e.g., a counter) for the frequency forecast type. Each time that sampling daemon 102 determines that the panorama forecast type would have been a better predictor for a received event, sampling daemon 102 can increment the score (e.g., counter) for the panorama forecast type.

In some implementations, sampling daemon 102 can determine a default forecast type based on the scores generated for each forecast type (e.g., frequency, panorama). For example, if the scoreboarding process generates a higher score for the panorama forecast type, then panorama will be assigned as the default forecast type. If the scoreboarding process generates a higher score for the frequency forecast type, then frequency will be assigned as the default forecast type. When a client requests a peer or temporal forecast, the client can specify the forecast type (e.g., panorama, frequency, default). If the client does not specify a forecast type, then the default forecast type will be used to generate peer and/or temporal forecasts.

Attribute Statistics

In some implementations, a client can request that sampling daemon 102 generate statistics for an attribute or an attribute value. For example, similar to forecast generation, a client can specify a history window over which statistics for an attribute or attribute value should be generated. The sampling daemon 102 will analyze attribute events that occur within the specified history window when generating statistics for the specified attribute or attribute value. The client request can specify which of the following statistics should be generated by sampling daemon 102.

In some implementations, sampling daemon 102 can generate a "count" statistic for an attribute or attribute value. For example, the "count" statistic can count the number of events associated with the specified attribute or attribute value that occur within the specified history window.

In some implementations, sampling daemon 102 can generate statistics based on attribute values. For example, a client can request and sampling daemon 102 can return the first value and/or the last value for an attribute in the specified history window. A client can request and sampling daemon 102 can return the minimum, maximum, mean, mode and standard deviation for all values associated with the specified attribute within the specified history window. The sampling daemon 102 can generate or determine which values are associated with requested percentiles (e.g., $10^{th}$, $25^{th}$, $50^{th}$, $75^{th}$, $90^{th}$, etc.)

In some implementations, sampling daemon 102 can generate duration statistics. For example, sampling daemon 102 can determine a duration associated with an attribute value by comparing an attribute's start event with the attribute's stop event. The time difference between when the start event occurred and when the stop event occurred will be the duration of the event. In some implementations, a client can request and sampling daemon 102 can return the minimum, maximum, mean, mode and standard deviation for all durations associated with the specified attribute or attribute value within the specified history window. The sampling daemon 102 can generate or determine which duration values are associated with requested percentiles (e.g., $10^{th}$, $25^{th}$, $50^{th}$, $75^{th}$, $90^{th}$, etc.)

In some implementations, sampling daemon 102 can generate event interval statistics. For example, sampling daemon 102 can determine a time interval associated with the arrival or reporting of an event associated with an attribute value by comparing a first occurrence of the attribute event with a subsequent occurrence of an attribute event. The time difference between when the first event occurred and when the subsequent event occurred will be the time interval between occurrences of the event. In some implementations, a client can request and sampling daemon 102 can return the minimum, maximum, mean, mode and standard deviation for all time interval values associated with the specified attribute or attribute value within the specified history window. The sampling daemon 102 can generate or determine which interval values are associated with requested percentiles (e.g., $10^{th}$, $25^{th}$, $50^{th}$, $75^{th}$, $90^{th}$, etc.).

Keep Applications Up To Date—Fetching Updates

Figure 4:
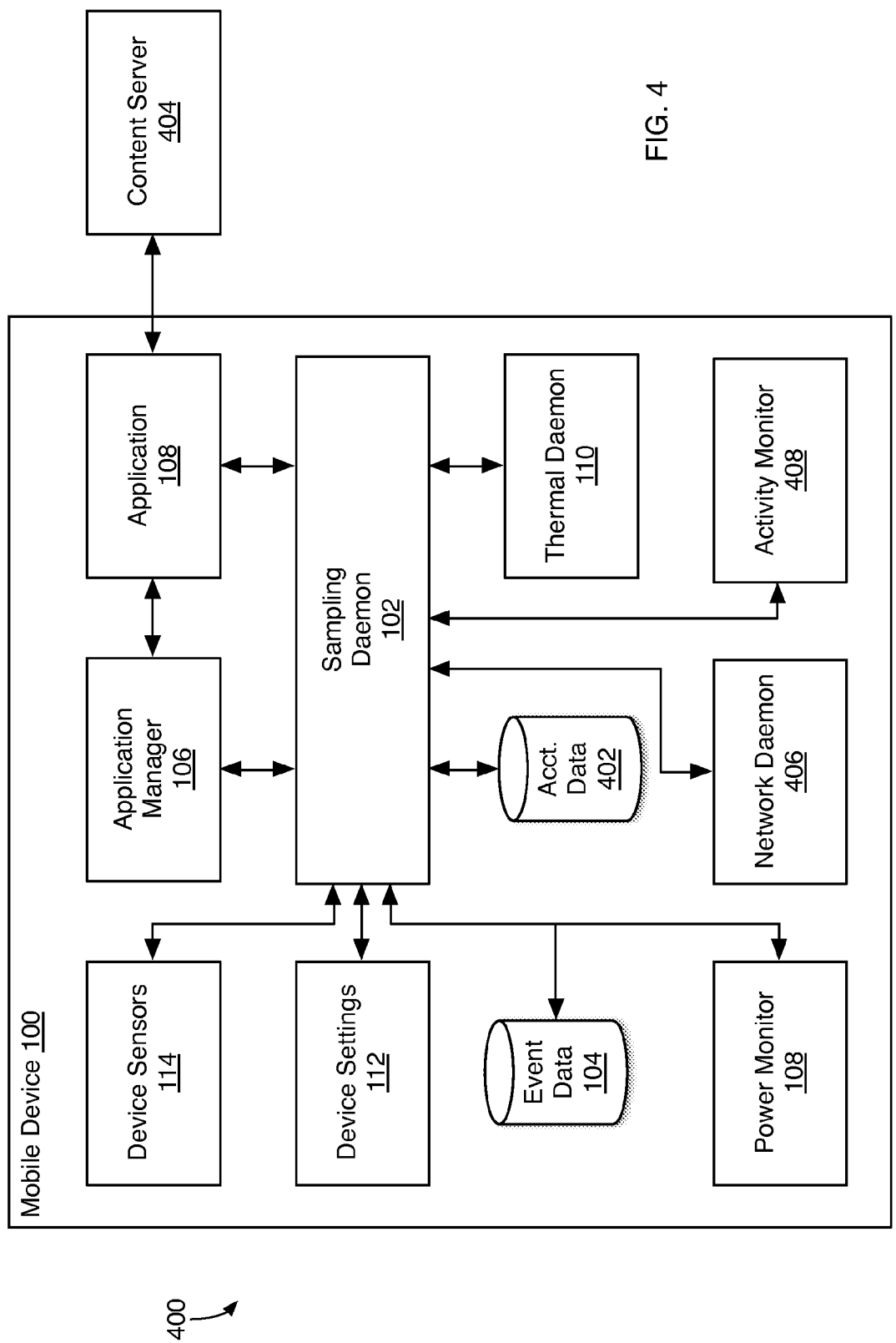
FIG. 4 illustrates an example system for performing background fetch updating of applications.

FIG. 4 illustrates an example system 400 for performing background fetch updating of applications. In some implementations, mobile device 100 can be configured to predictively launch applications as background processes of the mobile device 100 so that the applications can download content and update their interfaces in anticipation of a user invoking the applications. For example, the user application launch history data (e.g., "system.bundleId" start events) maintained by sampling daemon 102 can be used to forecast (predict) when the user will invoke applications of the mobile device 100. These predicted applications can be launched by the application manager 106 prior to user invocation so that the user will not be required to wait for a user invoked application to download current content and update the graphical interfaces of the applications.

Determining When to Launch
Applications—Temporal Forecasts

In some implementations, application manager 106 can request an application invocation forecast from sampling daemon 102. For example, sampling daemon 102 can provide an interface that allows the application manager 106 to request temporal forecast of application launches (e.g., "bundleId" start events) on mobile device 100. Sampling daemon 102 can receive events (e.g., "bundleId" start events) that indicate when the user has invoked applications on the mobile device 100, as described above. When application manager 106 requests a temporal forecast for the "bundleId" attribute, sampling daemon 102 can analyze the "bundleId" events stored in event data store 104 to determine when during the day (e.g., in which 15-minute timeslot) applications are typically invoked by the user. For example, sampling daemon 102 can calculate a probability that a particular time of day or time period will include an application invocation by a user using the temporal forecasting mechanism described above.

In some implementations, application manager 106 can request a temporal forecast for the "bundleId" attribute from sampling daemon 102 during initialization of the application manager 106. For example, application manager 106 can be invoked or launched during startup of mobile device 100. While application manager 106 is initializing, application manager 106 can request a temporal forecast of application invocations (e.g., "bundleId" start events) for the next 24 hours. Once the initial 24-hour period has passed, application manager 106 can request another 24-hour temporal forecast. This 24-hour forecast cycle can continue until the mobile device 100 is turned off, for example.

In some implementations, sampling daemon 102 can generate an application invocation (e.g., "bundleId" start event) temporal forecast for a 24-hour period. For example, sampling daemon 102 can divide the 24-hour period into 96 15-minute timeslots. Sampling daemon 102 can determine which applications have been invoked and at what time the applications were invoked over a number (e.g., 1 to 7) of previous days of operation based on the application launch history data (e.g., "bundleId" start event data) collected by sampling daemon 102 and stored in event data store 104.

In some implementations, when sampling daemon 102 generates a temporal forecast for the "bundleId" attribute, each 15-minute timeslot can be ranked according to a probability that an (e.g., any) application will be invoked in the 15-minute timeslot, as described above in the Temporal Forecast section.

Once the application invocation probabilities for each of the 96 timeslots is calculated, sampling daemon 102 can select a number (e.g., up to 64) of the timeslots having the largest non-zero probabilities and return information identifying the timeslots to application manager 106. For example, sampling daemon 102 can send application manager 106 a list of times (e.g., 12:00 pm, 1:45 pm, etc.) that correspond to the start of 15-minute timeslots that correspond to probable user invoked application launches (e.g., timeslots that have a score greater than zero).

In some implementations, application manager 106 can set timers based on the timeslots provided by sampling daemon 102. For example, application manager 106 can create or set one or more timers (e.g., alarms) that correspond to the timeslots identified by sampling daemon 102. When each timer goes off (e.g., at 12:00 pm), application manager 106 can wake (e.g., if sleeping, suspended, etc.) and determine which applications should be launched for the current 15-minute timeslot. Thus, the timers can trigger a fetch background update for applications that are likely to be invoked by a user within the corresponding timeslot.

In some implementations, other events can trigger a fetch background update for applications. For example, application manager 106 can register interest for various events with sampling daemon 102. For example, application manager 106 can register interest in events (e.g., attributes) related to turning on a cellular radio, baseband processor or establishing a network connection (e.g., cellular or Wi-Fi) so that application manager 106 can be notified when these events occur and can trigger a background application launch so that the application update can take advantage of an active network connection. Unlocking the mobile device 100, turning on the display and/or other interactions can trigger a background application launch and fetch update, as described further below. In some implementations, application manager 106 will not trigger a background application launch and fetch update if any background updates were performed within a previous number (e.g., seven) of minutes.

Determining What Applications to Launch—Peer Forecasts

In some implementations, application manager 106 can request that sampling daemon 102 provide a list of applications to launch for the current time. For example, when a timer goes off (e.g., expires) for a 15-minute timeslot or a triggering event is detected, application manager can request a peer forecast from sampling daemon 102 for the "bundleId" attribute so that sampling daemon 102 can determine which applications to launch for the current timeslot. Sampling daemon 102 can then generate peer forecasts that include a list of application identifiers and corresponding scores indicating the probability that each application will be invoked by the user at about the current time.

Figure 5:
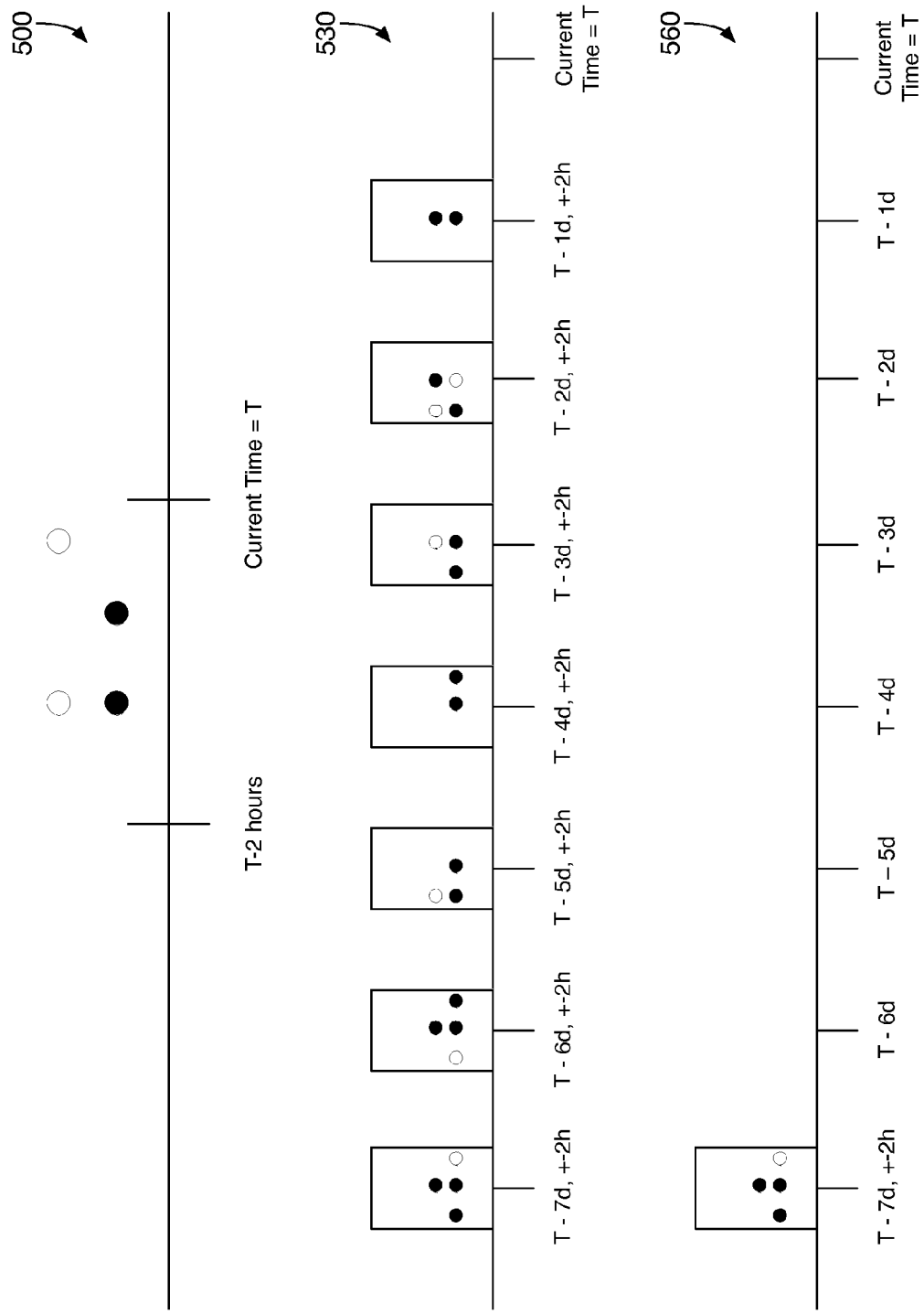
FIG. 5 illustrates peer forecasting for determining user invocation probabilities for applications on mobile device 100.

FIG. 5 illustrates peer forecasting for determining user invocation probabilities for applications on mobile device 100. For example, diagram 500 illustrates peer forecasting for a recent history window specification (e.g., previous 2 hours). Diagram 530 illustrates peer forecasting for a daily history window specification (e.g., 4 hour blocks every day for previous 7 days). Diagram 560 illustrates peer forecasting for a weekly history window specification (e.g., 4 hour block, once every 7 days). In some implementations, sampling daemon 102 can perform time series modeling using peer forecasts for different overlapping window specifications to determine the user invocation probabilities for applications on mobile device 100. If an application does not show up in the peer forecasts, the application can be assigned a zero probability value.

In some implementations, time series modeling can be performed by generating peer forecasts for different windows of time. For example, recent, daily and weekly peer forecasts can be generated by based on recent, daily and weekly event history window specifications. The recent, daily and weekly peer forecasts can then be combined to determine which applications to launch at the current time, as described further below.

In some implementations, user invocation probabilities can be generated based on recent application invocations. For example, user invocation probabilities can be generated by performing a peer forecast for the "bundleId" attribute with a window specification that specifies the previous two hours as the time period of interest (e.g., user initiated application launches within the last two hours).

As illustrated by diagram 500, application launch history data (e.g., "bundleId" event data) can indicate a number (e.g., four) of applications were launched in the previous two hours. For example, the dots and circles can represent applications where the empty circles can represent a single particular application (e.g., email, social networking application, etc.) and the empty circles represent invocations of other applications. The peer forecast probability score associated with the particular application using recent history (e.g., previous 2 hours) can be calculated by dividing the number of invocations of the particular application (e.g., 2)

by the total number of application invocations (e.g., 4) within the previous two hours. In the illustrated case, the probability associated with the particular application using recent application launch history data is 2/4 or 50%.

User invocation probabilities can be generated based on a daily history of application launches (e.g., which applications were launched at the current time+−2 hours for each of the previous seven days). For example, user invocation probabilities can be generated by performing a peer forecast for the "bundleId" attribute with a window specification that specifies the current time of day+−2 hours (e.g., 4 hour recurrence width) as the time period of interest (e.g., user initiated application launches within the last two hours) with a recurrence frequency of 24 hours (e.g., repeat the recurrence width every 24 hours).

Diagram 530 illustrates a daily history of application launches (e.g., "bundleId" start events) that can be used to determine a user invocation probability for an application. For example, each box of diagram 530 represents time windows (e.g., current time of day+−2 hours) in each of a number (e.g., 7) of previous days (e.g., as specified in the window specification of a peer forecast) that can be analyzed to determine the user invocation probability (e.g., peer forecast score) for a particular application (e.g., empty circle). The probability associated with the particular application using daily history data can be calculated by dividing the number of invocations of the particular application in all windows (e.g., 6) by the total number of application invocations in all windows (e.g., 22). In the illustrated case, the probability associated with the particular application using daily launch history data is 6/22 or 27%.

User invocation probabilities can be generated based on a weekly history of application launches (e.g., which applications were launched at the current time+−2 hours seven days ago). For example, user invocation probabilities can be generated by performing a peer forecast for the "bundleId" attribute with a window specification that specifies the current time of day+−2 hours (e.g., 4 hour recurrence width) as the time period of interest (e.g., user initiated application launches within the last two hours) with a recurrence frequency of 7 days (e.g., repeat the recurrence width every 7 days).

Diagram 560 illustrates a weekly history of application launches (e.g., "bundleId" start events) that can be used to determine a user invocation probability for an application. For example, if the current day and time is Wednesday at 1 pm, the user invocation probability (e.g., peer forecast score) for an application can be based on applications launched during the previous Wednesday during a time window at or around 1 pm (e.g., +−2 hours). In the illustrated case, the probability associated with the particular application (e.g., empty circle) using weekly application launch history data is 1/4 or 25%.

In some implementations, the recent, daily and weekly user invocation probabilities can be combined to generate a score for each application. For example, the recent, daily and weekly probabilities can be combined by calculating a weighted average of the recent (r), daily (d) and weekly (w) probabilities. Each probability can have an associated weight and each weight can correspond to an empirically determined predefined importance of each probability. The sum of all weights can equal one. For example, the weight for probability based on recent launches can be 0.6, the weight for the daily probability can be 0.3, and the weight for the weekly probability can be 0.1. Thus, the combined probability score can be the sum of 0.6(r), 0.3(d) and 0.1(w) (e.g., score=0.6r+0.3d+0.1w).

Referring back to FIG. 4, once the probability score is determined for each application based on the recent, daily and weekly probabilities, sampling daemon 102 can recommend a configurable number (e.g., three) of applications having the highest non-zero probability scores to the application manager 106 for launching to perform background fetch downloads/updates.

In some implementations, sampling daemon 102 can exclude from the "what to launch" analysis described above applications that do not support background updates (e.g., fetching) application updates, applications where the user has turned off background updates, applications that have opted out of background updates, and/or whichever application is currently being used by the user or is in the foreground on the display of the mobile device 100 since it is likely that the foreground application is already up to date.

In some implementations, once application manager 106 receives that recommended applications from sampling daemon 102, application manager 106 can ask sampling daemon 102 if it is ok to launch each of the recommended applications. Sampling daemon 102 can use its local admission control mechanism (described below) to determine whether it is ok for the application manager to launch a particular application. For example, application manager 106 can send the "bundleId" attribute with an attribute value that identifies one of the recommended applications to sampling daemon 102 and request that sampling daemon 102 perform admission control on the attribute value.

Local Admission Control

In some implementations, sampling daemon 102 can perform admission control for attribute events on mobile device 100. For example, admission control can be performed on an attribute or attribute value to determine whether a client application can perform an activity, action, function, event, etc., associated with the attribute. For example, a client of sampling daemon 102 can request admission of attribute "bundleId" having a value of "mailapp." In response to receiving the admission request, sampling daemon can determine whether the client can perform an activity associated with the "mailapp" attribute value (e.g., execute the "mailapp" application).

In some implementations, admission control can be performed based on budgets and feedback from voters. For example, when sampling daemon 102 receives an admission control request the request can include a cost associated with allowing the attribute event (e.g., launching an application, "bundleId" start event). Sampling daemon 102 can check a system-wide data budget, a system-wide energy budget and/or specific attribute budgets to determine whether the budgets associated with the attribute have enough credits remaining to cover the attribute event. If there is no budget associated with the attribute (e.g., the attribute is not a budgeted attribute), then the attribute event can be allowed to proceed (e.g., sampling daemon 102 will return an "ok" value in response to the admission control request). If there is a budget associated with the attribute and there is not enough credits left in the associated budget to cover the cost of the event, then the attribute event will not be allowed to proceed (e.g., sampling daemon 102 will return an "no" value in response to the admission control request).

If there is a budget associated with the attribute and there is enough credits left in the budget to cover the cost of the event, then the voters will be asked to vote on allowing the attribute to proceed. If all voters vote 'yes,' then the attribute event will be allowed to proceed (e.g., sampling daemon 102 will return an "ok" value in response to the admission control request). If any voter votes 'no,' then the attribute event will not be allowed to proceed (e.g., sampling daemon 102 will return an "no" value in response to the admission control request). Details regarding budgets and voters are described in the paragraphs below.

In some implementations, if an attribute or attribute value has not been reported in an event to sampling daemon 102 in a period of time (e.g., 7 days, one month, etc.) preceding the admission control request, then the sampling daemon 102 can return a "never" value in response to the admission control request. For example, sampling daemon 102 can generate a temporal or peer forecast to determine when to allow or admit an event associated with an attribute or attribute value. For example, there is no need to preempt an event that is not expected to occur (e.g., no need to prefetch data for applications that are not going to be invoked by the user).

Admission Control—Budgets

In some implementations, sampling daemon 102 can perform admission control based on budgets associated with attributes or attribute values. For example, sampling daemon 102 can determine whether to allow (e.g., admit) an activity (e.g., event) associated with an attribute or attribute value based on a budget associated with the attribute or attribute value. In some implementations, sampling daemon 102 can determine whether it is ok to admit an attribute or attribute value based on a system-wide energy budget and/or a system-wide data budget configured for mobile device 100. Sampling daemon 102 can store budget in accounting data store 402, including counters for keeping track of remaining data and energy budgets for the current time period (e.g., current hour). When a client requests admission control be performed for an attribute or attribute value, the client can specify a number representing the cost of allowing or admitting an event associated with the attribute or attribute value to occur. If there are enough credits in the budget associated with the attribute, then the attribute event will be voted on by the voters described below. If there are not enough credits in the budget associated with the attribute, then the attribute event will not be allowed to proceed.

System-Wide Energy Budget

In some implementations, sampling daemon 102 can determine whether it is ok to admit an attribute or attribute value based on an energy budget. For example, the energy budget can be a percentage (e.g., 5%) of the capacity of the mobile device's battery in milliamp hours.

In some implementations, the energy budget can be distributed among each hour in a 24-hour period. For example, sampling daemon 102 can utilize the battery utilization statistics (e.g., "system.energy" events) collected and stored in event data store 104 to determine a distribution that reflects a typical historical battery usage for each hour in the 24-hour period. For example, each hour can be assigned a percentage of the energy budget based on the historically or statistically determined energy use distribution or application usage forecast, as described above. Each hour will have at least a minimum amount of energy budget that is greater than zero (e.g., 0.1%, 1%, etc.). For example, 10% of the energy budget can be distributed among hours with no use data and the remaining 90% of the energy budget can be distributed among active use hours according to historical energy or application use. As each hour passes, the current energy budget will be replenished with the energy budget for the new/current hour. Any energy budget left over from a previous hour will be added to the current hour's budget.

In some implementations, accounting data store 402 can include a counter for determining how much energy budget remains available. For example, accounting data store 402 can include one or more counters that are initialized with the energy budget for the current hour. When the energy budget is used by an attribute event, the energy budget can be decremented by a corresponding amount. For example, application manager 106 can notify sampling daemon 102 when an application is launched or terminated using a "bundleId" start or stop event. In turn, sampling daemon 102 can notify power monitor 108 when an application is launched and when the application is terminated. Based on the start and stop times, power monitor 108 can determine how much energy was used by the application. Power monitor 108 can transmit the amount of power used by the application (e.g., by submitting a "system.energy" attribute event) to sampling daemon 102 and sampling daemon 102 can decrement the appropriate counter by the amount of power used.

In some implementations, when no energy budget remains for the current hour, sampling daemon 102 can decline the admission request for the attribute. For example, when the energy budget counters in accounting data store 402 are decremented to zero, no energy budget remains and no activities, events, etc., associated with attributes that are tied to the energy budget can be admitted. If enough energy budget remains for the current hour to cover the cost of the attribute event, sampling daemon 102 can return a "yes" value in response to the admission control request and allow the attribute event to proceed.

In some implementations, sampling daemon 102 will not base an admission control decision on the energy budget when the mobile device 100 is plugged into external power. For example, a remaining energy budget of zero will not prevent attribute events when the mobile device 100 is plugged into an external power source.

System-Wide Data Budget

In some implementations, sampling daemon 102 can determine whether it is ok to admit an attribute based on a data budget. For example, sampling daemon 102 can determine an average amount of network data consumed by the mobile device 100 based on statistical data (e.g., "system.networkBytes" attribute events) collected by sampling daemon 102 and stored in event data store 104. The network data budget can be calculated as a percentage of average daily network data consumed by the user/mobile device 100. Alternatively, the network data budgets can be predefined or configurable values.

In some implementations, the network data budgets can be distributed among each hour in a 24-hour period. For example, each hour can be allocated a minimum budget (e.g., 0.2 MB). The remaining amount of the network data budget can be distributed among each of the 24 hours according to historical network data use. For example, sampling daemon 102 can determine based on historical statistical data (e.g., "system.networkBytes" attribute events) how much network data is consumed in each hour of the day and assign percentages according to the amounts of data consumed in each hour. As each hour passes, the current data budget will be replenished with the data budget for the new/current hour. Any data budget left over from a previous hour can be added to the current hour's data budget.

In some implementations, accounting data store 402 can maintain data counters for network data budgets. As network data is consumed, the data counters can be decremented according to the amount of network data consumed. For example, the amount of network data consumed can be determined based on application start and stop events (e.g., "bundleId" start or stop events) provided to sampling daemon 102 by application manager 106. Alternatively, the amount of network data consumed can be provided by a process managing the network interface (e.g., network daemon 406, background transfer daemon 1302). For example, the network interface managing process can report "system.networkBytes" events to sampling daemon 102 that can be correlated to application start and stop events (e.g., "bundleId" events) to determine how much data an application consumes.

In some implementations, sampling daemon 102 can keep track of which network interface type (e.g., cellular or Wi-Fi) is used to consume network data and determine the amount of network data consumed based on the network interface type. The amount of network data consumed can be adjusted according to weights or coefficients assigned to each interface type. For example, network data consumed on a cellular data interface can be assigned a coefficient of one (1). Network data consumed on a Wi-Fi interface can be assigned a coefficient of one tenth (0.1). The total network data consumed can be calculated by adding the cellular data consumed to Wi-Fi data consumed divided by ten (e.g., total data=1*cellular data+0.1*Wi-Fi). Thus, data consumed over Wi-Fi will impact the data budget much less than data consumed over a cellular data connection.

In some implementations, when no data budget remains for the current hour, sampling daemon 102 can respond with a "no" reply to the admission control request. For example, when the data budget counters in accounting data store 402 are decremented to zero, no data budget remains and no activities associated with attributes that are tied to the data budget will be allowed. If there is enough remaining data budget in the current hour to cover the data cost of the attribute event, then sampling daemon 102 can respond with a "yes" reply to the admission control request.

Attribute Budgets

In some implementations, an attribute can be associated with a budget. For example, a predefined attribute or custom (dynamically defined) attribute can be associated with a budget through an API of the sampling daemon 102. A client (e.g., application, utility, function, third party application, etc.) of the sampling daemon 102 can make a request to the sampling daemon 102 to associate an attribute with a client-defined budget. The budget can be, for example, a number of credits.

Once the budget is allocated, reported events associated with the budgeted attribute can indicate a cost associated with the event and the budget can be decremented according to the specified cost. For example, a predefined system attribute "system.btlescan" can be configured on mobile device 100 to indicate when the mobile device 100 performs scans for signals from other Bluetooth low energy devices. The Bluetooth LE scan can be run as a background task, for example. The Bluetooth LE scan requires that the Bluetooth radio be turned on which, in turn, consumes energy from the battery of mobile device 100. To prevent the Bluetooth LE scan from consuming too much energy, the "btlescan" attribute can be assigned a budget (e.g., 24 credits). Every time a "btlescan" event is generated and reported to sampling daemon 102, the event can be reported with a cost (e.g., 1). The cost can be subtracted from the budget so that every time the "btlescan" attribute is reported in an event the budget of 24 is decremented by 1.

In some implementations, the attribute budget can be distributed over a time period. For example, the "btlescan" attribute budget can be distributed evenly over a 24 hour period so that the "btlescan" attribute can only spend 1 credit per hour. In some implementations, the attribute budget can be replenished at the end of a time period. For example, if the period for the "btlescan" attribute budget is 24 hours, then the "btlescan" attribute budget can be replenished every 24 hours.

In some implementations, a budget associated with an attribute can be a can be a subset (e.g., sub-budget) of another budget. For example, a budget for an attribute can be specified as a portion of another budget, such as the system-wide data or system-wide energy budgets described above. For example, the "mailapp.mailbox" attribute can be associated with a budget that is 5% of the data budget allocated for the system. The "btlescan" attribute can be associated with a budget that is 3% of the energy budget allocated for the system. The sub-budget (e.g., "mailbox" budget) can be tied to the super-budget (e.g., system data budget) such that decrementing the sub-budget also decrements the super-budget. In some implementations, if the super-budget is reduced to zero, then the sub-budget is also reduced to zero. For example, if the system data budget is at zero, the "mailbox" attribute budget will also be zero even if the no events have been reported for the "mailbox" attribute that would decrement the "mailbox" attribute budget.

In some implementations, sampling daemon 102 clients can request that the sampling daemon 102 return the amount of budget left for an attribute. For example, a client can make a request to the sampling daemon 102 for the budget remaining for the "btlescan" attribute. If three of 24 budgeted credits have been used, then sampling daemon 102 can return the value 21 to the requesting client.

In some implementations, a client can report an event that costs a specified number of budgeted credits when no credits remain in the budget for the associated attribute. When sampling daemon 102 receives an event (e.g., "btlescan" event) that costs 1 credit when there are no credits remaining in the budget, sampling daemon 102 can decrement the budget (e.g., −1) and return an error to the client that reported the event. The error can indicate that the attribute has no budget remaining, for example.

Attribute Budget Shaping

In some implementations, the attribute budget can be distributed based on historical usage information. For example, as events are reported for a budgeted attribute, requests (e.g., events associated with a cost) to use the budget for the attribute can be tracked over time. If a budget of 24 is allocated for the "btlescan" attribute, for example, the budget can initially be allocated evenly across a 24-hour period, as described above. As events are reported over time for an attribute associated with the budget, sampling daemon 102 can analyze the reported events to determine when during the 24-hour period the events are most likely to occur. For example, sampling daemon 102 can determine that the "btlescan" event frequently happens around 8 am, 12 pm and 6 pm but rarely happens around 2 am. Sampling daemon 102 can use this event frequency information to shape the distribution of the "btlescan" atribute's budget over the 24-hour period. For example, sampling daemon can allocate two budget credits for each timeslot corresponding to 8 am, 12 pm and 6 pm and zero budget credits for the timeslot associated with 2 am.

Admission Control—Voters

In some implementations, sampling daemon 102 can perform admission control based on feedback from other software (e.g., plugins, utilities, applications, heuristics processes) running on mobile device 100. For example, other software can be configured to work with sampling daemon 102 as a voter for admission control. For example, several voters (e.g., applications, utilities, daemons, heuristics, etc.) can be registered with sampling daemon 102 to vote on admission control decisions. For example, sampling daemon 102 can be configured to interface with a voter that monitors the thermal conditions of mobile device 100, a voter that monitors CPU usage of mobile device 100 and/or a voter that monitors battery power level of mobile device 100. When sampling daemon 102 receives an admission control request, each voter (e.g., thermal, CPU and battery) can be asked to vote on whether the activity associated with the specified attribute should be allowed. When all voters vote 'yes', then the attribute will be admitted (e.g., the activity associated with the attribute will be allowed to happen). When a single voter votes 'no', then the attribute will not be admitted (e.g., the activity associated with the attribute will not be allowed). In some implementations, the voters can be configured as plugin software that can be dynamically (e.g., at runtime) added to sampling daemon 102 to provide additional functionality to the admission control system. In some implementations, the voters can use the temporal and peer forecasting mechanisms described above when determining whether to admit or allow an event associated with an attribute or attribute value.

Network Daemon

In some implementations, a network daemon 406 can be configured as an admission control voter. The network daemon 406 can be configured to use a voting API of sampling daemon 102 that allows the network daemon 406 to receive voting requests from sampling daemon 102 and provide voting (e.g., yes, no) responses to sampling daemon 102. For example, the network daemon 406 can receive a voting request from sampling daemon 102 that includes an attribute and/or attribute value. The network daemon 406 can indicate that sampling daemon 102 should not admit or allow an event associated with an attribute or attribute value when the mobile device 100 is connected to a voice call and not connected to a Wi-Fi network connection, for example. For example, to prevent background updating processes (e.g., fetch processes) from interfering with or reducing the quality of voice calls, the network daemon 406 will not allow events (e.g., "bundleId" start events) associated with launching a background updating process when the user is connected to a voice call and not connected to a Wi-Fi connection. Thus, network daemon 406 can return a "no" value in response to a voting request when the mobile device 100 is connected to a call and not connected to Wi-Fi.

In some implementations, the network daemon 406 can indicate that sampling daemon 102 should not allow or admit an attribute event when the mobile device 100 has a poor quality cellular network connection. A poor quality cellular connection can be determined when transfer rate and/or throughput are below predefined threshold values. For example, if the mobile device 100 has a poor quality cellular network connection and is not connected to Wi-Fi, the network daemon 406 can prevent admission or execution of an attribute event that will waste battery energy and cellular data by using the poor quality network connection (e.g., launching an application that will attempt to download or upload data over a poor cellular connection) by returning a "no" value when sampling daemon 102 makes a voter request.

In some implementations, when network daemon 406 does not have information that indicates poor network conditions or some other condition that will effect network data usage or system performance, network daemon 406 can vote "yes" on the admission of the requested attribute.

Thermal Daemon

In some implementations, a thermal daemon 110 application can be configured as an admission control voter. The thermal daemon 110 can be configured to use a voting API of sampling daemon 102 that allows the thermal daemon 110 to receive voting requests from sampling daemon 102 and provide voting (e.g., yes, no) responses to sampling daemon 102. For example, the thermal daemon can receive a voting request from sampling daemon 102 that includes an attribute and/or attribute value. The thermal daemon 110 can indicate that sampling daemon 102 should not admit or allow an event associated with an attribute or attribute value when the thermal daemon 110 has detected a thermal event. For example, the thermal daemon 110 can monitor the temperature of the mobile device 100 and report temperature values to sampling daemon 102 by generating events that include the "thermalLevel" attribute and corresponding temperature value.

In some implementations, when thermal daemon 110 determines that the temperature of mobile device 100 is above a threshold temperature value, thermal daemon 110 can prevent thermal daemon 102 from allowing attribute events that may increase the operating temperature of mobile device 100 further by returning a "no" value when sampling daemon 102 sends a request to thermal daemon 110 to vote on an attribute (e.g., "bundleId") event.

In some implementations, sampling daemon 102 will only ask for a vote from thermal daemon 110 when an abnormal thermal condition currently exists. For example, sampling daemon 102 can maintain a thermal condition value (e.g., true, false) that indicates whether the mobile device 100 is operating at normal thermal conditions. If the current thermal condition of mobile device 100 is normal, then the thermal condition value can be true, for example. If the current thermal condition of mobile device 100 is abnormal (e.g., too hot, above a threshold temperature), then the thermal condition value can be false. Initially, the thermal condition value can be set to true (e.g., normal operating temperatures). Upon detecting that operating temperatures have risen above a threshold temperature, thermal daemon 110 can send sampling daemon 102 an updated value for the thermal condition value that indicates abnormal operating temperatures (e.g., false). Once the mobile device 100 cools down to a temperature below the threshold temperature, thermal daemon 110 can update the thermal condition value to indicate normal operating temperatures (e.g., true).

When sampling daemon 102 receives an admission control request for an attribute, sampling daemon 102 can check the thermal condition value to determine whether to ask thermal daemon 110 to vote on admission (allowance) of the attribute event. If the thermal condition value indicates normal operating temperatures (e.g., value is true), sampling daemon 102 will interpret the thermal condition value as a "yes" vote from thermal daemon 110.

If the thermal condition value indicates an abnormal operating temperature (e.g., value is false), sampling daemon 102 will send the attribute and/or attribute value to thermal daemon 110 to allow the thermal daemon 110 to vote on the specific attribute or attribute value.

In some implementations, thermal daemon 110 can determine how to vote (e.g., yes, no) on attributes and/or attribute values based on the current thermal condition of the mobile device 100 and a peer forecast for the attribute. For example, thermal daemon 110 can request a peer forecast for the attribute from sampling daemon 102. Thermal daemon 110 can request a peer forecast for the current time by generating a window specification that includes the current time (e.g., +−1 hour, 2 hours, etc.) in the time period of interest. Thermal daemon 110 will receive a peer forecast from the sampling daemon 102 that indicates likelihood scores for each value of the attribute that appears in the time period of interest. For example, if thermal daemon 110 requests a peer forecast for the "bundleId" attribute, thermal daemon 110 can receive a list of "bundleId" values (e.g., application identifiers) and associated forecast (e.g., probability, likelihood) scores. For example, if, during the time period of interest, "bundleId" events having attribute values "mailapp," "contacts," "calendar," "webbrowser," "mailapp," "webbrowser," "mailapp" occur, then the relative likelihood (i.e., score) of "mailapp" occurring is 0.43 (e.g., 3/7), the relative likelihood of "webbrowser" occurring is 0.29 (e.g., 2/7) and the relative likelihoods for "contacts" or "calendar" occurring is 0.14 (e.g., 1/7). In some implementations, thermal daemon 110 can order the list of attribute values according to score (e.g., highest scores at top, lowest scores at bottom). For example, the ordered list for the above "bundleId" attribute values from top to bottom is: "mailapp;" "webbrowser;" "contacts;" and "calendar".

In some implementations, thermal daemon 110 can determine when to vote yes on an attribute value based on where an attribute value is in the ordered list. For example, if the attribute value under consideration by thermal daemon 110 is not in the peer forecast list received from sampling daemon 102, then the attribute value will receive a 'no' vote from thermal daemon 110. If the attribute value is in the peer forecast list and is below a threshold level (e.g., index) in the list (e.g., in the bottom 25% of attributes based on scores), then thermal daemon 110 will vote 'no' on the attribute. If the attribute value is in the peer forecast list and is above a threshold level in the list (e.g., in the top 75% of attributes based on scores), then thermal daemon 110 will vote 'yes' on the attribute. Once the vote is determined, thermal daemon 110 will return the 'yes' (e.g., true) or 'no' (e.g., false) vote to sampling daemon 102.

In some implementations, thermal daemon 110 can be configured with a maximum threshold level to avoid voting 'no' on all attribute values (e.g., so that some attribute events will occur). The maximum threshold level can be 50% (e.g., top 50% get a 'yes' vote, bottom 50% get a 'no' vote) of attribute values in the ordered peer forecast list. Thermal daemon 110 can, therefore, adjust the threshold level that separates attribute values that will receive a 'yes' vote from attribute values that will receive a 'no' vote from the 0% to 50% of the attribute values with the lowest scores.

In some implementations, the threshold level for determining 'yes' or 'no' votes can be proportional to the thermal level (e.g., temperature) of mobile device 100. For example, thermal daemon 110 can be configured with a maximum operating thermal level ($L_h$) and a normal operating level ($L_n$). Thermal daemon 110 can determine the current operating thermal level ($L_c$) and determine what percentile of the thermal range (e.g., $L_h$-$L_n$) the mobile device 100 is currently operating at (e.g., $L_c$-$L_n$/$L_h$-$L_n$=%). Thermal daemon 110 can use the calculated percentile to determine what portion of the 0-50% attribute values should receive a 'no' vote. For example, if the current operating thermal level is calculated to be 65% of the thermal range, then the bottom 32.5% of attribute values by peer forecast score will receive a 'no' vote from thermal daemon 110. Thus, the least important attribute values will receive a 'no' vote while the most important attribute values will receive a 'yes' vote. Referring back to the "bundleId" example above, if the ordered list for the above "bundleId" attribute values from top to bottom is: "mailapp;" "webbrowser;" "contacts;" and "calendar", then "calendar" would receive a 'no' vote and "mailapp," "webbrowser," and "contacts" would receive a 'yes' vote (e.g., "mailapp," "webbrowser," and "contacts" being the most used applications). For example, if application manager 106 has made an admission control request for the "bundleId" attribute to determine which applications to launch, then "mailapp," "webbrowser," and "contacts" applications would be launched and "calendar" application would not be launched.

As another example, thermal daemon 110 can be asked to vote on the "mailapp.mailbox" attribute. A peer forecast can be generated for "mailapp.mailbox" attribute values that produce an ordered list of mail folders that indicate the most frequently accessed folder to the least frequently accessed folder (e.g., "inbox;" "personal;" "work;" "family;" "spam;" and "trash"). If the bottom 32.5% of attribute values are to receive a 'no' vote, then "spam" and "trash" will receive a 'no' vote. For example, if the "mailbox" application made the admission control request for the "mailapp.mailbox" attribute to determine which folders to fetch email for, then the "mailapp" application will fetch email for the "inbox," "personal," "work," and "family" folders and not fetch email for the "spam" and "trash" folders. In some implementations, attributes or attribute values that have received a 'no' vote from thermal daemon 110 can be notified when the thermal condition value maintained by sampling daemon 102 is reset to indicate normal operating temperatures (e.g., true value). For example, sampling daemon 102 can store data that identifies clients, attributes and attribute values that have received a 'no' vote. Upon receiving an updated thermal condition value (e.g., true) from thermal daemon 110, sampling daemon 102 can send a notification to the clients that received a 'no' vote to prompt the client to attempt another admission control request for the previously rejected attribute or attribute value. In some implementations, clients can resend an admission control request without prompting from sampling daemon 102. For example, a client may have an internal timer that causes the client to retry the admission control request after a period of time has elapsed.

Activity Monitor

In some implementations, an activity monitor application 408 can be configured as an admission control voter. The activity monitor 408 can be configured to use a voting API of sampling daemon 102 that allows the activity monitor 408 to receive voting requests from sampling daemon 102 and provide voting (e.g., yes, no) responses to sampling daemon 102. For example, the activity monitor 408 can receive a voting request from sampling daemon 102 that includes an attribute and/or attribute value. The activity monitor 408 can indicate that sampling daemon 102 should not admit or allow an event associated with an attribute or attribute value when mobile device 100 is using more than a threshold amount (e.g., 90%) of memory resources or CPU resources. For example, if mobile device 100 is already running many applications or processes that are using most of the memory resources or CPU resources of the mobile device 100, launching additional applications in the background will likely reduce the performance of the mobile device 100 by using up remaining memory resources. Thus, when the activity monitor 408 determines that memory or CPU usage exceeds a threshold value (e.g., 75%), activity monitor 408 can prevent application manager 106 from launching additional applications by returning a "no" value when sampling daemon 102 sends a request to vote on a "bundleId" attribute event. If the activity monitor 408 determines that the memory and/or CPU resources of mobile device 100 are below the threshold usage amount, the activity monitor 408 can return a "yes" value in response to the vote request from sampling daemon 102.

Launching a Background Fetch Application

In some implementations, when application manager 106 makes an admission control request to sampling daemon 102 and receives a "yes" reply, application manager 106 can invoke or launch the identified application (e.g., as identified by the "bundleId" attribute value, application 108) in the background of the operating environment of mobile device 100. For example, the application 108 can be launched in the background such that it is not apparent to the user that application 108 was launched. The application 108 can then communicate over a network (e.g., the internet) with content server 404 to download updated content for display to the user. Thus, when the user subsequently selects application 108 (e.g., brings the application to the foreground), the user will be presented with current and up-to-date content without having to wait for application 108 to download the content from server 404 and refresh the application's user interfaces.

In some implementations, application manager 106 can be configured to launch background fetch enabled applications when the mobile device 100 is charging and connected to Wi-Fi. For example, sampling daemon 102 can determine when mobile device 100 is connected to an external power source (e.g., based on "cablePlugin" attribute events) and connected to the network (e.g., internet) over Wi-Fi (e.g., based on received events) and send a signal to application manager 106 to cause application manager 106 to launch fetch enabled applications that have been used within a previous amount of time (e.g., seven days).

Example Background Fetch Processes

Figure 6:
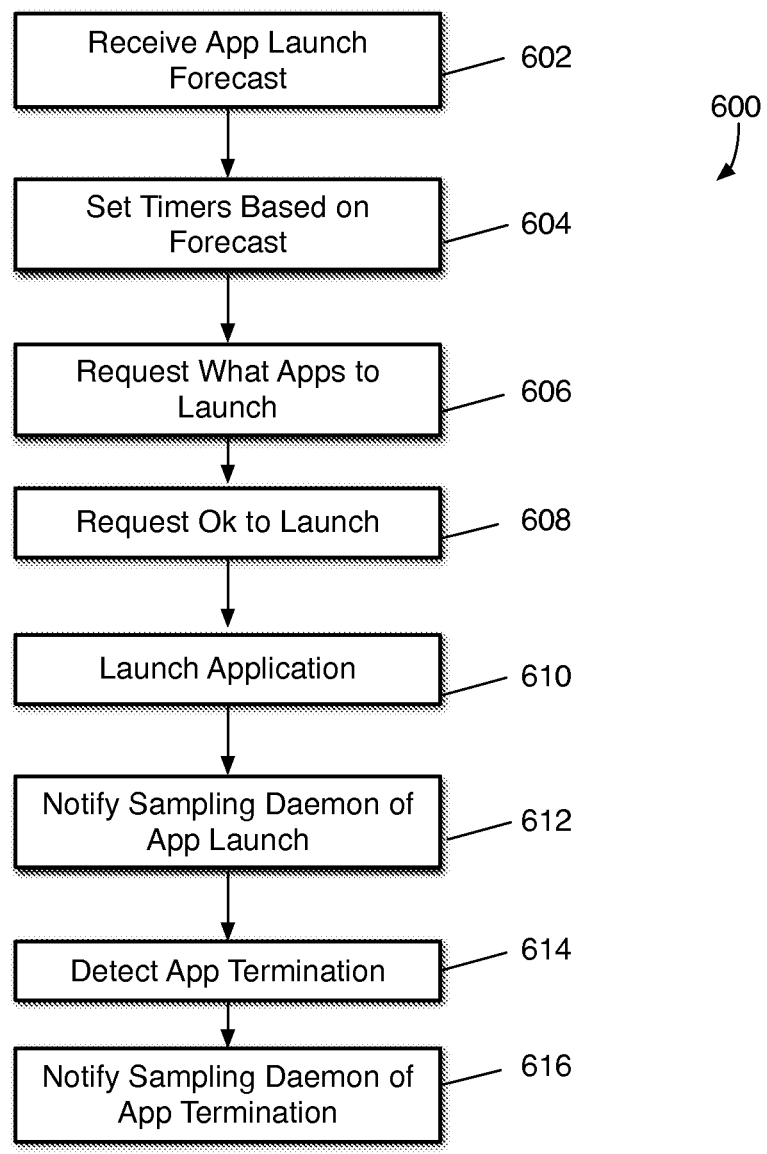
FIG. 6 is a flow diagram of an example process for predictively launching applications to perform background updates.

FIG. 6 is a flow diagram of an example process 600 for predictively launching applications to perform background updates. For example, process 600 can be performed by application manager 106 and sampling daemon 102 to determine when to launch background applications configured to fetch data updates from network resources, such as content server 404 of FIG. 4. Additional description related to the steps of process 600 can be found with reference to FIG. 4 and FIG. 5 above.

At step 602, application manager 106 can receive an application invocation forecast from sampling daemon 102. For example, application manager 106 can be launched during startup of mobile device 100. During its initialization, application manager 106 can request a forecast of applications likely to be invoked by a user of the mobile device 100 over the next 24-hour period. For example, application manager 106 can request a temporal forecast for attribute "bundleId." This forecast can indicate when to launch applications. For example, a 24-hour period can be divided into 15-minute blocks and each 15-minute block can be associated with a probability that the user will invoke an application during the 15-minute block. The forecast returned to application manager 106 can identify up to 64 15-minute blocks of time when the user is likely to invoke an application.

At step 604, application manager 106 can set timers based on the application launch forecast. For example, application manager 106 can set a timer or alarm for each of the 15 minute blocks identified in the application launch forecast returned to the application manager 106 by sampling daemon 102.

At step 606, application manager 106 can request sampling daemon 102 identify what applications to launch. For example, when a timer expires or alarm goes off, application manager can wake, if sleeping or suspended, and request from sampling daemon 102 a list of applications to launch for the current 15-minute block of time. Sampling daemon 102 can return a list of applications that should be launched in the background on mobile device 100. For example, application manager 106 can request a peer forecast for attribute "bundleId". The peer forecast can indicate which values of the "bundleId" attribute are most likely to be reported (e.g., which applications are most likely to be invoked by the user) in the current 15-minute timeslot.

At step 607, application manager 106 can send a request to sampling daemon 102 asking if it is ok to launch an application. For example, for each application identified by sampling daemon 102 in response to the "bundleId" peer forecast request, application manager 106 can ask sampling daemon 102 whether it is ok to launch the application. For example, application manager 106 can request that sampling daemon 102 perform admission control on a particular value of the "bundleId" attribute that corresponds to an application that application manager 106 is attempting to launch. Sampling daemon 102 can return "yes" from the admission control request if it is ok to launch the application, "no" if it is not ok to launch the application, or "never" if it is never ok to launch the application.

At step 610, application manager 106 can launch an application. For example, if sampling daemon 102 returns an "ok" (e.g., ok, yes, true, etc.) response to the admission control request, application manager 106 will launch the application as a background process of mobile device 100. If sampling daemon 102 returns a "no" or "never" response to the admission control request, application manager 106 will not launch the application.

At step 612, application manager 106 can transmit an application launch notification to sampling daemon 102. For example, application manager 106 can transmit a "bundleId" start event to sampling daemon 102 to record the execution of the launched application.

At step 614, application manager 106 can detect that the launched application has terminated. For example, application manager 106 can determine when the launched application is no longer running on mobile device 100.

At step 616, application manager 106 can transmit an application termination notification to sampling daemon 102. For example, application manager 106 can transmit a "bundleId" end event to sampling daemon 102 to record the termination of the application.

Figure 7:
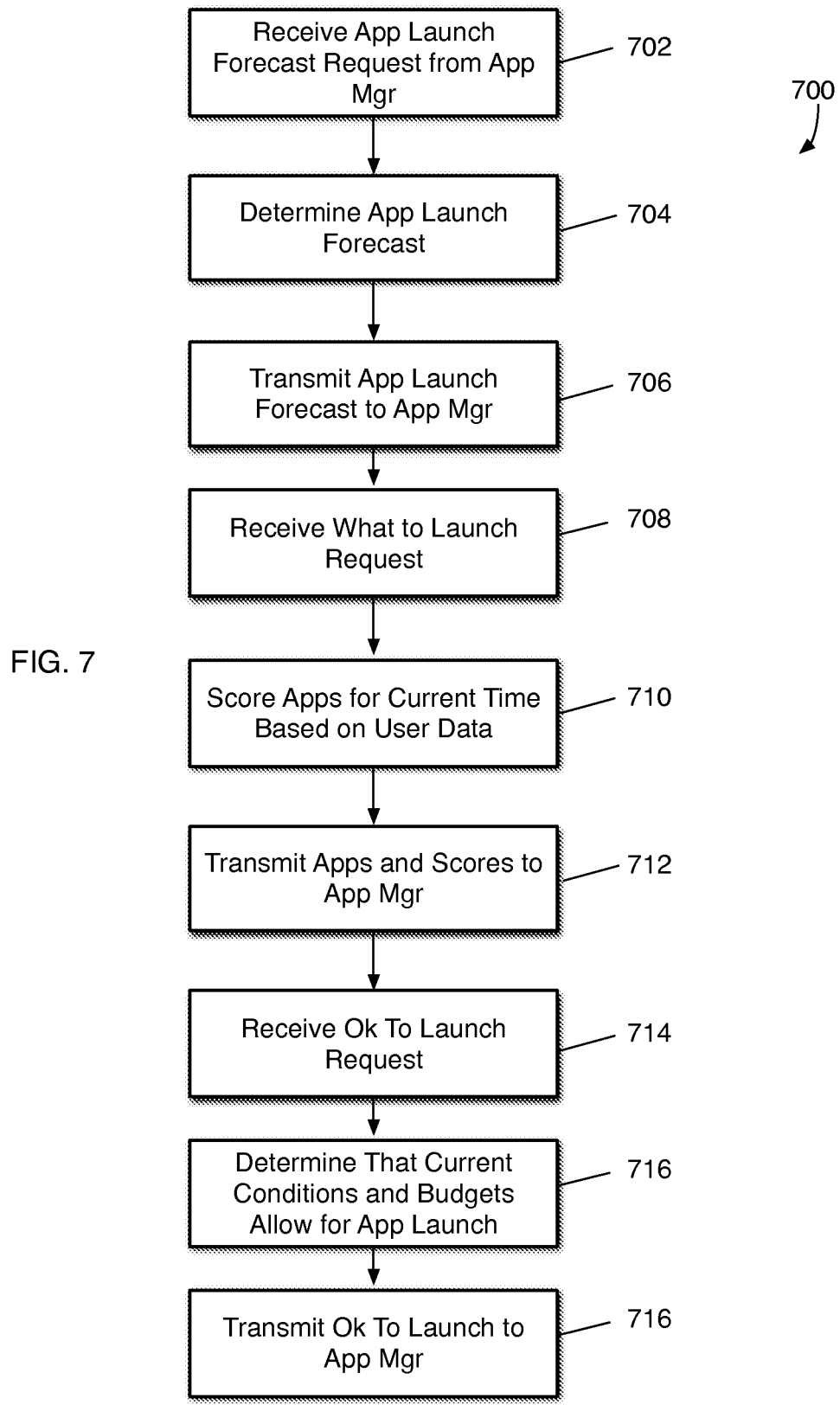
FIG. 7 is a flow diagram of an example process for determining when to launch applications on a mobile device.

FIG. 7 is a flow diagram of an example process 700 for determining when to launch applications on a mobile device 100. For example, process 700 can be used to determine when to launch applications, what applications should be launched and if it is ok to launch applications based on application use statistics (e.g., "bundleId" attribute event data), data and energy budgets, and mobile device operating and environmental conditions, as described above in detail with reference to FIG. 4

At step 702, sampling daemon 102 can receive an application launch forecast request from application manager 106. For example, application manager 106 can request a temporal forecast for the "bundleId" attribute for the next 24 hours from sampling daemon 102. Once the 24-hour period has passed, application manager 106 can request a temporal forecast for the "bundleId" attribute for the subsequent 24 hour period. For example, application manager 106 can request temporal forecast for the "bundleId" attribute every 24 hours.

At step 704, sampling daemon 102 can determine an application launch forecast. For example, the application launch forecast (e.g., temporal forecast for the "bundleId" attribute) can be used to predict when user-initiated application launches are likely to occur during a 24-hour period. The 24-hour period can be divided into 15-minute time blocks. For each 15-minute time block (e.g., there are 96 15-minute time blocks in a 24 hour period), sampling daemon 102 can use historical user invocation statistics (e.g., "bundleId" start events) to determine a probability that a user initiated application launch will occur in the 15-minute time block, as described above with reference to FIG. 4.

At step 706, sampling daemon 102 can transmit the application launch forecast to application manager 106. For example, sampling daemon 102 can select up to 64 15-minute blocks having the highest non-zero probability of a user initiated application launch. Each of the selected 15-minute blocks can be identified by a start time for the 15-minute block (e.g., 12:45 pm). Sampling daemon 102 can send the list of 15-minute block identifiers to application manager 106 as the application launch forecast (e.g., temporal forecast for the "bundleId" attribute).

At step 708, sampling daemon 102 can receive a request for what applications to launch at a current time. For example, application manager 106 can send a request to sampling daemon 102 for sampling daemon 102 to determine which applications should be launched at or around the current time. For example, the request can be a request for a peer forecast for the "bundleId" attribute for the current 15-minute timeslot.

At step 710, sampling daemon 102 can score applications for the current time based on historical event data. Sampling daemon 102 can determine which applications that the user is likely to launch in the near future based on historical user initiated application launch data (e.g., "bundleId" attribute start event data) collected by sampling daemon 102. Sampling daemon 102 can utilize recent application launch data, daily application launch data and/or weekly application launch data to score applications based on the historical likelihood that the user will invoke the application at or around the current time, as described above with reference to FIG. 4 and FIG. 5.

At step 712, sampling daemon 102 can transmit the applications and application scores to application manager 106. For example, sampling daemon 102 can select a number (e.g., three) of applications (e.g., "bundleId" attribute values) having the highest scores (e.g., highest probability of being invoked by the user) to transmit to application manager 106. Sampling daemon 102 can exclude applications that have been launched within a previous period of time (e.g., the previous 5 minutes). Sampling daemon 102 can transmit information that identifies the highest scored applications and their respective scores to application manager 106, as described above with reference to FIG. 4.

At step 714, sampling daemon 102 can receive a request from application manager 106 to determine whether it is ok to launch an application. For example, sampling daemon 102 can receive an admission control request that identifies an application (e.g., "bundleId" value).

At step 716, sampling daemon 102 can determine that current mobile device conditions and budgets allow for an application launch. For example, in response to the admission control request, sampling daemon 102 can check system-wide data and energy budgets, attribute budgets and voter feedback to determine whether the application should be launched as a background task on mobile device 100, as described in detail above with reference to FIG. 4.

At step 718, sampling daemon 102 can transmit a reply to application manger 106 indicating that it is ok to launch the identified application. For example, if conditions are good for a background application launch, sampling daemon 102 can return a "yes" value (e.g., ok, yes, true, etc.) to application manager 106 in response to the admission control request so that application manager 106 can launch the identified application.

Short Term Trending

In some implementations, sampling daemon 102 can be configured to detect when attributes are trending. For example, a client application may register interest in a particular attribute with sampling daemon 102. When sampling daemon 102 detects that the particular attribute is trending, sampling daemon 102 can notify the client that the particular attribute is trending.

For example, application manager 106 can register interest in the "bundleId" attribute (or a particular value of the "bundleId" attribute). When sampling daemon 102 determines that the "bundleId" attribute (or value thereof) is trending, sampling daemon 102 can notify application manager 106 of the trend so that application manager 106 can predictively launch the trending application in the background on mobile device 100. For example, an application is trending if the application is being repeatedly invoked by a user of mobile device 100. In some cases, the trending application is a new application or, prior to the trend, a rarely used application that may not be included in the "bundleId" attribute peer forecast described above. Thus, the trending application may not be kept up to date using the application launch forecasting methods described above.

The purpose of attribute trend detection is to detect attributes (e.g., attribute events) that are being reported repeatedly to sampling daemon 102 and to determine an approximate cadence (e.g., periodicity) with which the attributes are being launched, erring on reporting a smaller cadence. Attributes that are being reported repeatedly to the sampling daemon 102 are said to be "trending." The determined cadence can then be used by sampling daemon 102 clients to perform functions or operations in anticipation of the next event associated with the trending attribute.

For example, the determined cadence can be used by application manager 106 to set timers that will trigger the application manager 106 to launch the trending applications in the background so that the applications will be updated when the user invokes the applications, as described above. For example, if the cadence is 5 minutes for an application, application manager 106 can set a timer that will expire every 4 minutes and cause application manager 106 to launch the application so that the application can receive updated content and update the application's interfaces before being invoked again by the user.

In some implementations, the trend detection mechanisms described herein can be used to detect other system event trends beyond application launches, such as repeated software or network notifications, application crashes, etc. For example, clients can register interest in any attribute or attribute value and can receive notifications when the attributes of interest are trending.

In some implementations, sampling daemon 102 can maintain a trending table that can be used to track the behavior of a number of attributes. The trending table can include an attribute value identification field (ATTID), a state field (STATE), a last launch timestamp (LLT), an inter-launch cadence (ILC) that indicates the amount of time between launches, and a confidence field (C).

Figure 8:
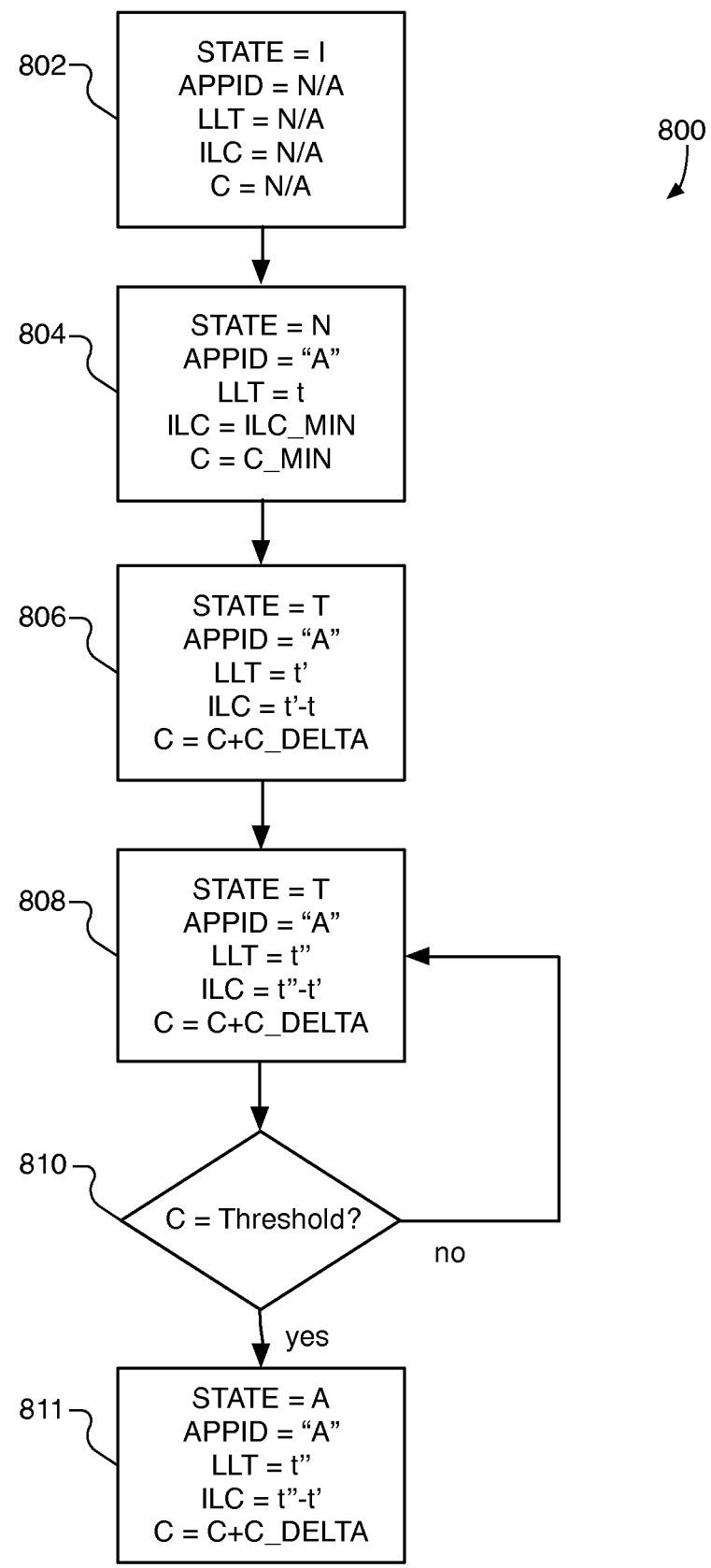
FIG. 8 is a flow diagram illustrating state transitions for an entry in a trending table.

FIG. 8 is a flow diagram 800 illustrating state transitions for an entry (e.g., application) in the trending table. Initially at step 802, the trending table can include empty entries (e.g., records) where the ATTID, LLT, ILC and C fields are empty (e.g., N/A) and the STATE is set to "invalid" (I). When an attribute event is reported at time t, the trending table is scanned for an available entry (e.g., an entry in state I). Among the possible invalid entries, several methods can be used for selecting an entry to use. For example, a random invalid entry can be selected. Alternatively, an invalid entry can be selected such that all the empty entries in the trending table are kept in consecutive order. If no invalid entry exists, the oldest entry (or a random entry) in transient (T) state can be selected to track the newly launched application. If no I or T state entries exist, the oldest new (N) state entry can be selected to track the newly reported attribute event.

At step 804, once the trending table entry is selected, the STATE field of the selected entry for tracking the newly reported attribute event can be set to new (N), the ATTID can be set to the attribute value of the newly reported attribute, the LLT field can be set to the current time t (e.g., wall clock time) and the ILC and C fields are set to predefined minimum values ILC_MIN (e.g., 1 minute) and C_MIN (e.g., zero).

At step 806, on the next report of the same attribute event at time t', the entry in the table for the attribute is found, if it still exists and has not been evicted (e.g., selected to track another attribute). The STATE of the entry is set to transient (T), the ILC is set to the difference between the LLT and the current system time (e.g., t'-t or t'-LLT), and the C field is incremented (e.g., by predefined value C_DELTA). Alternatively, the ILC field can be set to some other function of its old and new values, such as the running average.

At step 808, on the next report of the same attribute event at time t", the entry in the table for the attribute is found, if it still exists and has not been evicted (e.g., selected to track another attribute). The STATE of the entry can remain set to transient (T), the ILC is set to the difference between the LLT and the current (e.g., wall) clock time (e.g., t"-t' or t"-LLT), and the C field is incremented again (e.g., by predefined value C_DELTA).

At step 810, if, after several reports of the attribute event, the C value of the trending table entry reaches (e.g., equals) a threshold value (e.g., C_HIGHTHRESHOLD), at step 811, the state of the attribute entry can be changed to STATE=A. If, at step 810, the C value of the trending table entry does not reach the threshold value (e.g., C_HIGHTHRESHOLD), the values of the entry can be updated according to step 808.

Whenever the attribute event is reported while in state "A", if the time between the last report and the time of the current report is within some amount of time (e.g., ILC_EPSILON=5 minutes), then the attribute entry's confidence (C) field is incremented until it reaches a predefined maximum value (e.g., C_MAX). When an attribute entry in the trending table is in the active (A) state, the entry's ILC value can be used as an estimation of the rate of launch (e.g., cadence) and the entry's ATTID can be used to identify the trending attribute value.

In some implementations, sampling daemon 102 can send the attribute value (ATTID) and cadence value (ILC) to a client so that the client can perform some action or function in anticipation of the next event associated with the attribute value. For example, the attribute value and cadence value can be sent to application manager 106 so that application manager 106 can launch the identified application (e.g., ATTID, "bundleId" attribute value) in the background in anticipation of a user invocation of the application so that the application can receive updated content prior the user launching the application, as described above. For example, application manager 106 can start a timer based on the cadence value that will wake the application manager 106 to launch the application in anticipation of a user invoking the application.

In some implementations, sampling daemon 102 can notify clients of the anticipated next occurrence of an attribute event based on a detected attribute trend. For example, sampling daemon 102 can send application manager 106 a signal or notification indicating that a trending application should be launched by application manager 106. Application manager 106 can register interest in an application by sending sampling daemon 102 an application identifier (e.g., "bundleId" attribute value). Sampling daemon 102 can monitor the application for user invocation (e.g., based on reported "bundleId" start events) to determine whether the application is trending, as described above. If the application is trending, sampling daemon 102 can determine the cadence of invocation, as described above, and send a notification or signal to application manager 106 at a time determined based on the cadence. For example, if the cadence is four minutes, sampling daemon 102 can send a signal to application manager 106 every 3 minutes (e.g., some time period before the next occurrence of the event) to cause application manager 106 to launch the application. If the cadence changes to six minutes, sampling daemon 102 can detect the cadence change and adjust when application manager 106 is signaled. For example, sampling daemon 102 can signal application manager 106 to launch the application every 5 minutes instead of every 3 minutes to adjust for the decreased cadence (e.g., increased time period between invocations).

At each inspection of the attribute trending table for any reason (e.g., adding a new entry, updating an existing entry, etc.), all entries in STATE=T or STATE=A whose time since last launch is greater than their ILC by ILC_EPSILON will have their C values decremented. Any entry whose C value at that point falls below a minimum threshold value (e.g., C_LOWTHRESHOLD) is demoted. An entry can be demoted from state A to state T or from state T to state I, for example.

In some implementations, the trend detection mechanism described above can be used to detect trending events other than application invocations or launches. For example, the trend detection method and trending table described above can be used to detect and track any recurring event (e.g., any attribute event) on mobile device 100. A trending event can include screen touches, network connections, application failures, the occurrence of network intrusions and/or any other event that can be reported or signaled to sampling daemon 102.

Push Notifications

Figure 9:
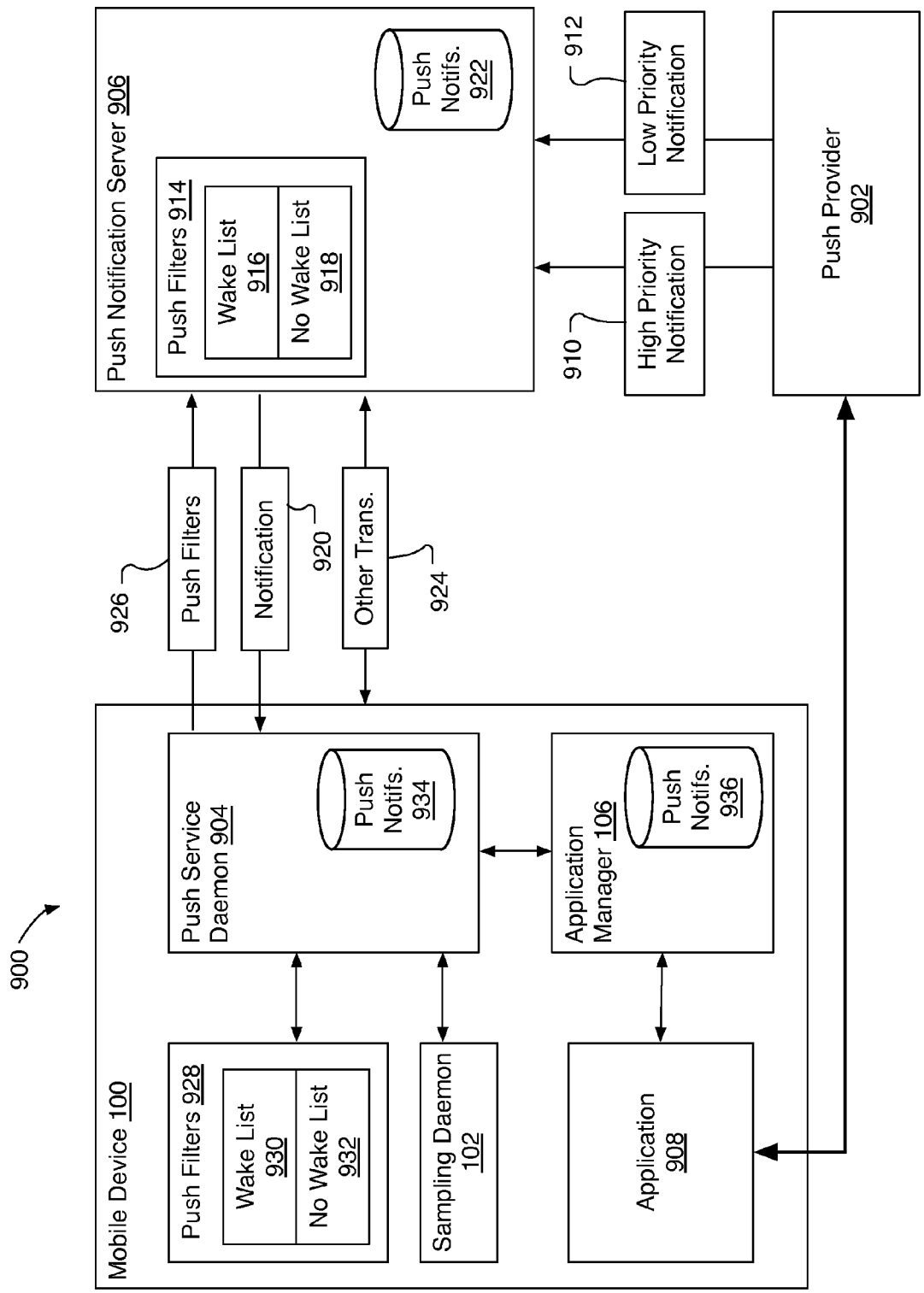
FIG. 9 is a block diagram illustrating a system for providing push notifications to a mobile device.

FIG. 9 is a block diagram 900 illustrating a system for providing push notifications to a mobile device 100. In some implementations, mobile device 100 can be configured to receive push notifications. For example, a push notification can be a message that is initiated by a push provider 902 and sent to a push service daemon 904 running on mobile device 100 through push notification server 906.

In some implementations, push provider 902 can receive authorization to send push notifications to mobile device 100 through a user authorization request presented to a user of mobile device 100 by application 908. For example, push provider 902 can be a server owned, operated and/or maintained by the same vendor that created (e.g., programmed, developed) application 908. Push provider 902 can receive authorization from a user to send push notifications to mobile device 100 (e.g., push service daemon 904) when application 908 presents a user interface on mobile device 100 requesting authorization for push provider 902 to send push notifications to mobile device 100 and the user indicates that push notifications are authorized. For example, the user can select a button on the user interface presented by application 908 to indicate that push notifications are authorized for the push provider 902 and/or application 908. Push provider 902 can then receive a device token that identifies mobile device 100 and that can be used to route push notifications to mobile device 100. For example, push notification server 906 can receive a device token with a push notification and use the device token to determine which mobile device 100 should receive the push notification.

In some implementations, mobile device 100 can send information identifying authorized push applications to push notification server 906. For example, mobile device 100 can send a message 926 containing push notification filters 914 and the device token for mobile device 100 to push notification server 906. Push notification server 906 can store a mapping of device tokens (e.g., identifier for mobile device 100) to push filters 914 for each mobile device serviced by push notification server 906. Push filters 914 can include information identifying applications that have received authorization to receive push notifications on mobile device 100, for example.

In some implementations, push filters 914 can be used by push notification server 906 to filter out (e.g., prevent sending) push notifications to applications that have not been authorized by a user of mobile device 100. Each push notification sent by push provider 902 to push notification server 906 can include information (e.g., an identifier) that identifies the application 908 associated with push provider 902 and the mobile device 100 (e.g., device token).

When notification server 906 receives a push notification, notification server 906 can use the mobile device identification information (e.g., device token) to determine which push filters 914 to apply to the received push notification. Notification server 906 can compare application identification information in the push notification to the push filters 914 for the identified mobile device to determine if the application associated with push provider 902 and identified in the push notification is identified in the push filter 914. If the application associated with the push notification is identified in the push filters 914, then the notification server 906 can transmit the push notification received from push provider 902 to mobile device 100. If the application identified in the push notification is not identified in the push filters 914, then the notification server will not transmit the push notification received from push provider 902 to mobile device 100 and can delete the push notification.

Non-Waking Push Notifications

In some implementations, notification server 906 can be configured to process high priority push notifications and low priority push notifications. For example, push provider 902 can send a high priority push notification 910 and/or a low priority push notification 912 to push notification server 906. Push provider 902 can identify a push notification as high or low priority by specifying the priority of the push notification in data contained within the push notification sent to push notification server 906 and mobile device 100, for example.

In some implementations, push notification server 906 can process low priority push notification 912 differently than high priority push notification 910. For example, push notification server 906 can be configured to compare application identification information contained in high priority push 910 with authorized application identification information in push filters 914 to determine if high priority push notification 910 can be transmitted to mobile device 100. If the application identification information in high priority push notification 910 matches an authorized application identifier in push filters 914, then push notification server 906 can transmit the high priority push notification to mobile device 100. If the application identification information in high priority push notification 910 does not match an authorized application identifier in push filters 914, then push notification server 906 will not transmit the high priority push notification to mobile device 100.

In some implementations, push notification server 906 can be configured to delay delivery of low priority push notifications. For example, when mobile device 100 receives a push notification from push notification server 906, the receipt of the push notification causes mobile device 100 to wake up (e.g., if in a sleep or low power state). When mobile device 100 wakes, mobile device 100 will turn on various subsystems and processors that can drain the battery, use cellular data, cause the mobile device 100 to heat up or otherwise effect the mobile device 100. By preventing or delaying the delivery of low priority push notifications to mobile device 100, mobile device 100 can conserve network (e.g., cellular data) and system (e.g., battery) resources, for example.

In some implementations, push notification filters 914 can include a wake list 916 and a no wake list 918. The wake list 916 can identify applications for which low priority push notifications should be delivered to mobile device 100. In some implementations, when an application is authorized to receive push notifications at mobile device 100, the application identification information is added to the wake list 914 by default. The no wake list 918 can identify authorized applications for which low priority push notifications should be delayed. The specific mechanism for populating no wake list 918 and/or manipulating wake list 916 and no wake list 918 is described in detail below when describing push notification initiated background updates. In some implementations, high priority push notifications will not be delayed at the push notification server 906 and will be delivered to mobile device 100 as long as the application identified in the high priority push notification is identified in push filters 914 (e.g., wake list 914 and/or no wake list 918).

In some implementations, when push notification server 906 receives a low priority push notification 912, push notification server 906 can compare the application identifier in low priority push notification 912 to wake list 916 and/or no wake list 918. For example, if the application identification information in the low priority push notification 912 matches an authorized application identifier in the wake list 916, the low priority push notification 912 will be delivered to the mobile device 100 in a notification message 920.

In some implementations, delivery of low priority push notifications associated with applications identified in the no wake list 918 can be delayed. For example, if an application identified in low priority push notification 912 is also identified in no wake list 918, then low priority push notification 912 can be stored in push notification data store 922 and not immediately delivered to mobile device 100. In some implementations, if the mobile device 100 identified by a push notification (high or low priority) is not currently connected to push notification server 906, the push notification for the disconnected mobile device 100 can be stored in push notification data store 922 for later delivery to mobile device 100.

In some implementations, push notifications stored in push data store 922 will remain in push data store 922 until the application identifier associated with a stored push notification is moved from the no wake list 918 to wake list 916 or until a network connection is established between push notification server 906 and mobile device 100.

For example, a network connection between push notification server 906 and mobile device 100 can be established when another (high or low priority) push notification is delivered to mobile device 100 or when mobile device 100 sends other transmissions 924 (e.g., status message, heartbeat message, keep alive message, etc.) to push notification server 906. For example, mobile device 100 can send a message 924 to push notification server 905 indicating that the mobile device 100 will be active for a period of time (e.g., 5 minutes) and push notification server 906 can send all received push notifications to mobile device 100 during the specified active period of time. In some implementations, when a network connection is established between mobile device 100 and push notification server 906 all push notifications stored in push notification store 922 will be delivered to mobile device 100. For example, push notifications stored in push notification data store 922 can be transmitted through connections created by other transmissions between mobile device 100 an push notification server 906.

In some implementations, mobile device 100 can establish two different communication channels with push notification server 906. For example, the two communication channels can be established simultaneously or at different times. The mobile device 100 can have a cellular data connection and/or a Wi-Fi connection to push notification server 906, for example. In some implementations, mobile device 100 can generate and transmit to push notification server 906 different push filters 914 for each communication channel. For example, a cellular data connection can be associated with first set of push filters 914 for determining when to send high and low priority push notifications across the cellular data connection. A Wi-Fi data connection can be associated with a second set of push filters 914 that are the same or different than the cellular data push filters for determining when to send high and low priority push notifications across the Wi-Fi data connection. When push notification server 906 receives a push notification, push notification server can compare the application identified in the push notification to the push notification filters for the communication channel (e.g., Wi-Fi, cellular) that the push notification server 906 will use to transmit the push notification to the mobile device 100.

Push Initiated Background Updates

In some implementations, receipt of push notifications by mobile device 100 can trigger a background update of applications on the mobile device 100. For example, when mobile device 100 (e.g., push service daemon 904) receives a push notification message 920 from push notification server 906, push service daemon 904 can compare the application identifier in the push notification message 920 to push filters 928 stored on mobile device 100 to determine if the push notification message 920 was properly delivered or should have been filtered (e.g., not delivered) by push notification server 906. For example, push filters 928, wake list 930 and no wake list 932 can correspond to push filters 914, wake list 916 and no wake list 918, respectively. In some implementations, if push service daemon 904 determines that the push notification message 920 should not have been delivered to mobile device 100, the push notification message 902 will be deleted.

Low Priority Push Notifications

In some implementations, the push notification message 920 received by mobile device 100 can include a low priority push notification. For example, the low priority push notification can indicate that content updates are available for the application associated with the push notification. Thus, when the low priority push notification causes a launch of an application 908, the application 908 can download updated content from one or more network resources (e.g., push provider 902).

In some implementations, when push service daemon 904 receives a low priority push notification associated with an application (e.g., application 908) on mobile device 100, push service daemon 904 can ask sampling daemon 102 if it is ok to launch the application associated with the received low priority push notification. For example, push service daemon 904 can request that sampling daemon 102 perform admission control by sending sampling daemon 102 an identifier for the application (e.g., "bundleId" attribute value) associated with the received low priority push notification. Sampling daemon 102 can perform admission control by checking data budgets, energy budgets, attribute budgets and voter feedback, as described above with reference to FIG. 4. Sampling daemon 102 can return to push service daemon 904 a value indicating whether it is ok to launch the application identified by the low priority push notification based on the outcome of the admission control process.

In some implementations, if the value returned from the admission control request indicates "yes" it is ok to launch the application, push service daemon 904 will send the low priority push notification to application manager 106 and application manager 106 can invoke the application (e.g., application 908). Application 908 can then communicate with push provider 902 over the network (e.g., the internet) to receive updated content from push provider 902.

In some implementations, if the value returned from the admission control request indicates "no" it is not ok to launch the application, push service daemon 904 will store the low priority push notification in push notification data store 934. For example, when storing a low priority push notification, push service daemon 904 will only store the last push notification received for the application identified in the push notification.

In some implementations, when sampling daemon 102 indicates that push service daemon 904 should not launch an application right now (e.g., the admission control reply is "no"), push service daemon 904 can move the application identifier for the application from wake list 930 to no wake list 932. For example, if sampling daemon 102 determines that the budgets, and/or conditions of the mobile device do not allow for launching the application, allowing the push notification server 906 to wake mobile device 100 for additional low priority push notifications associated with the application will just further consume the data and energy budgets of the mobile device 100 or make environmental conditions worse (e.g., cause the device to heat up). Thus, by moving the application identifier into the no wake list 932 and sending a message 926 to push notification server 906 that includes the updated filters 928 (e.g., wake list 930 and no wake list 932), notification server 906 can update its own push filters 914, wake list 916 and no wake list 918 to reflect the changes to push filters 928 and to prevent additional low priority push notifications for the application from being delivered to mobile device 100.

In some implementations, if the value returned from the admission control request indicates that it is "never" ok to launch the application, push service daemon 904 will delete the low priority push notification and remove the application identifier associated with the push notification from push filters 928. The updated push filters can be transmitted to push notification server 906 and push filters 914 on push notification server 906 can be updated to prevent push notification server 906 from sending any more push notifications associated with the application identifier.

In some implementations, sampling daemon 102 can transmit a "stop" signal to push service daemon 904 to temporarily prevent future low priority push notifications from being sent from push notification server 906 to mobile device 100. For example, sampling daemon 102 can send a stop signal to push service daemon 904 when sampling daemon 102 determines the data budget is exhausted for the current hour, the energy budget is exhausted for the current hour, the system is experiencing a thermal event (e.g., mobile device 100 is too hot), the mobile device 100 has a poor cellular connection and the mobile device 100 is not connected to Wi-Fi and/or that the mobile device 100 is connected to a voice call and not connected to Wi-Fi. When push service daemon 904 receives a stop signal, push service daemon 904 can move the application identifiers in wake list 930 to no wake list 932 and transmit the updated push filters 928 to push notification server 906 to update push filters 914. Thus, push notification server 906 will temporarily prevent future low priority push notifications from waking mobile device 100 and impacting the budgets, limits and operating conditions of mobile device 100.

In some implementations, sampling daemon 102 can transmit a retry signal to push service daemon 904. For example, sampling daemon 102 can monitor the status of the budgets, network connections, limits and device conditions and will send a retry message to push service daemon 904 when the push data budget is not exhausted, when the energy budget is not exhausted, when the mobile device 100 is not experiencing a thermal event, when the mobile device 100 has a good quality cellular connection or is connected to Wi-Fi, when mobile device 100 is not connected to a voice call and when the launch rate limits have been reset. Once the push service daemon 904 receives the retry signal, push service daemon 904 will send an admission control request to sampling daemon 102 for each push notification in push notification data store 934 to determine if it is ok to launch each application (e.g., "bundleId" attribute value) associated with the stored push notifications.

If sampling daemon 102 returns a "yes" from the admission control request, push service daemon 904 can send the push notification to application manager 106 and application manager 106 can launch the application associated with the push notification as a background process on mobile device 100, as described above. Once the application is launched, the application can download content or data updates and update the applications user interfaces based on the downloaded data. Application manager 106 will not ask sampling daemon 102 if it is ok to launch an application associated with a low priority push notification.

High Priority Push Notifications

In some implementations, the push notification message 920 received by mobile device 100 can include a high priority push notification. For example, the high priority push notification can indicate that content updates are available for the application associated with the push notification. Thus, when the high priority push notification causes an invocation of an application, the application can download updated content from one or more network resources. In some implementations, when a high priority push notification is received by push service daemon 904, push service daemon 904 will send the high priority push notification to application manager 106 without making an admission control request to sampling daemon 102.

In some implementations, when application manager 106 receives a push notification associated with an application, application manager 106 will make an admission control request to sampling daemon 102. In response to the admission control request, sampling daemon 102 can reply with "yes," "no," or "never" responses as described above. When application manager 106 receives a "yes" reply to the admission control request, application manager 106 can launch the application associated with the received high priority push notification as a background process on mobile device 100.

In some implementations, when application manager 106 receives a "no" reply to an admission control request, application manager 106 can store the high priority push notification in high priority push notification store 936. When application manager 106 receives a "never" response, application manager 106 can delete the high priority push notification and delete any push notifications stored in push notification data store 936 for the application associated with the push notification.

In some implementations, sampling daemon 102 can send an "ok to retry" signal to application manager 106. For example, when application manager 106 receives an "ok to retry" message from sampling daemon 102, application manager 106 can make an admission control request for the applications associated with each high priority push notification in high priority push notification data store 936 and launch the respective applications as background processes when a "yes" reply is received in response to the admission control request.

Delaying Display of Push Notifications

In some implementations, high priority push notifications can cause a graphical user interface to be displayed on mobile device 100. For example, receipt of a high priority push notification can cause a banner, balloon or other graphical object to be displayed on a graphical user interface of mobile device 100. The graphical object can include information indicating the subject matter or content of the received push notification, for example.

In some implementations, when application manager 106 receives a high priority push notification, application manager 106 can cause the notification to be displayed on a graphical user interface of the mobile device 100. However, when the high priority push notification indicates that there are data updates to be downloaded to the application associated with the high priority push notification, the application can be launched in the background of mobile device 100 before the push notification is displayed. For example, application manager 106 can be configured with an amount of time (e.g., 30 seconds) to delay between launching an application associated with the high priority push notification and displaying the graphical object (e.g., banner) that announces the push notification to the user. The delay can allow the application enough time to download content updates and update the application's user interfaces before being invoked by the user, for example. Thus, when the user provides input to the graphical object or otherwise invokes the application associated with the high priority push notification, the application's user interfaces will be up to date and the user will not be forced to wait for updates to the application. In some implementations, if application manager 106 is unable to launch the application associated with the high priority push notification, the mobile device 100 will display the graphical object (e.g., banner) to notify the user that the high priority push notification was received.

Example Push Notification Processes

Figure 10:
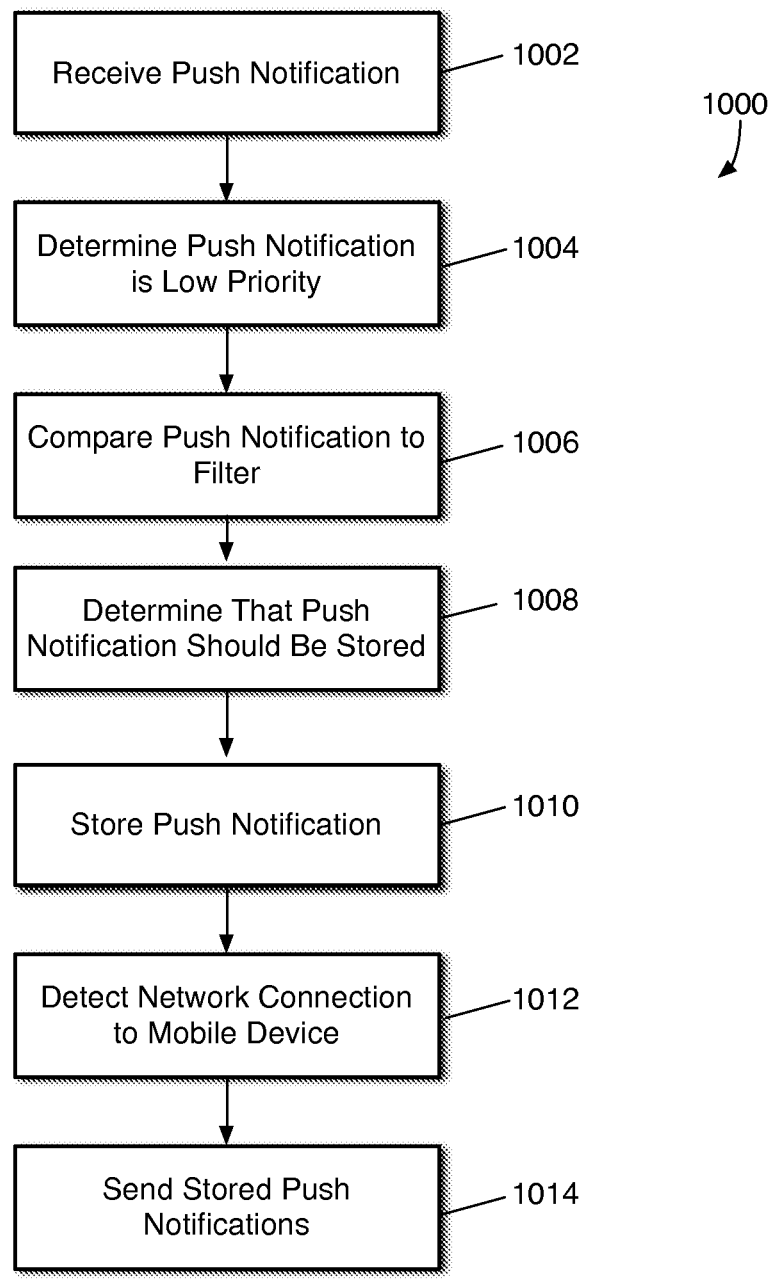
FIG. 10 is a flow diagram of an example process for performing non-waking pushes at a push notification server.

FIG. 10 is a flow diagram of an example process 1000 for performing non-waking pushes at a push notification server 906. At step 1002, push notification server 906 can receive a push notification. For example, push notification server 906 can receive a push notification from a push notification provider 902 (e.g., a server operated by an application vendor).

At step 1004, push notification server 906 can determine that the push notification is a low priority push notification. For example, the push notification provider can include data in the push notification that specifies the priority of the push notification. Push notification server 906 can analyze the contents of the push notification to determine the priority of the push notification.

At step 1006, push notification server 906 can compare the push notification to a push notification filter. For example, the push notification can identify an application installed or configured on mobile device 100 to which the low priority push notification is directed. The push notification can include an application identifier (e.g., a "bundleId" attribute value), for example. Push notification server 906 can compare the application identifier in the push notification to application identifiers in the push notification filter's no wake list 918.

At step 1008, push notification server 906 can determine that the low priority push notification should be stored. For example, if the application identifier from the low priority push notification is in the push notification filter's no wake list 918, the push notification server 906 can determine that the low priority push should be stored in push notification data store 922.

At step 1010, based on the determination at step 1008, the low priority push notification will be stored in a database or data store 922 of the push notification server 906 and not immediately sent to the mobile device 100.

At step 1012, push notification server 906 can determine that a network connection to mobile device 100 has been established. For example, push notification server 906 can create a network connection to mobile device 100 to deliver another high or low priority push. Mobile device 100 can establish a network connection to push notification server 906 to send notification filter changes, periodic status updates, keep alive messages or other messages to push notification server 906.

At step 1014, push notification server 906 can send the stored push notifications in response to determining that a network connection to mobile device 100 has been established. For example, push notification server 906 can send the low priority push notifications stored at the push notification server 906 to mobile device 100.

Figure 11:
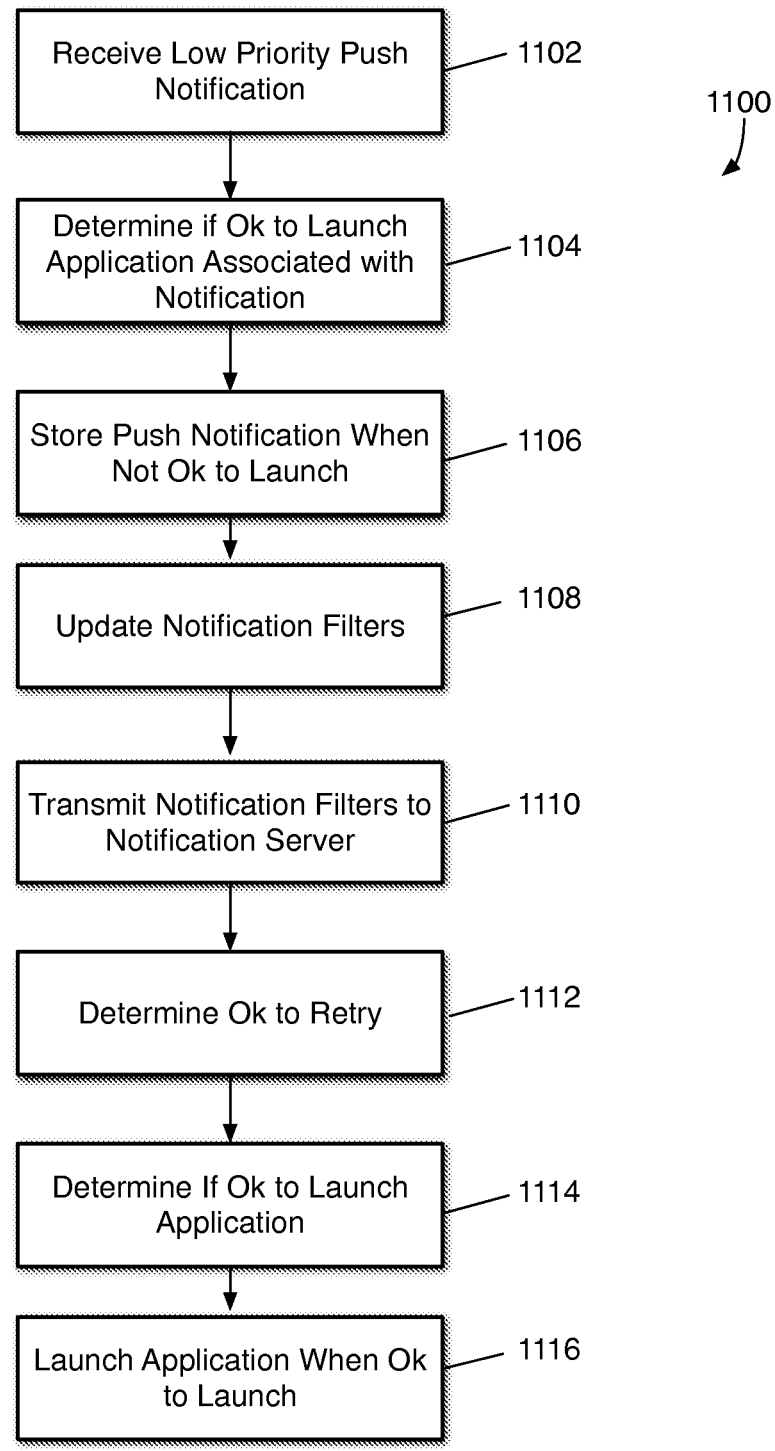
FIG. 11 is a flow diagram of an example process for performing background updating of an application in response to a low priority push notification.

FIG. 11 is a flow diagram of an example process 1100 for performing background updating of an application in response to a low priority push notification. At step 1102, mobile device 100 can receive a low priority push notification from push notification server 906.

At step 1104, mobile device 100 can determine if it is ok to launch an application associated with the low priority push notification. For example, the application can be launched as a background process on mobile device 100. Mobile device 100 can determine whether it is ok to launch the application using the admission control process described above. For example, mobile device 100 (e.g., sampling daemon 102) can determine whether it is ok to launch the application based on data, energy and/or attribute budgets determined for the mobile device 100. Mobile device 100 can determine whether it is ok to launch the application based on conditions of the mobile device, and/or the condition of the mobile device's network connections based on responses from various voters. The details for determining whether it is ok to launch an application (e.g., admission control) are described in greater detail with reference to FIG. 4 above.

At step 1106, mobile device 100 can store the low priority push notification when device conditions, budgets, limits and other data indicate that it is not ok to launch the application. For example, mobile device 100 can store the low priority push notifications in a database or other data store on mobile device 100.

At step 1108, mobile device 100 can update its push notification filters in response to determining that it is not ok to launch a background application. For example, mobile device 100 can move the application associated with the low priority push notification to the no wake list of the push notification filters on mobile device 100.

At step 1110, mobile device 100 can transmit the updated notification filters to push notification server 906. Push notification server 906 can update its own push notification filters based on the filters received from mobile device 100 to determine when to transmit and when to not transmit low priority push notifications to mobile device 100.

At step 1112, mobile device 100 can determine that it is ok to retry launching applications associated with low priority push notifications. For example, mobile device 100 can determine that the budgets, limits and device conditions, as described above, allow for launching additional background applications on the mobile device 100.

At step 1114, mobile device 100 can determine whether it is ok to launch a particular application associated with a stored low priority push notification. For example, sampling daemon 102 of mobile device 100 can perform admission control to determine that the budgets configured on mobile device 100 have been reset or replenished for the current time and that the environmental conditions of the mobile device 100 and network connections are good enough to launch the particular background application.

At step 1116, mobile device 100 can launch the particular application when the mobile device 100 determines that it is ok to launch the application. For example, the particular application can be launched as a background process to download new content and update the user interfaces of the application before a user invokes the application. This process will allow a user to invoke an application and not have to wait for content updates to be downloaded and for user interfaces of the application to be refreshed.

Figure 12:
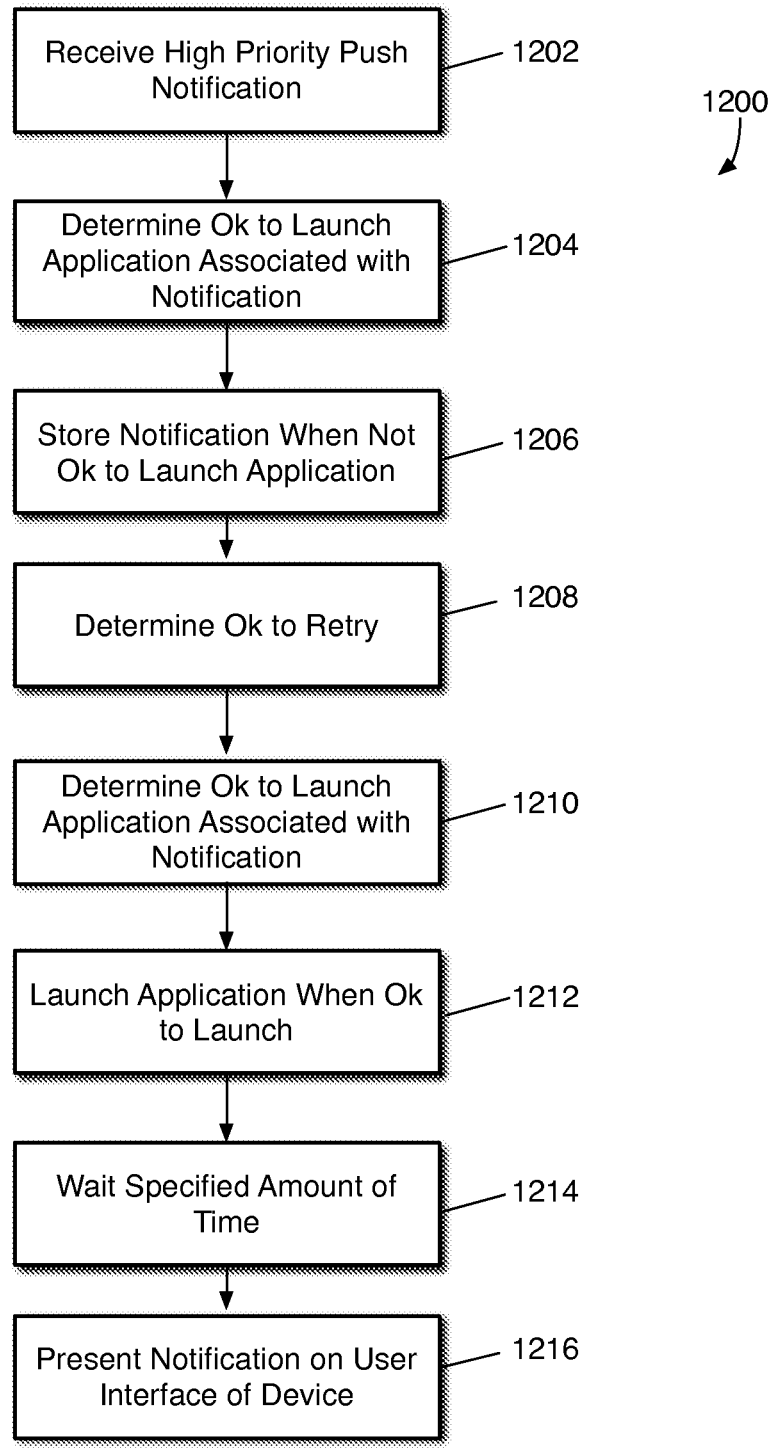
FIG. 12 is a flow diagram of an example process for performing background updating of an application in response to a high priority push notification.

FIG. 12 is a flow diagram of an example process 1200 for performing background updating of an application in response to a high priority push notification. At step 1202, mobile device 100 can receive a high priority push notification.

At step 1204, mobile device 100 can determine if it is ok to launch an application associated with the high priority push notification. For example, sampling daemon 102 of mobile device 100 can perform admission control to determine whether it is ok to launch the application based on budgets and environmental conditions of the mobile device 100 (e.g., device conditions, network conditions, etc.).

At step 1206, mobile device 100 can store the high priority push notification when it is not ok to launch (e.g., admission control returns "no") the application associated with the high priority push notification. For example, mobile device 100 can store the high priority push notification in a database, queue, or other appropriate data structure.

At step 1208, mobile device 100 can determine that it is ok to retry launching applications associated with stored high priority push notifications. For example, mobile device 100 can determine that it is ok to retry launching applications when the data, energy and/or attribute budgets have been replenished, device conditions have improved, network conditions have improved or other conditions of the mobile device 100 have changed, as discussed above in the admission control description.

At step 1210, mobile device 100 can determine if it is ok to launch an application associated with a stored high priority push notification. For example, mobile device 100 can determine if it is ok to launch an application based on the criteria discussed above.

At step 1212, mobile device 100 can launch the application in the background on the mobile device 100. For example, the application can be launched as a background process on the mobile device 100 so that the application can download updated content from a network resource (e.g., a content server) on a network (e.g., the internet).

At step 1214, the mobile device 100 can wait a period of time before presenting the push notification to the user. For example, the mobile device can be configured to allow the application to download content for a period of time before notifying the user of the received high priority push notification.

At step 1216, the mobile device 100 can present the push notification on a user interface of the mobile device 100. For example, the mobile device 100 can present a graphical object (e.g., a banner) that includes information describing the high priority push notification. The user can select the graphical object to invoke the application, for example. Since the application had time to download content before the user was presented with the notification, when the user invokes the application the application will be able to display updated content to the user without forcing the user to wait for the updated content to be downloaded from the network.

Background Uploading/Downloading

Figure 13:
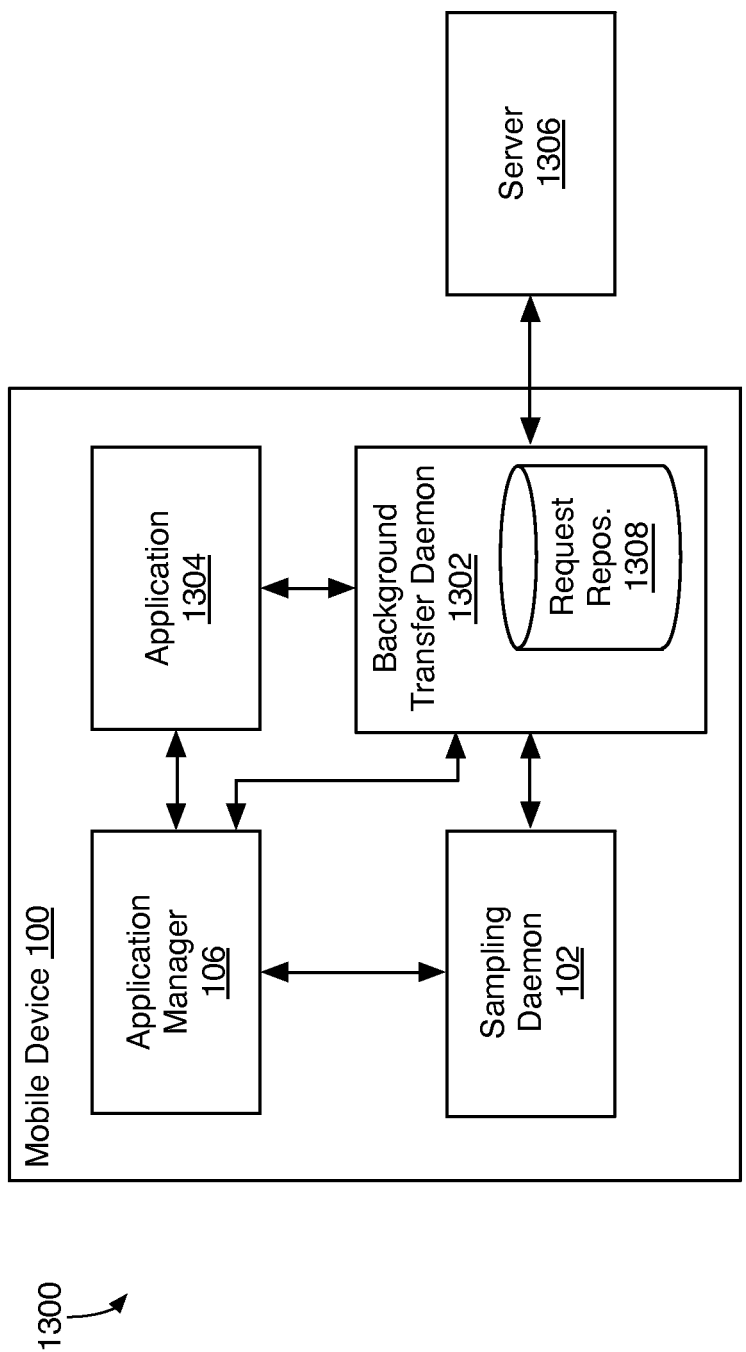
FIG. 13 is a block diagram an example system for performing background downloading and/or uploading of data on a mobile device.

FIG. 13 is a block diagram an example system 1300 for performing background downloading and/or uploading of data on a mobile device 100. A background download and/or upload can be a network data transfer that is initiated by an application without explicit input from the user. For example, a background download could be performed to retrieve the next level of a video game while the user is playing the video game application. In contrast, a foreground download or upload can be a network data transfer performed in response to an explicit indication from the user that the download or upload should occur. For example, a foreground download could be initiated by a user selecting a webpage link to download a picture, movie or document. Similarly, background uploads can be distinguished from foreground uploads based on whether or not an explicit user request to upload data to a network resource (e.g. server) was received from the user.

In some implementations, foreground downloads/uploads (e.g., downloads/uploads explicitly requested by a user) are performed immediately for the user. For example, the user requested downloads/uploads are performed immediately and are not subject to budgeting constraints or other considerations. Foreground downloads/uploads can be performed over a cellular data connection. In contrast, background downloads and/or uploads can be performed opportunistically and within budgeting constraints and considering environmental conditions, such as the temperature of the mobile device 100. For example, a background download or upload can be performed for an attribute or attribute value when the attribute is approved by the admission control mechanisms described above. In some implementations, background downloads and/or uploads can be restricted to Wi-Fi network connections.

In some implementations, system 1300 can include background transfer daemon 1302. In some implementations, background transfer daemon 1302 can be configured to perform background downloading and uploading of data or content on behalf of applications or processes running on mobile device 100. For example background transfer daemon 1302 can perform background download and/or uploads between application 1304 and server 1306 on behalf of application 1304. Thus, the background downloads/uploads can be performed out of process from application 1304 (e.g., not performed in/by the process requesting the download/upload).

In some implementations, application 1304 can initiate a background download/upload by sending a request to background transfer daemon 1304 to download or upload data. For example, a request to download data (e.g., content) can identify a network location from where the data can be downloaded. A request to upload data can identify a network location to which the data can be uploaded and a location where the data is currently stored on the mobile device 100. The request can also identify application 1304. Once the request has been made, application 1304 can be shut down or suspended so that the application will not continue consuming computing and/or network resources on mobile device 100 while the background download/upload is being performed by background transfer daemon 1304.

In some implementations, upon receiving a request to perform a background upload or download of data, background transfer daemon 1302 can send a request to sampling daemon 102 to determine if it is ok for background transfer daemon 1302 to perform a data transfer over the network. For example, background transfer daemon 1302 can request that sampling daemon 102 perform admission control for the data transfer. In the admission control request, background transfer daemon 1302 can provide the identifier (e.g., "bundleId" attribute value) for the background transfer daemon 1302 or the identifier for the application requesting the background transfer so that admission control can be performed on the background transfer daemon or the application. The admission control request can include the amount of data to be transferred as the cost of the request to be deducted from the system-wide data budget.

In response to receiving the admission control request from background transfer daemon 1302, sampling daemon 102 can determine if the system-wide data and/or energy budgets have been exhausted for the current hour. In some implementations, if sampling daemon 102 determines that the mobile device 100 is connected to an external power source, sampling daemon 102 will not prevent a background download/upload based on the energy budget. Sampling daemon 102 can determine if mobile device 100 is connected to Wi-Fi. Sampling daemon 102 can also determine whether mobile device 100 is in the middle of a thermal event (e.g., operating temperature above a predefined threshold value). In some implementations, if sampling daemon 102 determines that the data budget is exhausted and the mobile device 100 is not connected to Wi-Fi, that the energy budget is exhausted and the mobile device 100 is not connected to an external power source, or that the mobile device 100 is in the middle of a thermal event, then sampling daemon 102 will return a "no" reply to the admission control request by background transfer daemon 1302.

In some implementations, when background transfer daemon 1302 receives a "no" reply to the admission control request from sampling daemon 102, process 1302 can store the background download/upload request from application 1304 in request repository 1308.

In some implementations, sampling daemon 102 can send an retry signal to background transfer daemon 1302. For example, sampling daemon 102 can send the retry signal to background transfer daemon 1302 when the data and energy budgets are replenished and when the system is no longer experiencing a thermal event. Sampling daemon 102 can send the retry signal to background transfer daemon 1302 when the mobile device 100 is connected to Wi-Fi, connected to external power and when the system is not experiencing a thermal event. For example, when connected to Wi-Fi, there may not be a need to control data usage. Similarly, when connected to external power, there may not be a need to conserve battery power. Thus, the data and energy budgets may be disregarded by sampling daemon 102 when performing admission control.

In some implementations, when the retry signal is received by background transfer daemon 1302, background transfer daemon 1302 can send an admission control request to sampling daemon 102. If sampling daemon 102 returns an "ok" reply in response to the admission control request, background transfer daemon 1302 can perform the background download or upload for application 1304. Once a background download is completed, background transfer daemon 1302 can wake or invoke application 1304 and provide application 1304 with the downloaded data.

In some implementations, background transfer daemon 1302 can notify sampling daemon 102 when the background download/upload starts and ends so that sampling daemon 102 can adjust the budgets and maintain statistics on the background downloads/uploads performed on mobile device 100. For example, background transfer daemon 1302 can send a "backgroundTransfer" attribute start or stop event to sampling daemon 102. In some implementations, background transfer daemon 1302 can transmit the number of bytes (e.g., "system.networkBytes" attribute event) transferred over cellular data, over Wi-Fi and/or in total so that sampling daemon 102 can adjust the budgets and maintain statistics on the background downloads/uploads performed on mobile device 100.

In some implementations, sampling daemon 102 can return a timeout value to background transfer daemon 1302 in response to an admission control request. For example, the timeout value can indicate a period of time (e.g., 5 minutes) that the background transfer daemon has to perform the background download or upload. When the timeout period elapses, background transfer daemon 1302 will suspend the background download or upload.

In some implementations, the timeout value can be based on remaining energy budgets for the current hour. For example, sampling daemon 102 can determine how much energy is consumed each second while performing a download or upload over Wi-Fi based on historical event data collected by sampling daemon 102. Sampling daemon 102 can determine the time out period by dividing the remaining energy budget by the rate at which energy is consumed while performing a background download or upload (e.g., energy budget/energy consumed/time=timeout period).

In some implementations, background downloads and/or uploads are resumable. For example, if mobile device 100 moves out of Wi-Fi range, the background download/upload can be suspended (e.g., paused). When mobile device 100 reenters Wi-Fi range, the suspended download/upload can be resumed. Similarly, if the background download/upload runs out of energy budget (e.g., timeout period elapses), the background download/upload can be suspended. When additional budget is allocated (e.g., in the next hour), the suspended download/upload can be resumed.

In some implementations, background downloads/uploads can be suspended based on the quality of the network connection. For example, even though mobile device 100 can have a good cellular data connection between mobile device 100 and the servicing cellular tower and a good data connection between the cellular tower and the server that the mobile device 100 is transferring data to or from, mobile device 100 may not have a good connection to the server. For example, the transfer rate between the mobile device 100 and the server may be slow or the throughput of the cellular interface may be low. If the transfer rate of the background download/upload falls below a threshold transfer rate value and/or the throughput of the background download/upload falls below a threshold throughput value, the background download/upload (e.g., data transfer) can be suspended or paused based on the detected poor quality network connection until a better network connection is available. For example, if a Wi-Fi connection becomes available the suspended background download/upload can be resumed over the Wi-Fi connection.

In some implementations, background transfer daemon 1302 can be configured with a limit on the number of background downloads and/or uploads that can be performed at a time. For example, background transfer daemon 1302 can restrict the number of concurrent background downloads and/or uploads to three.

Example Background Download/Upload Process

Figure 14:
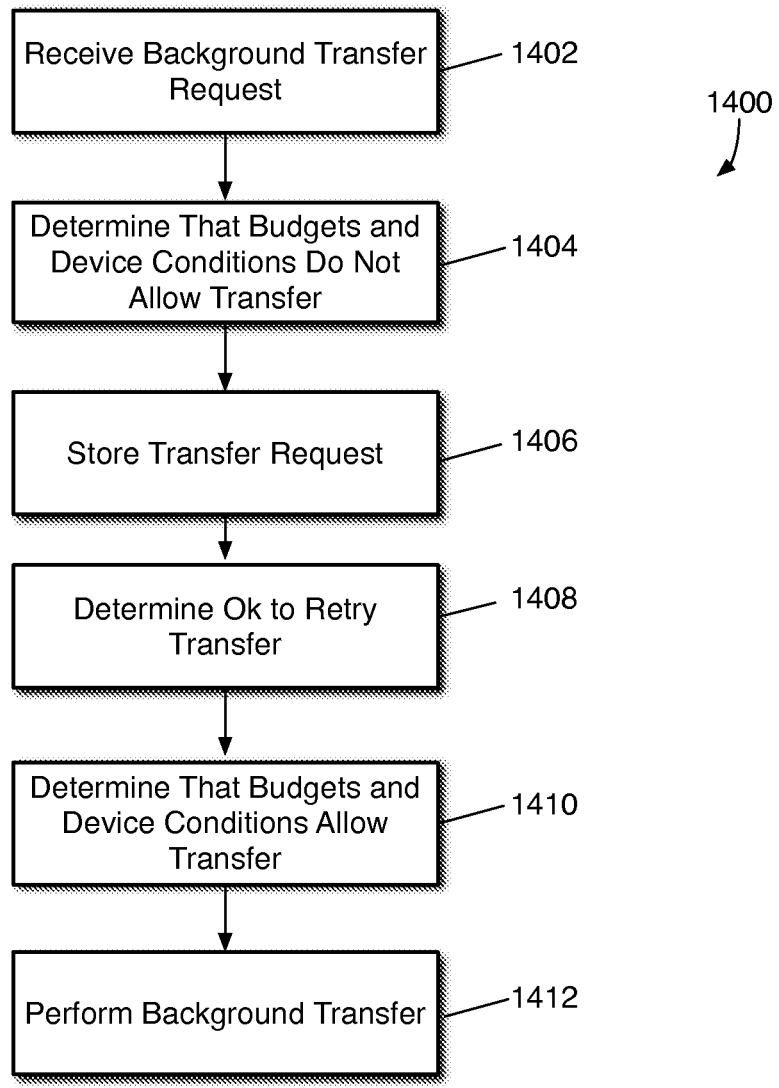
FIG. 14 is flow diagram of an example process for performing background downloads and uploads.

FIG. 14 is flow diagram of an example process 1400 for performing background downloads and uploads. For example, background downloads and/or uploads can be performed on behalf of applications on mobile device 100 by background transfer daemon 1302.

At step 1402, a background transfer request can be received. For example, background transfer daemon 1302 can receive a background download/upload request from an application running on mobile device 100. Once the application makes the request, the application can be terminated or suspended, for example. The request can identify the application and identify source and/or destination locations for the data. For example, when downloading data the source location can be a network address for a server and the destination location can be a directory in a file system of the mobile device 100. When uploading data, the source location can be a file system location and the destination can be a network location.

At step 1404, mobile device 100 can determine that budgets and device conditions do not allow for the data transfer. For example, background transfer daemon 1302 can ask sampling daemon 102 if it is ok to perform the requested background transfer by making an admission control request to sampling daemon 102 that identifies the background transfer daemon 1302, the application for which the background transfer is being performed, and/or the amount of data to be transferred. Sampling daemon 102 can determine if energy and data budgets are exhausted and if the mobile device 100 is in the middle of a thermal event. If the budgets are exhausted or if the mobile device 100 is in the middle of a thermal event, sampling daemon 102 can send a message to background transfer daemon 1302 indicating that it is not ok to perform the background data transfer (e.g., admission control returns "no").

At step 1406, mobile device 100 can store the background transfer request. For example, background transfer daemon 1302 can store the transfer request in a transfer request repository when sampling daemon 102 returns a "no" value in response to the admission control request.

At step 1408, mobile device 100 can determine that it is ok to retry the background transfer. For example, sampling daemon 102 can determine that the data and energy budgets have been replenished and that the mobile device 100 is not in the middle of a thermal event. Sampling daemon 102 can send a retry message to background transfer daemon 1302. Background transfer daemon 1302 can then attempt to perform the requested transfers stored in the transfer request repository by making another admission control request for each of the stored transfer requests.

At step 1410, mobile device 100 can determine that budgets and conditions of the mobile device 100 allow for background data transfer. For example, background transfer daemon 1302 can ask sampling daemon 102 if it is ok to perform the requested background transfer. Sampling daemon 102 can perform admission control to determine that energy and data budgets are replenished and that the mobile device 100 is not in the middle of a thermal event. If the budgets are not exhausted and if the mobile device 100 is not in the middle of a thermal event, sampling daemon 102 can send a message to background transfer daemon 1302 indicating that it is ok to perform the background data transfer.

At step 1412, mobile device 100 can perform the background transfer. For example, background transfer daemon 1302 can perform the requested background download or background upload for the requesting application. Background transfer daemon 1302 can notify sampling daemon 102 when the background transfer begins and ends (e.g., using "backgroundTransfer" attribute start and stop events). Background transfer daemon 1302 can send a message informing sampling daemon of the number of bytes transferred during the background download or upload (e.g., using the "networkBytes" attribute event). Once the background transfer is complete, background transfer daemon 1302 can invoke (e.g., launch or wake) the application that made the background transfer request and send completion status information (e.g., success, error, downloaded data, etc.) to the requesting application.

Enabling/Disabling Background Updates

Figure 15:
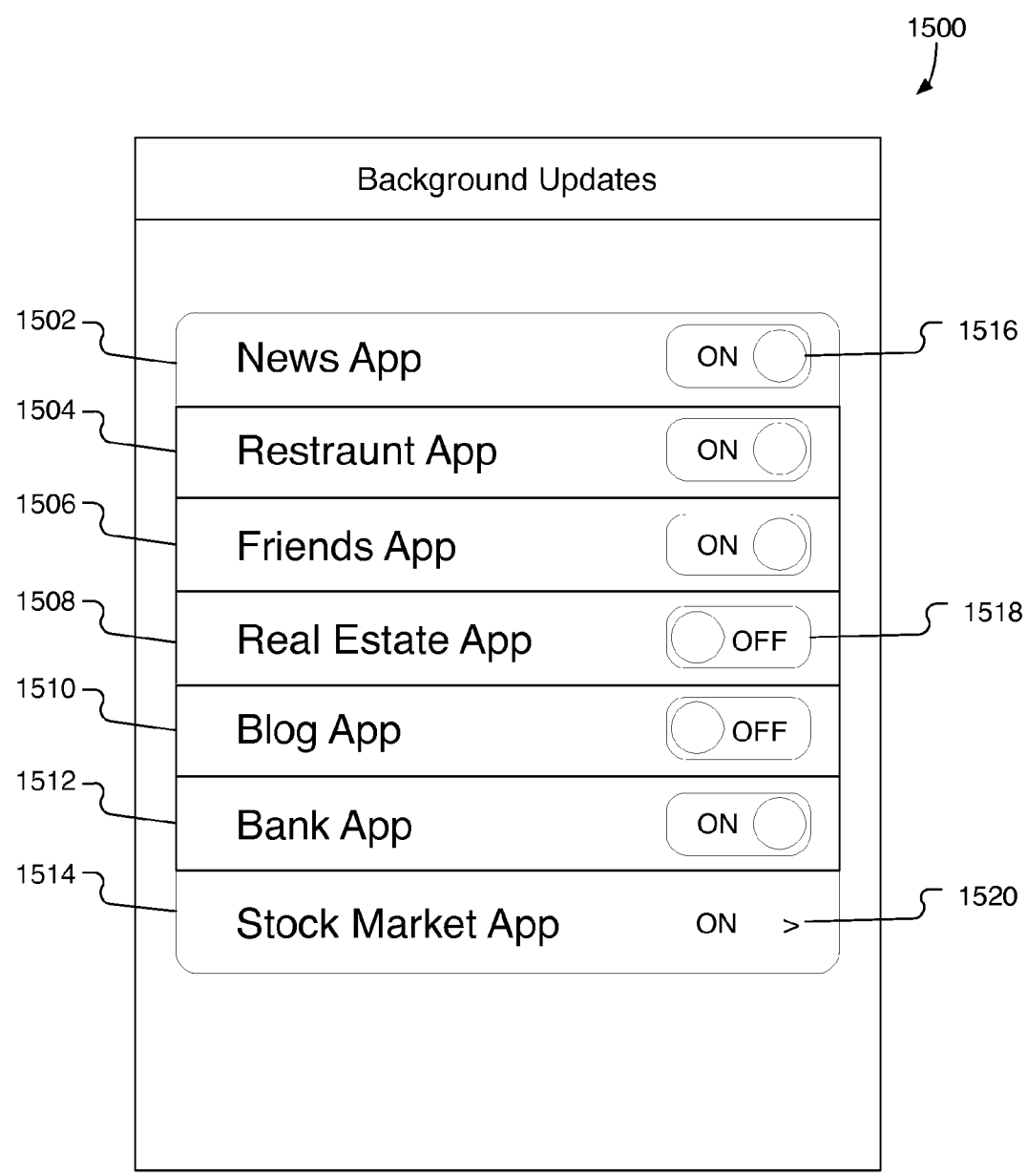
FIG. 15 illustrates an example graphical user interface (GUI) for enabling and/or disabling background updates for applications on a mobile device.

FIG. 15 illustrates an example graphical user interface (GUI) 1500 for enabling and/or disabling background updates for applications on a mobile device. For example, GUI 1500 can be an interface presented on a display of mobile device 100 for receiving user input to adjust background update settings for applications on mobile device 100.

In some implementations, user input to GUI 1500 can enable or disable background updates from being performed for applications based on a user invocation forecast, as described above. For example, sampling process 102 and/or application manager 106 can determine whether background updates are enabled or disabled for an application and prevent the application from being launched by application manager 106 or prevent the application from being included in application invocation forecasts generated by sampling daemon 102. For example, if background updates are disabled for an application, sampling daemon 102 will not include the application the user invoked application forecast requested by when application manager 106. Thus, application manager 106 will not launch the application when background updates are disabled. Conversely, if background updates are enabled for the application, the application may be included in the application invocation forecast generated by sampling daemon 102 based on user invocation probabilities, as described above.

In some implementations, user input to GUI 1500 can enable or disable background updates from being performed for applications when a push notification is received, as described above. For example, sampling daemon 102, application manager 106 and/or push service daemon 904 can determine whether background updates are enabled or disabled for an application and prevent the application from being launched by application manager 106 in response to receiving a push notification. For example, if background updates are disabled for an application and a push notification is received for the application, application manager 106 will not launch the application to download updates in response to the push notification.

In some implementations, GUI 1500 can display applications 1502-1514 that have been configured to perform background updates. For example, the applications 1502-1514 can be configured or programmed to run as background processes on mobile device 100 when launched by application manager 106. When run as a background process, the applications 1502-1514 can communicate with various network resources to download current or updated content. The applications 1502-1514 can then update their respective user interfaces to present updated content when invoked by a user of mobile device 100. In some implementations, applications that are not configured or programmed to perform background updates will not be displayed on GUI 1500.

In some implementations, a user can provide input to GUI 1500 to enable and/or disable background updates for an application. For example, a user can provide input (e.g., touch input) to mobile device 102 with respect to toggle 1516 to turn on or off background updates for application 1502. A user can provide input (e.g., touch input) to mobile device 102 with respect to toggle 1518 to turn on or off background updates for application 1508.

In some implementations, additional options can be specified for a background update application through GUI 1500. For example, a user can select graphical object 1510 associated with application 1514 to invoke a graphical user interface (not shown) for specifying additional background update options. The background update options can include, for example, a start time and an end time for turning on and/or off background updates for application 1514.

Sharing Data Between Peer Devices

Figure 16:
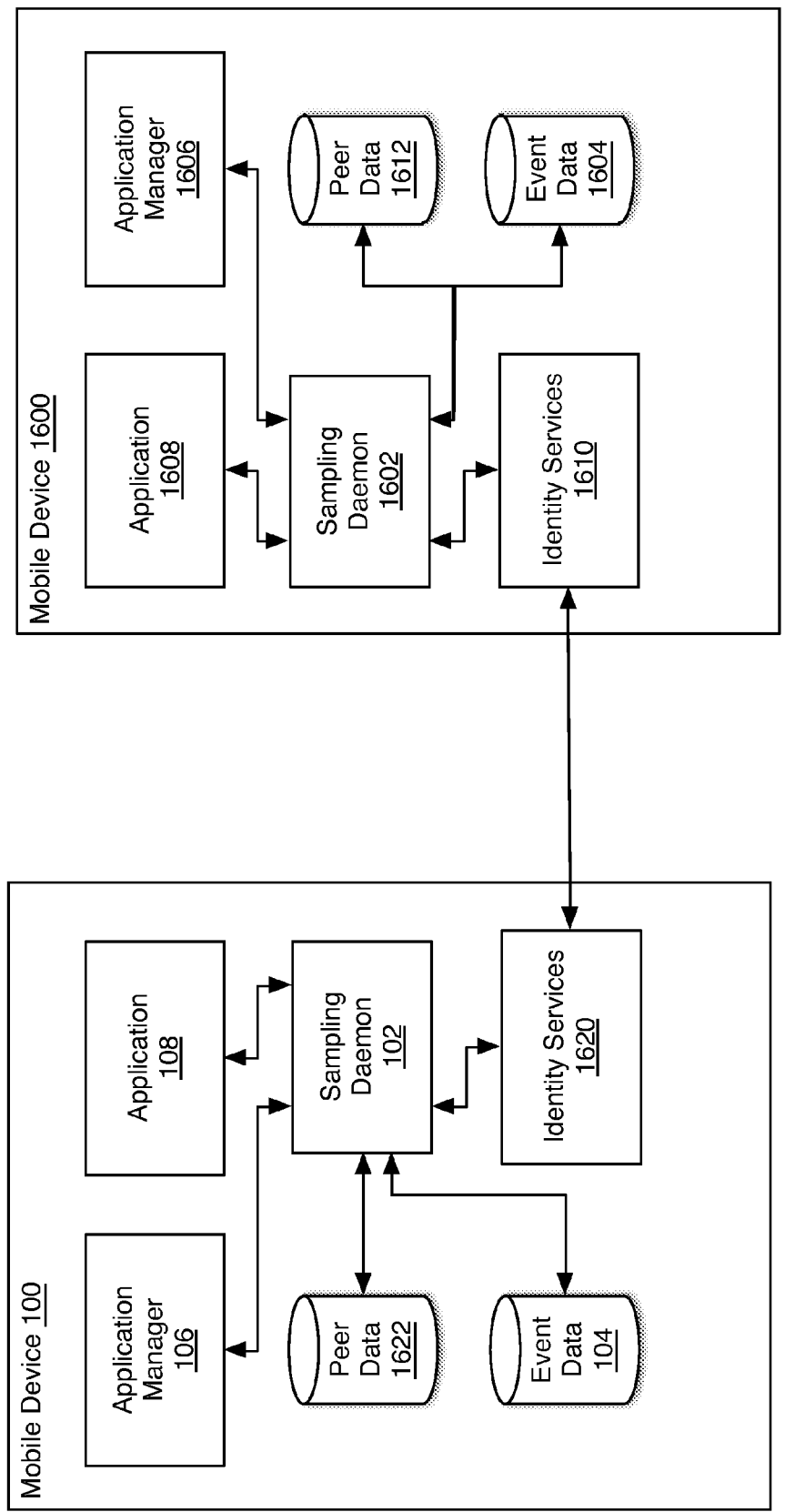
FIG. 16 illustrates an example system for sharing data between peer devices.

FIG. 16 illustrates an example system for sharing data between peer devices. In some implementations, mobile device 100 can share event data, system data and/or event forecasts with mobile device 1600. For example, mobile device 100 and mobile device 1600 can be devices owned by the same user. Thus, it may be beneficial to share information about the user's activities on each device between mobile device 100 and mobile device 1600.

In some implementations, mobile device 1600 can be configured similarly to mobile device 100, described above. For example, mobile device 1600 can be configured with a sampling daemon 1602 that provides the functionalities described in the above paragraphs (e.g., attributes, attribute events, forecasting, admission control, etc.).

In some implementations, mobile device 100 and mobile device 1600 can be configured with identity services daemon 1620 and identity service daemon 1610, respectively. For example, identity services daemon 1620 and 1610 can be configured to communicate information between mobile device 100 and mobile device 1600. The identity services daemon can be used to share data between devices owned by the same user over various peer-to-peer and network connections. For example, identity services daemon 1620 and identity services daemon 1610 can exchange information over Bluetooth, Bluetooth Low Energy, Wi-Fi, LAN, WAN and/or Internet connections.

In some implementations, sampling daemon 1602 (and sampling daemon 102) can be configured to share event forecasts and system state information with other sampling daemons running on other devices owned by the same user. For example, if mobile device 100 and mobile device 1600 are owned by the same user, sampling daemon 102 and sampling daemon 1602 can exchange event forecast information and/or system status information (e.g., battery status). For example, sampling daemon 1602 can send event forecast information and/or system status information using identity services daemon 1610. Identity services daemon 1610 can establish a connection to identity services daemon 1620 and communicate event forecast information and/or mobile device 1600 system status information to sampling daemon 102 through identity services daemon 1620.

In some implementations, application 1608 (e.g., a client of sampling daemon 1602) can request that sampling daemon 1602 send event forecasts for a specified attribute or attribute value to sampling daemon 102. For example, application 1608 can be an application that is synchronized with application 108 of mobile device 100. For example, applications 108 and 1608 can be media applications (e.g., music libraries, video libraries, email applications, messaging applications, etc.) that are configured to synchronize data (e.g., media files, messages, status information, etc.) between mobile device 100 and mobile device 1600.

In some implementations, in order to allow a peer device (e.g., mobile device 100) determine when to synchronize data between devices, application 1608 can request that sampling daemon 1602 generate temporal and/or peer forecasts for the "bundleId" attribute or a specific "bundleId" attribute value (e.g., the application identifier for application 1608) based on attribute event data generated by mobile device 1600 and transmit the forecasts to sampling daemon 102. For example, a peer device can be remote device (e.g., not the current local device) owned by the same user. Mobile device 100 can be a peer device of mobile device 1600, for example.

In some implementations, the requesting client (e.g., application 1608) can specify a schedule for delivery and a duration for forecast data. For example, application 1608 can request a peer and/or temporal forecast for the "bundleId" attribute value "mailapp." Application 1608 can request that the forecast be generated and exchanged every week and that each forecast cover a duration or period of one week, for example.

In some implementations, data exchanges between peer devices can be statically scheduled. Sampling daemon 1602 can send attribute data that is necessary for mobile device 100 to have a consistent view of the remote state of mobile device 1600 under a strict schedule (e.g., application forecasts and battery statistics every 24 hours). In some implementations, clients can request attribute forecasts or statistics on-demand from the peer device. These exchanges are non-recurring. The requesting client can be notified when the requested data is received.

In some implementations, sampling daemon 1602 can transmit system state data for mobile device 1600 to sampling daemon 102. For example, sampling daemon 1602 can receive battery charge level events (e.g., "batteryLevel" attribute events), battery charging events (e.g., "cableplugin" events), energy usage events (e.g., "energy" attribute events) and/or other events that can be used to generate battery usage and charging statistics and transmit the battery-related event data to sampling daemon 102. For example, battery state information can be exchanged every 24 hours. Battery state information can be exchanged opportunistically. For example, when a communication channel (e.g., peer-to-peer, networked, etc.) is established mobile device 100 and mobile device 1600, the mobile devices can opportunistically use the already opened communication channel to exchange battery state or other system state information (e.g., an identification of the current foreground application).

As another example, sampling daemon 1602 can receive thermal level events (e.g., "thermalLevel" attribute events), network events (e.g., "networkQuality" attribute events, "networkBytes" attribute events) and transmit the thermal and/or network events to sampling daemon 102. Sampling daemon 1602 can receive events (e.g., "system.foregroundApp" attribute event) from application manager 106 that indicates which application (e.g., application identifier) is currently in the foreground of mobile device 1600 and transmit the foreground application information to sampling daemon 102. In some implementations, thermal events and foreground application change information can be exchanged with peer devices as soon as the events occur (e.g., as soon as a connection is established between peer devices). In some implementations, network status information can be exchanged on a periodic basis (e.g., once a day, twice a day, every hour, etc.).

Upon receipt of the forecast and/or system event data from sampling daemon 1602, sampling daemon 102 can store the forecast and/or event data in peer data store 1622. Similarly, any forecast and/or event data that sampling daemon 1602 receives from sampling daemon 102 can be stored in peer data store 1612. In some implementations, forecast and/or event data received from another device can be associated with device a device description. For example, the device description can include a device name, a device identifier and a model identifier that identifies the model of the device. The device description can be used to lookup forecast data and/or event data for the device in peer data store 1622. Once mobile device 100 and mobile device 1600 have exchanged forecast and/or event data, the mobile devices can use the exchanged information to determine when to communicate with each other using the remote admission control mechanism below. By allowing devices to share information only when the information is needed and when the battery state of the devices can support sharing the information, power management of communications can be improved.

Remote Admission Control

In some implementations, mobile device 100 (or mobile device 1600) can perform admission control based on data received from another device. For example, sampling daemon 102 can perform admission control based on forecast and system event data received from sampling daemon 1602 and stored in peer data store 1622. For example, to synchronize data with application 1608, application 108 can send a synchronization message to identity services daemon 1620. For example, the synchronization message can include an identifier for mobile device 100, an identifier for mobile device 1600, a priority identifier (e.g., high, low), and a message payload (e.g., data to be synchronized).

Low Priority Messages

In some implementations, a low priority message can be transmitted after going through admission control. For example, a low priority message can be a message associated with discretionary processing (e.g., background applications, system utilities, anticipatory activities, activities that are not user-initiated). For example, identity services daemon 1620 can send an admission control request to sampling daemon 102 for a "bundleId" attribute value that is the bundle identifier for application 1608 (e.g., "bundleId"="1608"). In addition to the "bundleId" attribute name and value (e.g., "1608"), identity services daemon 1620 can provide the device name (e.g., "device1600") in the admission control request to indicate that application 108 is requesting admission control for communication with another device.

In some implementations, in response to receiving the admission control request, sampling daemon 102 can perform local admission control and remote admission control. For example, sampling daemon 102 can perform local admission control, as described above, to determine if mobile device 100 is in condition to allow an event associated with the specified attribute value (e.g., "bundleId"="1608") to occur. Sampling daemon 102 can check local energy, data and attribute budgets, for example, and ask for voter feedback to determine whether mobile device 100 is in condition to allow an event associated with the specified attribute value (e.g., "bundleId"="1608").

In addition to performing local admission control, sampling daemon 102 can perform remote admission control based on the "bundleId" attribute forecasts, event data and system data received from mobile device 1600 and stored in peer data store 1622.

For example, sampling daemon 102 can use the device identifier (e.g., "device1600", device name, unique identifier, UUID, etc.) to locate data associated with mobile device 1600 in peer data store 1622. Sampling daemon 102 can analyze the attribute (e.g., "bundleId") forecast data received from sampling daemon 1602 to determine if application 1608 is likely to be invoked by the user on mobile device 1600 in the current 15-minute timeslot. If application 1608 is not likely to be invoked by the user in the current 15-minute timeslot, then sampling daemon 102 can return a "no" value in response to the admission control request. For example, by allowing application 108 to synchronize with application 1608 only when application 1608 is likely to be used on mobile device 1600, sampling daemon 102 can delay the synchronization process and conserve system resources (e.g., battery, CPU cycles, network data) until such time as the user is likely to use application 1608 on mobile device 1600.

In some implementations, if application 1608 is likely to be invoked by the user of mobile device 1600 in the current 15-minute timeslot, then sampling daemon 102 can check the system data associated with mobile device 1600 and stored in peer data store 1622. For example, sampling daemon 102 can check the system data associated with mobile device 1600 to determine if mobile device 1600 has enough battery charge remaining to perform the synchronization between application 108 and application 1608. For example, sampling daemon 102 can check if there is currently enough battery charge to complete the synchronization between application 108 and application 1608. Sampling daemon 102 can check if there is enough battery charge to perform the synchronization and continue operating until the next predicted battery recharge (e.g., "cablePlugin" attribute event). For example, sampling daemon 102 can generate a temporal forecast for the "cablePlugin" attribute that identifies when the next "cablePlugin" attribute event is likely to occur. Sampling daemon 102 can analyze energy usage statistics (events) to predict energy usage until the next "cablePlugin" event and determine if there is enough surplus energy to service the synchronization transmission between application 108 and application 1608. If sampling daemon 102 determines that mobile device 1600 does not have enough energy (e.g., battery charge) to service the synchronization, sampling daemon 102 can return a "no" value in response to the remote admission control request.

In some implementations, sampling daemon 102 can check the system data associated with mobile device 1600 to determine if mobile device 1600 is in a normal thermal condition (e.g., not too hot) and can handle processing the synchronization request. For example, if "thermalLevel" attribute event data received from mobile device 1600 indicates that mobile device 1600 is currently operating at a temperature above a threshold value, sampling daemon 102 can prevent the synchronization communication by returning a "no" value in response to the remote admission control request.

In some implementations, when the forecast data indicates that the user is likely to invoke application 1608 on mobile device 1600 and the energy, thermal and other system state information indicate that mobile device 1600 is in condition to handle a communication from mobile device 100, sampling daemon 102 can return a "yes" value to identity services daemon 1620 in response to the admission control request. In response to receiving a "yes" value in response to the admission control request, identity services daemon 1620 can transmit the synchronization message for application 108 to identity services daemon 1610 on mobile device 1600. Application 108 and application 1608 can then synchronize data by exchanging messages through identity services daemon 1620 and identity services daemon 1610.

In some implementations, a high priority message can be transmitted after going through remote admission control. For example, a high priority message can be a message associated with a user-initiated task, such as a message associated with a foreground application or a message generated in response to a user providing input. In some implementations, admission control for high priority messages can be handled similarly to low priority messages. However, when performing remote admission control for high priority messages, a high priority message can be admitted (allowed) without considering attribute forecast data (e.g., "bundleId" forecast data) because the high priority message is typically triggered by some user action instead of being initiated by some discretionary background task.

In some implementations, when performing admission control for high priority messages, the battery state of the remote device (e.g., mobile device 1600) can be checked to make sure the remote device (e.g., peer device) has enough battery charge available to process the high priority message. If there is enough battery charge available on the remote device, then the high priority message will be approved by remote admission control. For example, sampling daemon 102 can transmit a "yes" value to identity services daemon 1620 in response to the remote admission control request when there is enough battery charge remaining to process the high priority message. If there is not enough battery charge available on the remote device, then the high priority message will be rejected by remote admission control. For example, sampling daemon 102 can transmit a "no" value to identity services daemon 1620 in response to the remote admission control request when there is enough battery charge remaining to process the high priority message. Thus, identity services daemon 1620 will initiate communication with a peer device (e.g., mobile device 1600) when the peer device has enough battery charge remaining to process the message in question.

In some implementations, when a sampling daemon 102 is notified of a high priority message, sampling daemon 102 can send current battery state information (e.g., current charge level) to identity services daemon 1620. Identity services daemon 1620 can then add the battery state information to the high priority message. Thus, system state information can be efficiently shared between devices by piggy backing the battery state information (or other information, e.g., thermal level, foreground application, etc.) on other messages transmitted between mobile device 100 and mobile device 1600.

In some implementations, sampling daemon 102 can send a retry message to identity services daemon 1620. For example, when conditions on mobile device 100 or mobile device 1600 change (e.g., battery conditions improve), sampling daemon 102 can send identity services daemon 1620 a retry message. In some implementations, a retry message can be generated when the remote focal application changes. For example, if the user on the remote peer device is using the "mailapp" application, the "mailapp" application becomes the focal application. When the user begins using the "webbrowser" application, the focal application changes to the "webbrowser" application. The change in focal application can be reported as an event to sampling daemon 1602 and transmitted to sampling daemon 102 when peer data is exchanged between mobile device 100 and mobile device 1600. Upon receiving the event information indicating a change in focal application at the peer device 1602, sampling daemon 102 can send a retry message to identity services daemon 1620. Identity services daemon 1620 can then retry admission control for each message that was rejected by sampling daemon 102. For example, identity services daemon 1620 can store rejected messages (e.g., transmission tasks) and send the rejected messages through admission control when a retry message is received from sampling daemon 102. In some implementations, rejected messages can be transmitted after a period of time has passed. For example, a message that has not passed admission control can be sent to the peer device after a configurable period of time has passed.

In some implementations, identity services daemon 1620 can interrupt a data stream transmission when sampling daemon 102 indicates that conditions on mobile device 100 or mobile device 1600 have changed. For example, if sampling daemon 102 determines that battery conditions on mobile device 100 or mobile device 1600 have changed such that one of the mobile devices may run out of battery power, sampling daemon 102 can tell identity services daemon 1620 to stop transmitting and retry admission control for the attribute event associated with the data stream.

Process for Sharing Data Between Peer Devices

Figure 17:
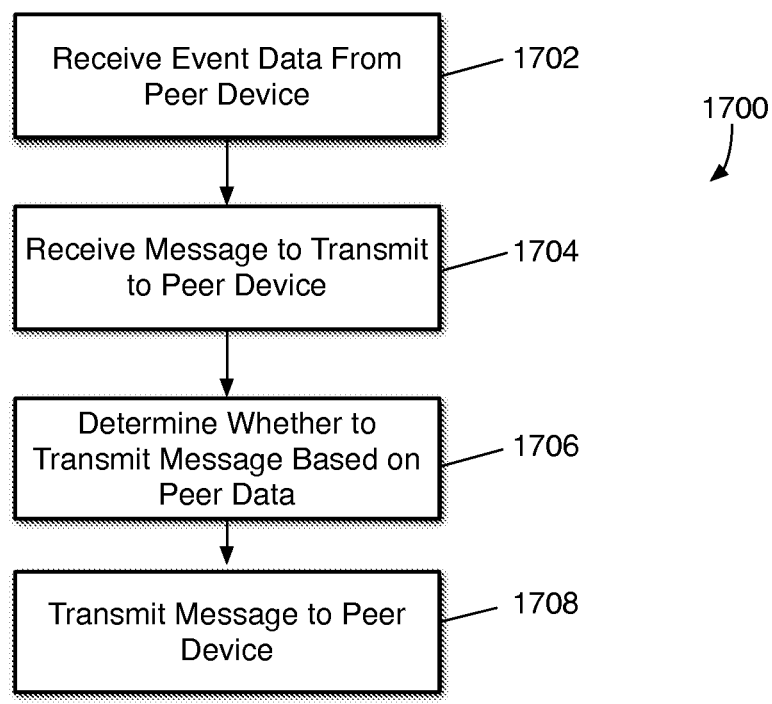
FIG. 17 illustrates an example process for sharing data between peer devices.

FIG. 17 illustrates an example process 1700 for sharing data between peer devices. Additional details for process 1700 can be found above with reference to FIG. 16. At step 1702, a mobile device can receive event data from a peer device. For example, event data can be shared as "digests" (e.g., forecasts, statistics, etc.) or as raw (e.g., unprocessed) event data. For example, a second device (e.g., mobile device 1600) is a peer device of the mobile device 100 when the second device and the mobile device are owned by the same user. The mobile device 100 can receive event data related to system state (e.g., battery state, network state, foreground application identifier, etc.) of mobile device 1600. The mobile device can receive attribute event forecasts, statistics, or raw event data from the mobile device 1600 based on events that have occurred on mobile device 1600. For example, an application 1608 on the peer device 1600 can instruct the sampling daemon 1602 on the peer device 1600 to generate and send forecasts for a particular attribute or attribute value to the mobile device 100.

At step 1704, an identity services daemon 1620 on the mobile device 100 can receive a message to transmit to the peer device 1600. For example, an application 108 running on the mobile device may need to share, exchange or synchronize data with a corresponding application 1608 on the peer device 1600. The application 108 can send a message containing the data to be shared to the identity services daemon 1620.

At step 1706, the sampling daemon 102 on the mobile device 100 can determine whether to transmit the message based on data received from the peer device 1600. For example, the sampling daemon 102 can perform a local admission control check and a remote admission control check to determine whether the message should be sent to the peer device 1600 at the current time. If the attribute event forecasts received from the peer device 1600 indicate that the user of peer device 1600 is likely to invoke application 1608 at the current time and if the event data indicates that the conditions (e.g., battery state, thermal level, etc.) of peer device 1600 are such that initiating communication with peer device 1600 will not deplete the battery or make the thermal state worse, then sampling daemon 102 can approve the transmission of the message.

At step 1708, once sampling daemon 102 performs admission control and approves initiating communication with the peer device 1600, identity services daemon 1620 can transmit the message to the peer device 1600. For example, identity services daemon 1620 can transmit the message to identity services daemon 1610 of peer device 1600. Identity services daemon 1610 can then transmit the message to application 1608 so that application 108 and application 1608 can synchronize data.

Example System Architecture

Figure 18:
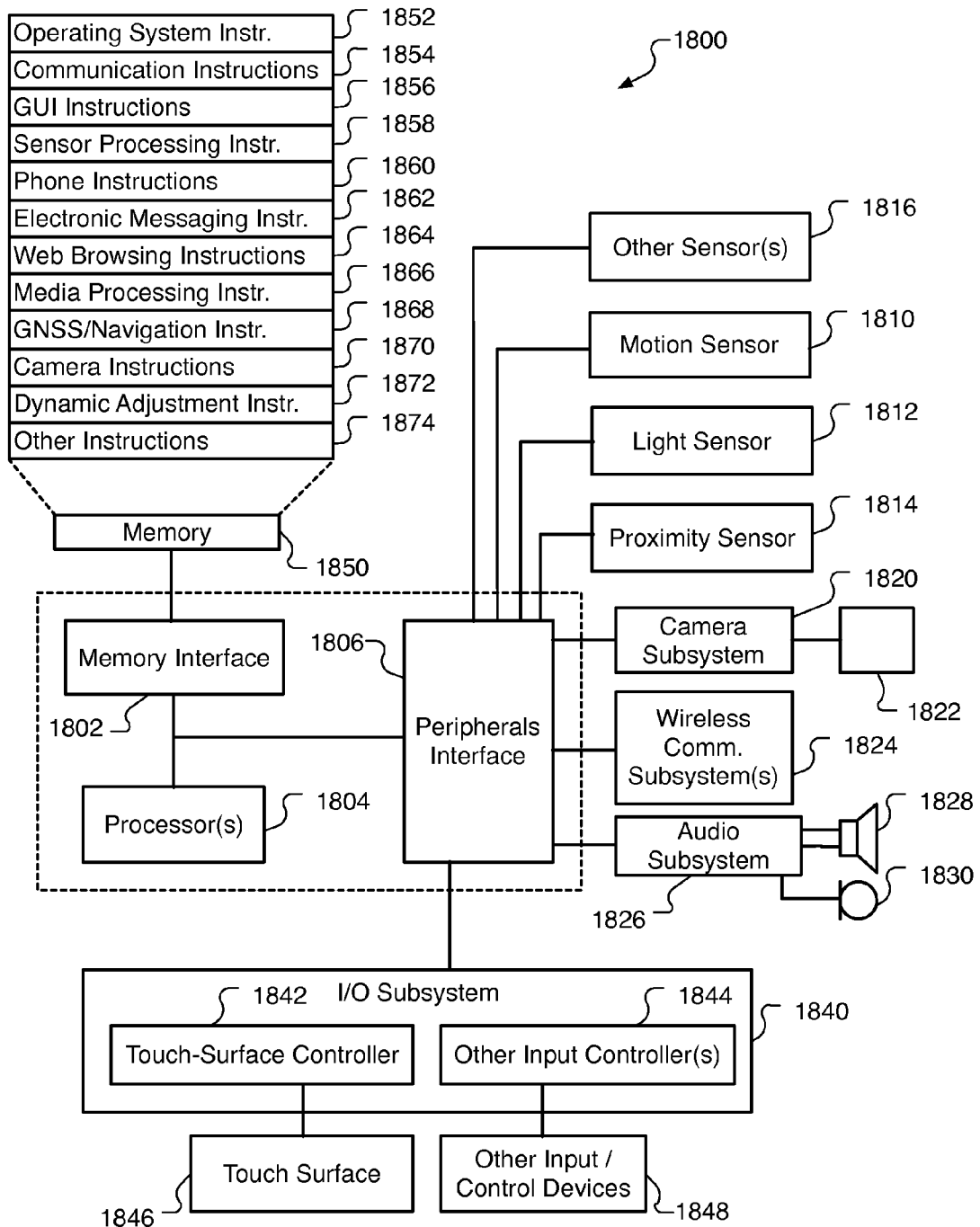
FIG. 18 is a block diagram of an example computing device that can implement the features and processes of FIGS. 1-17.

FIG. 18 is a block diagram of an example computing device 1800 that can implement the features and processes of FIGS. 1-17. Computing device 1800 can be a smartphone, a tablet computer, a laptop computer, a wearable device (e.g., a watch), a set top box, or a vehicle media system, for example. The computing device 1800 can include a memory interface 1802, one or more data processors, image processors and/or central processing units 1804, and a peripherals interface 1806. The memory interface 1802, the one or more processors 1804 and/or the peripherals interface 1806 can be separate components or can be integrated in one or more integrated circuits. The various components in the computing device 1800 can be coupled by one or more communication buses or signal lines.

Sensors, devices, and subsystems can be coupled to the peripherals interface 1806 to facilitate multiple functionalities. For example, a motion sensor 1810, a light sensor 1812, and a proximity sensor 1814 can be coupled to the peripherals interface 1806 to facilitate orientation, lighting, and proximity functions. Other sensors 1816 can also be connected to the peripherals interface 1806, such as a global navigation satellite system (GNSS) (e.g., GPS receiver), a temperature sensor, a biometric sensor, magnetometer or other sensing device, to facilitate related functionalities.

A camera subsystem 1820 and an optical sensor 1822, e.g., a charged coupled device (CCD) or a complementary metal-oxide semiconductor (CMOS) optical sensor, can be utilized to facilitate camera functions, such as recording photographs and video clips. The camera subsystem 1820 and the optical sensor 1822 can be used to collect images of a user to be used during authentication of a user, e.g., by performing facial recognition analysis.

Communication functions can be facilitated through one or more wireless communication subsystems 1824, which can include radio frequency receivers and transmitters and/or optical (e.g., infrared) receivers and transmitters. The specific design and implementation of the communication subsystem 1824 can depend on the communication network(s) over which the computing device 1800 is intended to operate. For example, the computing device 1800 can include communication subsystems 1824 designed to operate over a GSM network, a GPRS network, an EDGE network, a Wi-Fi or WiMax network, and a Bluetooth™ network. In particular, the wireless communication subsystems 1824 can include hosting protocols such that the device 100 can be configured as a base station for other wireless devices.

An audio subsystem 1826 can be coupled to a speaker 1828 and a microphone 1830 to facilitate voice-enabled functions, such as speaker recognition, voice replication, digital recording, and telephony functions. The audio subsystem 1826 can be configured to facilitate processing voice commands, voiceprinting and voice authentication, for example.

The I/O subsystem 1840 can include a touch-surface controller 1842 and/or other input controller(s) 1844. The touch-surface controller 1842 can be coupled to a touch surface 1846. The touch surface 1846 and touch-surface controller 1842 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch surface 1846.

The other input controller(s) 1844 can be coupled to other input/control devices 1848, such as one or more buttons, rocker switches, thumb-wheel, infrared port, USB port, and/or a pointer device such as a stylus. The one or more buttons (not shown) can include an up/down button for volume control of the speaker 1828 and/or the microphone 1830.

In one implementation, a pressing of the button for a first duration can disengage a lock of the touch surface 1846; and a pressing of the button for a second duration that is longer than the first duration can turn power to the computing device 1800 on or off. Pressing the button for a third duration can activate a voice control, or voice command, module that enables the user to speak commands into the microphone 1830 to cause the device to execute the spoken command. The user can customize a functionality of one or more of the buttons. The touch surface 1846 can, for example, also be used to implement virtual or soft buttons and/or a keyboard.

In some implementations, the computing device 1800 can present recorded audio and/or video files, such as MP3, AAC, and MPEG files. In some implementations, the computing device 1800 can include the functionality of an MP3 player, such as an iPod™.

The memory interface 1802 can be coupled to memory 1850. The memory 1850 can include high-speed random access memory and/or non-volatile memory, such as one or more magnetic disk storage devices, one or more optical storage devices, and/or flash memory (e.g., NAND, NOR). The memory 1850 can store an operating system 1852, such as Darwin, RTXC, LINUX, UNIX, OS X, WINDOWS, or an embedded operating system such as VxWorks.

The operating system 1852 can include instructions for handling basic system services and for performing hardware dependent tasks. In some implementations, the operating system 1852 can be a kernel (e.g., UNIX kernel). In some implementations, the operating system 1852 can include instructions for performing dynamic adjustment of the mobile device based on user activity. For example, operating system 1852 can implement the dynamic adjustment features as described with reference to FIGS. 1-17.

The memory 1850 can also store communication instructions 1854 to facilitate communicating with one or more additional devices, one or more computers and/or one or more servers. The memory 1850 can include graphical user interface instructions 1856 to facilitate graphic user interface processing; sensor processing instructions 1858 to facilitate sensor-related processing and functions; phone instructions 1860 to facilitate phone-related processes and functions; electronic messaging instructions 1862 to facilitate electronic-messaging related processes and functions; web browsing instructions 1864 to facilitate web browsing-related processes and functions; media processing instructions 1866 to facilitate media processing-related processes and functions; GNSS/Navigation instructions 1868 to facilitate GNSS and navigation-related processes and instructions; and/or camera instructions 1870 to facilitate camera-related processes and functions.

The memory 1850 can store other software instructions 1872 to facilitate other processes and functions, such as the dynamic adjustment processes and functions as described with reference to FIGS. 1-17.

The memory 1850 can also store other software instructions 1874, such as web video instructions to facilitate web video-related processes and functions; and/or web shopping instructions to facilitate web shopping-related processes and functions. In some implementations, the media processing instructions 1866 are divided into audio processing instructions and video processing instructions to facilitate audio processing-related processes and functions and video processing-related processes and functions, respectively.

Each of the above identified instructions and applications can correspond to a set of instructions for performing one or more functions described above. These instructions need not be implemented as separate software programs, procedures, or modules. The memory 1850 can include additional instructions or fewer instructions. Furthermore, various functions of the computing device 1800 can be implemented in hardware and/or in software, including in one or more signal processing and/or application specific integrated circuits.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed is:

1. A method comprising:
   receiving, by a first process executing on a mobile device, events generated by one or more client processes, each event including data associated with one of a plurality of attributes, where each of the attributes is associated with a budget and each of the events has a corresponding cost;
   receiving, from particular client process, a definition of a particular budget for a particular attribute;
   distributing, by the first process, the particular budget across a plurality of time periods according to historical usage information for the particular budget;
   reducing the particular budget for the particular attribute during a first time period based on the cost of events associated with the particular attribute received by the mobile device during the first time period;
   storing the event data in an event data store on the mobile device;
   receiving, by the first process, a request from a client process to initiate an event associated with the particular attribute during a current time period;
   comparing the cost of the event to the budget remaining for the particular attribute during the current time period; and
   determining, by the first process, to allow the event associated with the particular attribute based on the comparison.

2. The method of claim 1, wherein at least one of the plurality of attributes is dynamically defined by a client process at runtime.

3. The method of claim 1, wherein determining to allow the event comprises generating a forecast for the particular attribute that indicates when an event associated with the attribute is likely to occur.

4. The method of claim 1, wherein determining to allow the event comprises determining that there is enough budget remaining to cover the cost of the event.

5. The method of claim 4, wherein the budget corresponds to a portion of a system-wide data budget that corresponds to an amount of data that can be transmitted over a network connection within a period of time.

6. The method of claim 4, wherein the budget corresponds to a portion of a system-wide energy budget that is based on historical mobile device energy usage data.

7. A non-transitory computer-readable medium including one or more sequences of instructions which, when executed by one or more processors, causes:
   receiving, by a first process executing on a mobile device, events generated by one or more client processes, each event including data associated with one of a plurality of attributes, where each of the attributes is associated with a budget and each of the events has a corresponding cost;
   receiving, from particular client process, a definition of a particular budget for a particular attribute;
   distributing, by the first process, the particular budget across a plurality of time periods according to historical usage information for the particular budget;
   reducing the particular budget for the particular attribute during the first time period based on the cost of events associated with the particular attribute received by the mobile device during the first time period;

storing the event data in an event data store on the mobile device;

receiving, by the first process, a request from a client process to initiate an event associated with the particular attribute during a current time period;

comparing the cost of the event to the budget remaining for the particular attribute during the current time period; and determining, by the first process, to allow the event associated with the particular attribute based on the comparison.

8. The non-transitory computer-readable medium of claim 7, wherein at least one of the plurality of attributes is dynamically defined by a client process at runtime.

9. The non-transitory computer-readable medium of claim 7, wherein the instructions that cause determining to allow the event include instructions that cause generating a forecast for the particular attribute that indicates when an event associated with the attribute is likely to occur.

10. The non-transitory computer-readable medium of claim 7, wherein the instructions that cause determining to allow the event include instructions that cause determining that there is enough budget remaining to cover the cost of the event.

11. The non-transitory computer-readable medium of claim 10, wherein the budget corresponds to a portion of a system-wide data budget that corresponds to an amount of data that can be transmitted over a network connection within a period of time.

12. The non-transitory computer-readable medium of claim 10, wherein the budget corresponds to a portion of a system-wide energy budget that is based on historical mobile device energy usage data.

13. A system comprising:
one or more processors; and
a computer-readable medium including one or more sequences of instructions which, when executed by the one or more processors, causes:
receiving, by a first process executing on a mobile device, events generated by one or more client processes, each event including data associated with one of a plurality of attributes, where each of the attributes is associated with a budget and each of the events has a corresponding cost;

receiving, from particular client process, a definition of a particular budget for a particular attribute;

distributing, by the first process, the particular budget across a plurality of time periods according to historical usage information for the particular budget;

reducing the particular budget for the particular attribute during the first time period based on the cost of events associated with the particular attribute received by the mobile device during the first time period;

storing the event data in an event data store on the mobile device;

receiving, by the first process, a request from a client process to initiate an event associated with the particular attribute during a current time period;

comparing the cost of the event to the budget remaining for the particular attribute during the current time period; and determining, by the first process, to allow the event associated with the particular attribute based on the comparison.

14. The system of claim 13, wherein at least one of the plurality of attributes is dynamically defined by a client process at runtime.

15. The system of claim 13, wherein the instructions that cause determining to allow the event include instructions that cause generating a forecast for the particular attribute that indicates when an event associated with the attribute is likely to occur.

16. The system of claim 13, wherein the instructions that cause determining to allow the event include instructions that cause determining that there is enough budget remaining to cover the cost of the event.

17. The system of claim 16, wherein the budget corresponds to a portion of a system-wide data budget that corresponds to an amount of data that can be transmitted over a network connection within a period of time.

18. The system of claim 16, wherein the budget corresponds to a portion of a system-wide energy budget that is based on historical mobile device energy usage data.

* * * * *